United States Patent [19]
Iida et al.

[11] Patent Number: 5,871,995
[45] Date of Patent: Feb. 16, 1999

[54] PURIFIED ENZYMES PARTICIPATING IN C-TERMINAL AMIDATION

[75] Inventors: Toshii Iida; Toshihiko Kaminuma; Yuka Fuse; Masahiro Tajima; Mitsuo Yanagi, all of Yokohama; Hiroshi Okamoto, Sendai; Jiro Kishimoto; Ohji Ifuku, both of Yokohama; Ichiro Kato, Sendai, all of Japan

[73] Assignee: Shiseido Company, Ltd., Tokyo, Japan

[21] Appl. No.: 70,301

[22] PCT Filed: Apr. 12, 1990

[86] PCT No.: PCT/JP90/01036

§ 371 Date: May 24, 1991

§ 102(e) Date: May 24, 1991

[87] PCT Pub. No.: WO91/02790

PCT Pub. Date: Mar. 7, 1991

[30] Foreign Application Priority Data

| | | | |
|---|---|---|---|
| Aug. 15, 1989 | [JP] | Japan | 1-209687 |
| Oct. 19, 1989 | [JP] | Japan | 1-281933 |
| Mar. 26, 1990 | [JP] | Japan | 2-76331 |
| Apr. 24, 1990 | [JP] | Japan | 2-106412 |
| Aug. 2, 1990 | [JP] | Japan | 2-205475 |

[51] Int. Cl.$^6$ .............. C12N 9/48; C12N 9/14; C12N 9/78; C12N 9/80

[52] U.S. Cl. .............. 435/212; 435/195; 435/227; 435/228; 435/471

[58] Field of Search .............. 435/155, 106, 435/193, 195, 212, 227, 228, 471

[56] References Cited

U.S. PATENT DOCUMENTS

| | | | |
|---|---|---|---|
| 4,693,985 | 9/1987 | Degen et al. | 436/531 |
| 4,708,934 | 11/1987 | Gilligan et al. | 435/68 |

FOREIGN PATENT DOCUMENTS

| | | |
|---|---|---|
| 0 308 067 | 3/1989 | European Pat. Off. . |
| 0 447 547 | 9/1991 | European Pat. Off. . |
| 0 465 404 B1 | 1/1992 | European Pat. Off. . |
| 3-262484 | 11/1991 | Japan . |
| PCT/US88/03172 | 3/1989 | WIPO . |
| WO 89/02460 | 3/1989 | WIPO . |

OTHER PUBLICATIONS

A. Bradbury et al., "Mechanism of C–terminal amide Formation By Pituitary Enzymes," Nature, vol. 298, Aug. 12, 1982, pp. 686–688.

K. Ohsuye et al., "Cloning of cDNA Encoding A New Peptide C–Terminal α–Amidating Enzyme . . . ," BBRC, vol. 150, Feb. 15, 1988, pp. 1275–1281.

K. Mizuno et al., "Peptide C–Terminal α–Amidating Enzyme Purified to Homogeneity . . . ," BBRC, vol. 137, Jun. 30, 1986, pp. 984–991.

A. Katopodis et al., "A Novel Enzyme from Bovine Neurointermediate Pituitary Catalyzes Dealkylation of α–Hydroxyglycine Derivatives, Thereby Functioning Sequentially with Peptidylglycine α–Amidating Monooxygenase in Peptide Amidation", Biochemistry, vol. 29, No. 26, Jul. 3, 1990, pp. 6115–6120.

K. Takahashi et al., "Peptidylglycine α–Amidating Reaction: Evidence for A Two–Step Mechanism Involving a Stable Intermediate at Neutral pH", Biochemical and Biophysical Research Communications, vol. 169, No. 2, Jun. 15, 1990, pp. 524–530.

J. Glauder et al., "Human Peptidylglycime α–Amidating Monooxygenase: cDNA, Cloning and Functional Expression of a Truncated Form in Cos Cells", Biochemical and Biophysical Research Communications, vol. 169, No. 2, Jun. 15, 1990, pp. 551–558.

A. Murthy et al., "Purification and Characterization of Peptidylglycine α–Amidating Monooxygenase from Bovine Neurointermediate Pituitary", The Journal of Biological Chemistry, vol. 261, No. 1., Feb. 5, 1986, pp. 1815–1822.

Stoffers et al., Proc. Natl. Acad. Sci., USA, Jan. 1989, vol. 86, pp. 735–739.

Betty A. Eipper et al., "Structure of the Precursor to an Enzyme Mediating COOH–Terminal Amidation in Peptide Biosynthesis", *Molecular Endocrinology*, vol. 1 No. 11, pp. 777–790 (1987).

Doris A. Stoffers et al., "Alternative mRNA splicing generates multiple forms of peptidyl–glycine α–amidating monooxygenase in rat atrium", *Proc. Natl' Acad. Sci. USA*, vol. 86, pp. 735–739 (Jan. 1989).

(List continued on next page.)

*Primary Examiner*—David M. Naff
*Attorney, Agent, or Firm*—Foley & Lardner

[57] ABSTRACT

A purified enzyme-I is obtained that participates in C-terminal amidation by acting on a peptide C-terminal glycine adduct to form a peptide C-terminal α-hydroxyglycine adduct. The enzyme has an optimum pH of about 5 to 7, an optimum temperature of 25° to 40° C. and a molecular weight of about 25 kDa or about 36 kDa, and metal ions and ascorbic acid act as a cofactor. A purified enzyme-II is obtained that participates in C-terminal amidation by acting on a peptide C-terminal α-hydroxyglycine adduct to produce a C-terminal amidated compound. The enzyme has an optimum pH of about 5 to 6, an optimum temperature of 15° to 35° C. and a molecular weight of about 40 kDa or about 43 kDa. Enzyme-I does not act on the peptide C-terminal α-hydroxyglycine adduct and enzyme-II does not act on the peptide C-terminal glycine adduct. The enzymes may be purified from a biological material such as horse serum by affinity chromatography using a peptide C-terminal glycine adduct as a ligand. The enzymes may also be obtained from host cells transformed with a plasmid containing a cDNA coding for the enzymes. Assay of activity of the enzymes is carried out by measuring adduct (II) or the compound (III) that has been isolated such as by high performance liquid chromatography with the use of an acetonitrile-containing buffer.

20 Claims, 49 Drawing Sheets

OTHER PUBLICATIONS

Masahiro Tajima et al., "The Reaction Product of Peptidylglycine α–Amidating Enzyme Is a Hydroxyl Derivative at α–Carbon of the Carboxyl–terminal Glycine", *The Journal of Biological Chemistry*, vol. 265, No. 17, pp. 9602–9605, Issue of Jun. 15, 1990.

D. Stoffers et al., "Alternative mRNA Splcing Generates Multiple Forms of Peptidyl–glycine α–amidating Monooxygenase in Rate Atrium", Proc. Natl. Acad. Sci. USA, vol. 86, Jan. 1989, pp. 735–739.

Young et al., "Enzymatic Peptidyl α–Amidation Proceeds through Formation of an α–Hydroxyglycine Intermediate", J. Am. Chem. Soc., vol. 111, No. 5, Mar. 1989, pp. 1933–1934.

Biochemical and Biophysical Research Communication, vol. 151, No. 1 (1988), A. G. Katopodis, et. al., pp. 499–505.

Biochemistry, vol. 29, No. 26, (1990), A. G. Katopodis, et al., pp. 6115–6120.

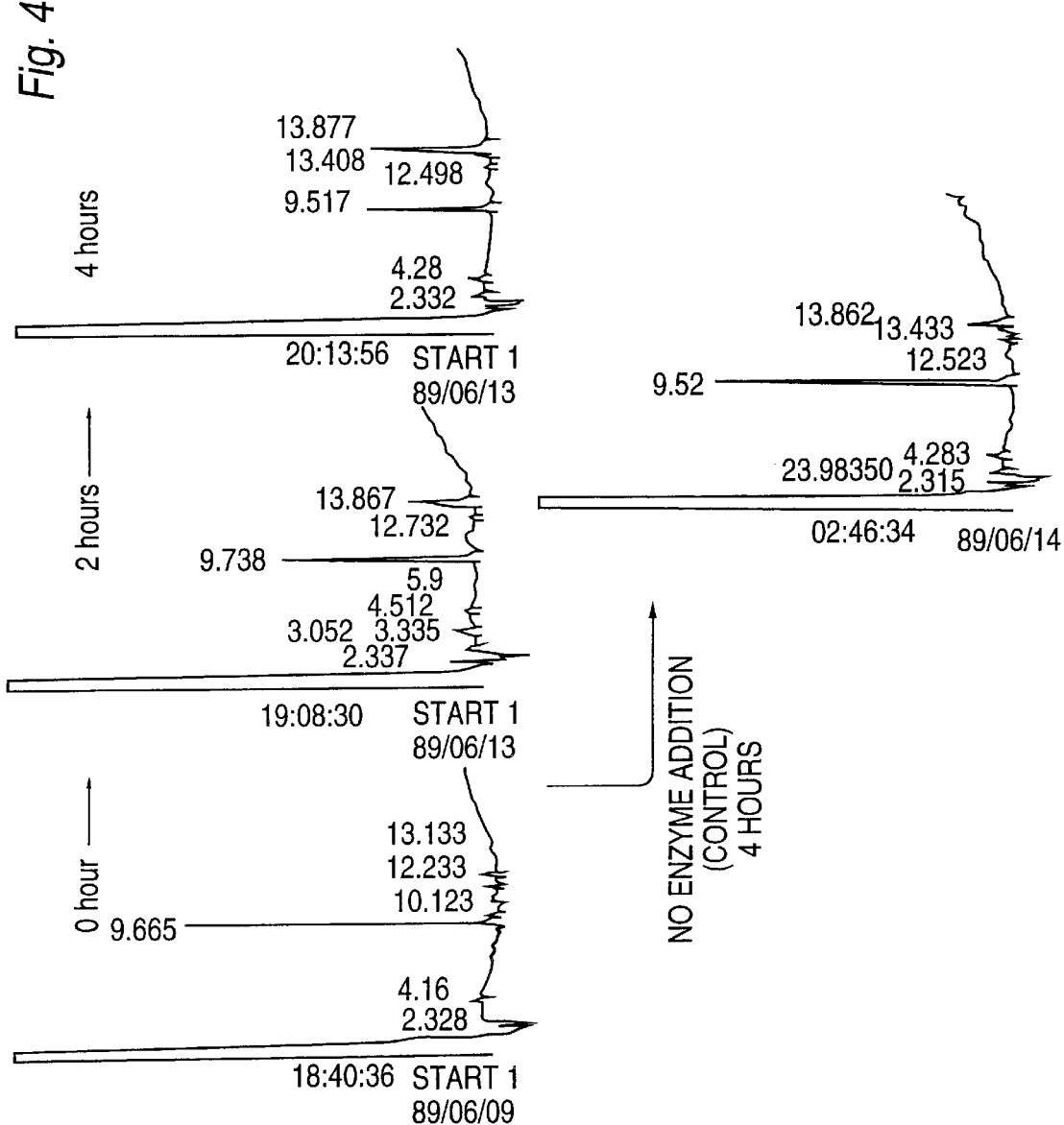

Fig. 5(A)

```
                         10            20            30
Human    → MAGRVFS--LLVLL--V-FPSSCLAFRSPLSVFKRF
Horse    → MAG-LRS--LLVLL-LV-FQSSCLGFRSPLSVFKRF
Bovine   → MAG-FRS--LLVLL-LV-FRSGCMGFRSPLSVFKRF
Rat      → MAGRARSGLLLLLLGLLALQSSCLAFRSPLSVFKRF
Frog II  → MDMAS-LISS-LLVL--FLIFQNSCYCFRSPLSVFKRY
Frog I   → MAS-LSSS-FLVL--FLLFQNSCYCFRSPLSVFKRY 120           130           140
         LFGCNMPSSTGSYWFCDEGTCTDKANILYAWARNAP
         LFGCNMPSSTGSYWFCDEGVCTDKANILYAWARNAP
         LFGCNMPASTGNYWFCDEGTCTDKANILYAWARNAP
         LFGCNMPSSTGSYWFCDEGTCTDKANILYAWARNAP
         LFGCNMPSSTGDYWDCSAGTCNDKSSIMYAWAKNAP
         LFGCNIPSSTGDYWDCSAGTCMDKSSIMYAWAKNAP 230           240           250
         VNSDISCHYKNYPMHVFAYRVHTHHLGKVVSGYRVR
         VNSDLSCHYKKYPMHVFAYRVHTHHLGKVVSGYRVR
         VNSDISCHYKKYPMHVFAYRVHTHHLGKVVSGYRVR
         VNADISCQYKMYPMHVFAYRVHTHHLGKVVSGYRVR
         VNSDIACLYNRPTIHPFAYRVHTHQLGQVVSGFRVR
         VNSDIACLYNRPTIHPFAYRVHTHQLGQVVSGFRVR 340           350           360
         FMTCTQNVAEEMFRTIPPEANIPIPVKSDMVMM---
         FMTCTQNVAEEMFRTIPPEANIPIPVKSDMVMM---
         FMTCTQNVAEDIFRTIPPEANIPIPVKSDMVMM---
         FMTCTKNVAEDMFRTIPAEANIPIPVKPDMVMM---
         YMTCVQTGNEKLFENIPEIANVPIPVSPDMMMMMMM
         YMTCVQTGEPKLFQNIPEIANVPIPVSPDMMMM--M
```

Fig. 5(B)

```
          40         50         60         70
KETTRPFSNECLGTTRPVVPIDSSDFALDIRMPGVT
KETTRPFSNECLGTTRPVIPIDSSDFALDIRHPGVT
KETTRSFSNECLGTTRPVIPIDSSDFALDIRMPGVT
KETTRSFSNECLGTIGPVTHLLASDFALDIRMPGVT
EESTRSLSNDCLGTTRPVMSPGSSDYTLDIRMPGVT
EESTRSLSNDCLGTTRPVMSPGSSDYTLDIRMPGVT 150        160        170        180
PTRLPKGVGFRVGGETGSKYFVLQVHYGDISAFRDN
PTRLPKGVGFRVGGETGSKYFVLQVHYGDISAFRDN
PTRLPKGVGFRVGGETGSKYFVLQVHYGDISAFRDN
PTRLPKGVGFRVGGETGSKYFVLQVHYGDISAFRDN
PTKLPEGVGFQVGGKSGSRYFVLQVHYGDVKAFQDK
PTKLPEGVGFRVGGKSGSRYFVLQVHYGNVKAFQDK 260        270        280        290
NGQWTLIGRQSPQLPQAFYPVGHPVDVSFGDLLAAR
NGQWTLIGRQSPQLPQAFYPVEHPVDVSFGDILAAR
NGQWTLIGRQSPQLPQAFYPVEHPVDVSFGDILAAR
NGQWTLIGRQNPQLPQAFYPVEHPVDVTFGDILAAR
HGKWTLIGRQSPQLPQAFYPVEHPLEISPGDIIATR
HGKWSLIGRQSPQLPQAFYPVEHPVEISPGDIIATR 370        380        390        400
-HEHHKETEYKDKIPLLQQPKREEEEVLEQGDFYSL
-HGHHKETENKDKTS-LQQPKQEEE-VLEQGDFYSL
-HGHHKETENKDKTSLLQQPKREEEGVLEQGDFYSL
-HGHHKEAENKEKSALMQQPKQGEEVVLEQGDFYSL
GHGHHHTEAEAETNTALQQPKREEEVVLNQ------
GHGHHHTEAEPEKNTGLQQPKREEEVVLDQGLITLG
```

Fig. 5(C)

```
        80          90         100        110
PKQSDTYFCMSMRIPVDEEAFVIDFKPRASMDTVHHML
PKQSDTYFCMSMRLPMDEETFVIDFKPRASMDTVHHML
PKQSDTYFCMSVRLPMDEEAFVIDFKPRASMDTVHHML
PKESDTYFCMSMRLPVDEEAFVIDFKPRASMDTVHHML
HTESDTYLCKSYRLPVDDEAYVMDYRPHANMDTAHHML
HTESDTYLCKSYRLPVDDEAYVMDFRPHANMDTAHHML 190         200        210        220
NKDCSGVSLHLTRLPQPLIAGMYLMMSVDTVIPAGEKV
HKDCSGVSLHLTRLPQPLIAGMYLMMALDTVIPAGEKV
HKDCSGVSLHLTRLPQPLIAGMYLMMSVDTVIPPGGKV
HKDCSGVSVHLTRVPQPLIAGMYLMMSVDTVIPPGEKV
HKDCTGVTVRITPEKQPLIAGIYLSMSLNTVVPPGQEV
HKDCTGVTVRVTPEKQPQLAGIYLSMSVDTVIPPGEEA 300         310        320        330
CVFIGEGRTEATHIGGTSSDEMCNLYIMYYMEAKHAVS
CVFTGEGRTEATHIGGTSSDEMCNLYIMYYMEAKHAVS
CVFTGEGRTEVTHIGGTSSDEMCNLYIMYYMEAKHAVS
CVFTGEGRTEATHIGGTSSDEMCNLYIMYYMEAKYALS
CLFTGKGRMSATYIGGTAKDEMCNLYIMYYMDAAHATS
CLFTGKGRTSATYIGGTSNDEMCNLYIMYYMDAAHATS 410         420        430        440
LSKLLGEREDVVHVHKYNPTEKAESESDLVAEIANVVQ →Human
LSKLLGEREDVVHVHKYNPTEKAESESDLVAEIANVVQ →Horse
LSKLLGEREDVVHVHKYNPTEKAESESDLVAEIANVVQ →Bovine
LSKLLGEREDVVHVHKYNPTEKTESGSDLVAEIANVVQ →Rat
------------------------------------- →Frog II
DSAV →Flog
```

Fig. 5(D)

```
                    450        460        470
Human     →KKDLGRSDAREGAE-HE-RGNAILVRDRIHKFHRLVS
Horse     →KKDLGRSDARESAE-HE DRGNAILVRDRIHKFHRLES
Bovine    →KKDLGRSD I RESAE-QE-RGNAILVRDRIHKFHRLVS
Rat       →KKDLGRSDARE GAEHE E-WGNAILVRDRIH R FH Q LES
Frog II   →---------------------------------------

560        570        580
          FDSKFVYQQIGLGPIEEDTILVIDPNNAAVLQSSEKN
          FDSKFVYQQRGLGPIEEDTILVIDPNNAAVLQSSGKN
          FDSKFVYQQRGLGPIEEDTILVIDPNNAAVLQSSGKN
          FDSKFVYQQRGLGPIEEDTILVIDPNNAEILQSSGKN
          FDRNFVYQQRGTGPIQESTILVVDPNTSKVLKSTGQN 670        680        690
          GYCNSRIVQFSPSGKFITQWGEESSGSSPLPGQFTVP
          GYCNSRIVQFSPTGRFITQWGEESSESNPKPGQFRVP
          GYCNSRLVQFSPSGKFITHWGEASLESSPKPGQFRVP
          GYCNSRIVQFSPSGKFMTQWGEESSGSSPRPGQFSVP
          GYCNSRIMQFSPNGMFIMQWGEETSSNLPRPGQFRTP 780        790        800
          FVMNFSNGEIIDIFKPVRKHFDMPHDIVASEDGTVYI
          FVMNFSSGEIIDVFKPVRKHFDMPHDITASEDGTVYV
          FVMNFSSGEIIDVFKPVRKHFDMPHDIAASEDGTVYV
          FVMNFSSGEIIDVFKPVRKHFDMPHDIVASEDGTVYI
          FMTNFSNGDILTETHARKNFMPHDIAAGDDGTVYV 890        900        910
          VLITTLLVIPVVVLLAIAIFIRWKKSR-AFGDSEHKL
          VLITTLLVIPVVVLLAIAIFIRWKKSR-AFCESEHKV
          VLITTLLVIPVVVLLAIALFIRWKKSR-AFGDSERKL
          VLITTLLVIPVLVLLAIVMFIRWKKSR-AFGDHDRKL
          VLITTLLTIPVVVLTAIAIFIRWRKVR MYGGDIGHKS
```

Fig. 5(E)

```
        480        490        500        510        520
TLRHPESRVFSLQQPPPGEGTWEPEHTGDFHMEEALDWPGVYL
TLRHTESRVISVPQPLPGEGTWEPEHTGDFHVEEALDWPGVYL
TLRHAESRVLSLQQPLPGEGTWEPEHTGDFHVEEALDWPGVYL
TLRHAESRAFSFQQ--PGEGPWEPEPSGDFHVEEELDWPGVYL
-----------------------DVHLEEDTDWPGVNL 590        600        610        620        630
LFYLPHGLSIDKDGNYWVTDVALHQVFKLDPNNKEGPVLILGR
LFYLPHGLSIDKDGNYWVTDVALHQVFKLDPNSKEGPLLILGR
LFYLPHGLSIDKDGNYWVTDVALHQVFKLDPKSKEGPLLTLGR
LFYLPHGLSIDTDGNYWVTDVALHQVFKLDPHSKEGPLLILGR
LFFLPHGITIDRDGNYWVTDVALHQVFK-VGAEKETPLLVLGR 700        710        720        730        740
HSLALVPLLGQLCVADRENGRIQCFKTDTKEEVREIKHSSFGR
HSLALVPHLGQLCVADRENGRIQCFKTDTKEFVREIKHASFGR
HSLALVPPLGQLCVADRENGRIQCFKTDTKEFVREIKHPSFGR
HSLALVPHLDQLCVADRENGRIQCFKTDTKEFVREIKHASFGR
HSLTMISDQGQLCVADRENGRIQCFIAKTGEFVKQIKHDEFGR 810        820                   840        850
GDAHTNTVWKFTLTEKLEHRSVKKAGIEVQEIKEAEAVVETKM
GDAHTNTVWKFTSTERVEHRSVKKAGIEVQEIKESEAVVETKM
GDAHTNTVWKFTSTEKMEHRSVKKAGIEVQEIKESEAVVETKM
GDAHTNTVWKFTLTEKMEHRSVKKAGIEVQEIKEAEAVVEPKV
GDAHANAVWKF-SPSKAEHRSVKKAGIEVEEITETE-IFETHM 920        930        940        950        960
ETSSGRVLGRFRGKGSGGLNLGNFFASRKGYSRKGFDRLSTEG
EASSGRVLGRLRGKGSGGLNLGNFFASRKGYSRKGFDRLSTEG
EASSGRVLGRLRGKGGGGLNLGNFFASRKGYSRKGFDRLSTEG
ESSSGRVLGRFRGKGSGGLNLGNFFASRKGYSRKGFDRVSTEG
ESSSGILGKLRGKGSGGLNLGTFFATHKGYSRKGFDRLSTEG
```

Fig. 5(F)

```
            530        540        550
    LPGQVSGVALDPKNNLVIFHRGDHVWDGNS
    LPGQVSGVALDLQNNLVIFHRGDHVWDGNS
    LPGQVSGVALDPQNNLVIFHRGDHVWDGNS
    LPGQVSGVALDSKNNLVIFHRGDHVWDGNS
    KVGQVSGLALDPKNNLVIFHRGDHVWDENS 640        650        660
    SMQPGSDQNHFCQPTDVAVDPGTGAIYVSD
    SMQPGSDQNHFCQPTDVAVDPNTGTIFVSD
    SMQPGSDQNHFCQPTDVAVDPDTGTIYVSD
    SMQPGSDQNHFCQPTDVAVEPSTGAVFVSD
    AFQPGSDRKHFCQPTDVAVDPITGNFFVAD 750        760        770
    NVFAISYIP-GLLFAVNGKPHFGDQEPVQG
    NVFAISYIP-GLLFAVNGKPYFGDQKPVQG
    NVFAISYIP-GLLFAVNGKPYFEDQEPVQG
    NVFAISYIP-GFLFAVNGKPYFGDQEPVQG
    EVFAVSYAPGGVLYAVNGKPYYGDSTPVQG 860        870        880
    --ENKPTSSELQKMQEKQKLIKEPGSGVPV
    --ENKPASSELQKMQEKQKLIKEPGSGVPV
    --ENKPASSELQKIQEKQKLVKEPGSGVPA
    --ENKPTSSELQKMQEKQKLSTEPGSGVSV
    RSRPKTNESVGQQTQEKPSVVQESSAGVSF 970        980        990
    SDQEK--EDDGSESEEEYSAPLPALAPSSS   → Human
    SDQEK-DEDDGSESEEEYSAPLPAPVPSSS   → Horse
    SDQEK-DE-DASESEEEYSAPPPAPAPSS    → Bovine
    SDQEK-DEDDGTESEEEYSAPLHKPAPSS    → Rat
    SDQQKDDDDGSDSEEEYSAPPIPPV-SSS    → Frog II
```

Fig. 6(A)

```
CATGGCCGGACGCGCCCGCAGCGGTCTGCTACTGCTGCTGCTGGGGCTGCT
MetAlaGlyArgAlaArgSerGlyLeuLeuLeuLeuLeuLeuGlyLeuLe
                        10
TCTGTCTTTAAGAGGTTTAAAGAAACTACCAGATCATTTTCCAATGAATG
SerValPheLysArgPheLysGluThrThrArgSerPheSerAsnGluCy
                        40
GATTTTGCGCTGGATATTCGCATGCCTGGGGTTACACCTAAAGAGTCTGA
AspPheAlaLeuAspIleArgMetProGlyValThrProLysGluSerAs
                        70
GAAGCCTTCGTGATTGACTTCAAGCCTCGTGCCAGCATGGATACTGTCCA
GluAlaPheValIleAspPheLysProArgAlaSerMetAspThrValHi
                        100
GGAAGTTACTGGTTTTGTGATGAAGGAACCTGTACAGATAAAGCCAATAT
GlySerTyrTrpPheCysAspGluGlyThrCysThrAspLysAlaAsnIl
                        130
CCGAAAGGTGTTGGATTCAGAGTTGGAGGAGAAACTGGAAGCAAATACTT
ProLysGlyValGlyPheArgValGlyGlyGluThrGlySerLysTyrPh
                        160
GATAATCACAAAGACTGCTCTGGCGTGTCCGTACATCTCACACGTGTGCC
AspAsnHisLysAspCysSerGlyValSerValHisLeuThrArgValPr
                        190

GACACTGTCATACCACCAGGAGAGAAAGTAGTGAATGCTGACATTTCGTG
AspThrValIleProProGlyGluLysValValAsnAlaAspIleSerCy
                        220
GTCCACACTCACCATTTAGGTAAGGTGGTGAGCGGATACAGAGTAAGAAA
ValHisThrHisHisLeuGlyLysValValSerGlyTyrArgValArgAs
                        250
CCACAGGCTTTCTACCCTGTGGAACACCCCGTTGATGTTACTTTTGGTGA
ProGlnAlaPheTyrProValGluHisProValAspValThrPheGlyAs
                        280
ACAGAGGCCACCCACATCGGCGGCACTTCTAGTGACGAAATGTGTAACCT
ThrGluAlaThrHisIleGlyGlyThrSerSerAspGluMetCysAsnLe
                        310
```

Fig. 6(B)

```
CGCCCTGCAGAGCAGCTGCCTGGCCTTCAGAAGCCCACTT           90
uAlaLeuGlnSerSerCysLeuAlaPheArgSerProLeu
   20                                30
CCTTGGTACCATTGGACCAGTCACCCCTCTTGATGCATCA          180
sLeuGlyThrIleGlyProValThrProLeuAspAlaSer
   50                                60
CACATACTTCTGCATGTCCATGCGTCTGCCTGTGGATGAG          270
pThrTyrPheCysMetSerMetArgLeuProValAspGlu
   80                                90
CCATATGCTGCTGTTTGGATGCAATATGCCCTCGTCCACT          360
sHisMetLeuLeuPheGlyCysAsnMetProSerSerThr
  110                               120
TCTATATGCCTGGGCAAGGAATGCTCCCCCCACCCGGCTC          450
eLeuTyrAlaTrpAlaArgAsnAlaProProThrArgLeu
  140                               150
CGTCCTTCAAGTTCACTATGGCGATATCAGTGCTTTTCGA          540
eValLeuGlnValHisTyrGlyAspIleSerAlaPheArg
  170                               180
CCAGCCTTTAATTGCGGGCATGTACCTTATGATGTCTGTT          630
oGlnProLeuIleAlaGlyMetTyrLeuMetMetSerVal
  200                               210

CCAATACAAAATGTATCCAATGCATGTGTTTGCCTACAGA          720
sGlnTyrLysMetTyrProMetHisValPheAlaTyrArg
  230                               240
CGGACAGTGGACACTGATTGGACGCCAGAACCCCCAGCTG          810
nGlyGlnTrpThrLeuIleGlyArgGlnAsnProGlnLeu
  260                               270
TATACTGGCAGCCAGATGTGTGTTCACTGGTGAAGGGAGG          900
pIleLeuAlaAlaArgCysValPheThrGlyGluGlyArg
  290                               300
GTACATCATGTATTACATGGAAGCCAAATATGCACTTTCC          990
uTyrIleMetTyrTyrMetGluAlaLysTyrAlaLeuSer
  320                               330
```

Fig. 6(C)

```
TTCATGACCTGTACAAAGAACGTGGCTCCAGATATGTTCAGAACTATCCC
PheMetThrCysThrLysAsnValAlaProAspMetPheArgThrIlePr
                                                340
GTTATGATGCACGGGCATCACAAAGAAGCAGAAAACAAAGAAAAGAGTGC
ValMetMetHisGlyHisHisLysGluAlaGluAsnLysGluLysSerAl
                                                370
              ▼A
GAGCAGG|ATTTCCATGTGGAAGAAGAACTGGACTGGCCTGGAGTGTACTT
GluGlnA|spPheHisValGluGluGluLeuAspTrpProGlyValTyrLe
       Δ
                                                400
AATAACCTRGTGATTTTCCACAGAGGTGACCATGTTTGGGATGGAAACTC
AsnAsnLeuValIlePheHisArgGlyAspHisValTrpAspGlyAsnSe
                                                430
CCAATTGAAGAAGACACCATCCTGGTCATTGACCCAAATAATGCTGAAAT
ProIleGluGluAspThrIleLeuValIleAspProAsnAsnAlaGluIl
                                                460
GGCTTGAGCATAGATACAGATGGAAATTATTGGGTCACAGATGTGGCTCT
GlyLeuSerIleAspThrAspGlyAsnTyrTrpValThrAspValAlaLe
                                                490
CCTCTCTTAATTCTGGGAAGGAGCATGCAACCTGGGAGTGACCAAAATCA
ProLeuLeuIleLeuGlyArgSerMetGlnProGlySerAspGlnAsnHi
                                                520
GGAGCTGTCTTCGTGTCAGACGGTTACTGTAACAGTCGGATTGTGCAGTT
GlyAlaValPheValSerAspGlyTyrCysAsnSerArgIleValGlnPh
                                                550
TCCTCTGGAAGCAGTCCTAGGCCAGGCCAGTTCAGTGTTCCTCACAGTTT
SerSerGlySerSerProArgProGlyGlnPheSerValProHisSerLe
                                                580
AGGGAAAATGGCCGAATCCAATGCTTCAAAACTGACACCAAAGAATTTGT
ArgGluAsnGlyArgIleGlnCysPheLysThrAspThrLysGluPheVa
                                                610
GCCATTTCATATATACCAGGTTTCCTCTTTGCCGTAAACGGGAAGCCTTA
AlaIleSerTyrIleProGlyPheLeuPheAlaValAsnGlyLysProTy
                                                640
```

Fig. 6(D)

```
AGCAGAGGCCAATATCCCAATTCCTGTCAAACCGGACATG         1080
oAlaGluAlaAsnIleProIleProValLysProAspMet
350                                     360
TTTAATGCAGCAGCCAAAACAGGGAGAGGAAGAAGTATTA         1170
aLeuMetGlnGlnProLysGlnGlyGluGluGluValLeu
380                                     390
GTTACCAGGCCAGGTTTCTGGGGTGGCCCTGGATTCTAAG         1260
uLeuProGlyGlnValSerGlyValAlaLeuAspSerLys
410                                     420
TTTTGACAGCAAGTTTGTTTACCAGCAAAGAGGTCTTGGG         1350
rPheAspSerLysPheValTyrGlnGlnArgGlyLeuGly
440                                     450
CCTCCAGTCCAGTGGCAAGAACCTGTTTTATTTACCACAC         1440
eLeuGlnSerSerGlyLysAsnLeuPheTyrLeuProHis
470                                     480
CCACCAGGTGTTCAAATTGGACCCGCATAGCAAAGAAGGC         1530
uHisGlnValPheLysLeuAspProHisSerLysGluGly
500                                     510
TTTCTGCCAGCCCACCGATGTGGCTGTGGAGCCCAGTACT         1620
sPheCysGlnProThrAspValAlaValGluProSerThr
530                                     540
TTCACCAAGCGGAAAGTTCGTCACCCAGTGGGGAGAAGAG         1710
eSerProSerGlyLysPheValThrGlnTrpGlyGluGlu
560                                     570
GGCCCTTGTGCCTCATTTGGACCAGTTGTGTGTGGCAGAC         1800
uAlaLeuValProHisLeuAspGlnLeuCysValAlaAsp
590                                     600
GAGAGAGATTAAGCACGCATCATTTGGAAGGAATGTCTTT         1890
lArgGluIleLysHisAlaSerPheGlyArgAsnValPhe
620                                     630
CTTTGGAGACCAAGAGCCCGTGCAAGGATTTGTGATGAAC         1980
rPheGlyAspGlnGluProValGlnGlyPheValMetAsn
650                                     660
```

Fig. 6(E)

```
TTTTCCAGTGGGGAAATTATAGACGTCTTCAAGCCAGTACGCAAGCA
PheSerSerGlyGluIleIleAspValPheLysProValArgLysHi
                            670
GTGTACATTGGAGACGCACACACAAACACCGTGTGGAAGTTCACCCT
ValTyrIleGlyAspAlaHisThrAsnThrValTrpLysPheThrLe
                            700
GAAGTCCAGGAAATCAAAGAAGCCGAGGCAGTTGTTGAACCCAAAGT
GluValGlnGluIleLysGluAlaGluAlaValValGluProLysVa
                            730
AAACAGAAACTGAGCACAGAGCCCGGCTCGGGAGTGTCCGTGGTTCT
LysGlnLysLeuSerThrGluProGlySerGlyValSerValValLe
                            760
ATTGTCATGTTTATTCGGTGGAAAAAATCAAGGGCCTTTGGAGGAAA
IleValMetPheIleArgTrpLysLysSerArgAlaPheGlyGlyLy
                            790
AAAGGCTACAGCAGAAAAGGGTTTGACCGAGTGAGCACAGAGGGGAG
LysGlyTyrSerArgLysGlyPheAspArgValSerThrGluGlySe
                            820
GAGTACTCGGCCCCGCTGCCCAAGCCTGCACCTTCCTCCTGAGCTCC
GluTyrSerAlaProLeuProLysProAlaProSerSer
                            850
AGACTCCTTCCCCTTTAGCGCGTGTAAAGTTCTGTGCATTTGATTGT
TCATTTGGCTCCGTTGGCTTCTGTTTTCTAGGTGAGGAGTTCCCCAC
AGAAGCCGCCCTCCTCTTCCAAGGTAGCGCTCCAACCCCCGAGGGAA
AAATAGCCCTATTCTCTGCTTGAACACAGTATTCTCCCAGTCCACAC
CTCAGCCTGTGGCAGTGAAGAGAACCAACCTGCCACACGACGAAAAG
TTGCAATGAGAGAAATTTTAAAAAGTCTCTATTTAAATTCTTTTTTT
AGATGGTTACACTGTTAGAACACTATTTTTCAGAATCTGAATGTAAT
```

Fig. 6(F)

```
CTTCGACATGCCTCATGATATTGTGGCTTCTGAAGATGGGACT    2070
sPheAspMetProHisAspIleValAlaSerGluAspGlyThr
         680                          690
GACTGAAAAAATGGAGCATCGGTCAGTTAAAAAGGCTGGCATT    2160
uThrGluLysMetGluHisArgSerValLysLysAlaGlyIle
         710                          720
GGAGAACAAACCCACCTCCTCAGAATTGCAGAAGATGCAAGAG    2250
lGluAsnLysProThrSerSerGluLeuGlnLysMetGlnGlu
         740                          750
CATTACAACCCTTCTGGTTATTCCTGTGCTGGTCCTGCTGGCC    2340
uIleThrThrLeuLeuValIleProValLeuValLeuLeuAla
         770                          780
GGGAAGCGGCGGCTTAAATCTGGGAAATTTCTTTGCAAGTCGA    2430
sGlySerGlyGlyLeuAsnLeuGlyAsnPhePheAlaSerArg
         800                          810
TGACCAAGAGAAAGATGAGGACGACGGAAGTGAGTCTGAAGAG    2520
rAspGlnGluLysAspGluAspAspGlySerGluSerGluGlu
         830                          840
AGCCTTCGCCCGGGTAGCTGGACTGAGGTTTACCAGGATGCCC    2610

AAACTGTACTCGTCAGTGTGGGACTGTACACACCTTATTTACT    2700
CAGTTCACTCCAGTGCCATTGTCTTTATATGAACTTAGCGTAG    2790
GTTAGCTCATTCACATTTGGAGACGTTTTAGTTGGTGGATGT    2880
CCATCGCCAGTGTCTTTCTTTGGTGCCTTTCCTGTTCAGCATT    2970
CTGCTAAATCTCCTTCTATTTTTTAAAATCACTAACATTATA    3060
AAATTTCTCCTCAGTTGGTGTGTTTCCGGGATGTCTTATTTTT    3150
TTGTGTAATAAAGTGTTTTCAGAGCATT                   3225
```

Fig. 6(G)

[Region A]　(315bp)

GTGATTTCTATTCACTGCTTTCCAAGCTGCTAGGAGAAAGGGAAGATGTT
GlyAspPheTyrSerLeuLeuSerLysLeuLeuGlyGluArgGluAspVal

GGGTCAGACCTGGTAGCTGAGATTGCAAACGTGGTCCAGAAAAAGGACCTT
GlySerAspLeuValAlaGluIleAlaAsnValValGln<u>LysLys</u>AspLeu

TGGGGTAATGCTATCCTAGTCAGAGACAGGATCCACAGATTCCACCAGCTA
TrpGlyAsnAlaIleLeuValArgAspArgIleHisArgPheHisGlnLeu

TTCCAGCAGCCTGGCGAAGGCCCTTGGGAACCAGAACCCTCAGGAG
PheGlnGlnProGlyGluGlyProTrpGluProGluProSerGly

[Region C]　(54bp)

ATCATGACCGCAAGCTCGAGTCAAGTTCTGGAAGAGTCCTGGGAAGATTC
AspHisAspArgLysLeuGluSerSerSerGlyArgValLeuGlyArgPhe

Fig. 6(H)

```
CATGTGCACAAGTATAATCCTACAGAAAAGACAGAATCT
HisValHisLysTyrAsnProThrGluLysThrGluSer

GGTCGGTCTGACGCCAGAGAAGGTGCAGAGCATGAGGAA
GlyArgSerAspAlaArgGluGlyAlaGluHisGluGlu

GAGTCAACTCTGAGGCCAGCTGAGAGCAGAGCTTTCTCG
GluSerThrLeuArgProAlaGluSerArgAlaPheSer

CGAC
Arg
```

Fig. 13(A)

```
          10        20        30        40
       CGGCGTGGACATGGCTGGCCTTCGTAGCCTGCTAGTTCTC
              M   A   G   L   R   S   L   L   V   L 120       130       140       150
       CTACCAGACCATTTTCCAATGAATGTCTTGGTACCACCAG
        T   R   P   F   S   N   E   C   L   G   T   T   R 230       240       250       260
       TCTGATACATACTTCTGCATGTCGATGCGTTTGCCAATGG
        S   D   T   Y   F   C   M   S   M   R   L   P   M   D 340       350       360       370
       TGGTTGCAATATGCCCTCATCCACTGGAAGTTACTGGTTT
          G   C   N   M   P   S   S   T   G   S   Y   W   F 450       460       470       480
       GACTCCCCAAAGGTGTTGGATTCAGAGTTGGAGGAGAGAC
        L   P   K   G   V   G   F   R   V   G   G   E   T 560       570       580       590
       TGTTCTGGTGTGTCCTTACACCTCACACGCCTGCCACAGC
        C   S   G   V   S   L   H   L   T   R   L   P   Q   P 670       680       690       700
       TTCTGACCTTTCATGCCATTATAAAAAGTACCCAATGCAT
        S   D   L   S   C   H   Y   K   K   Y   P   M   H
```

Fig. 13(B)

```
              50            60            70            80
         CTCCTTGTTTTTCAGAGCAGCTGTTTGGGTTTCAGAAGCC
          L  L  V  F  Q  S  S  C  L  G  F  R  S  P 160           170           180           190
         ACCAGTCATTCCTATTGATTCATCAGATTTTGCATTGGAT
          P  V  I  P  I  D  S  S  D  F  A  L  D 270           280           290           300
         ATGAGGAAACCTTCGTGATTGACTTCAAACCTCGTGCCAG
          E  E  T  F  V  I  D  F  K  P  R  A  S 380           390           400           410
         TGTGATGAAGGCGTCTGTACAGACAAAGCCAATATTCTCT
          C  D  E  G  V  C  T  D  K  A  N  I  L  Y 490           500           510           520
         TGGAAGTAAATACTTCGTACTACAAGTACACTATGGGGAT
          G  S  K  Y  F  V  L  Q  V  H  Y  G  D 600           610           620           630
         CTTTAATTGCTGGCATGTACCTTATGATGGCTCTTGACAC
          L  I  A  G  M  Y  L  M  M  A  L  D  T 710           720           730           740
         GTCTTTGCCTATAGAGTTCACACTCACCATTTAGGTAAGG
          V  F  A  Y  R  V  H  T  H  H  L  G  K  V
```

Fig. 13(C)

```
         90            100           110
CACTTTCTGTCTTTAAGAGGTTTAAAGAAA
  L   S   V   F   K   R   F   K   E   T 200           210           220
ATTCGCATGCCTGGAGTCACACCTAAACAG
  I   R   M   P   G   V   T   P   K   Q 310           320           330
CATGGATACTGTCCATCATATGTTACTTTT
  M   D   T   V   H   H   M   L   L   F 420           430           440
ATGCCTGGGCAAGAAATGCTCCCCCCACCA
  A   W   A   R   N   A   P   P   T   R 530           540           550
ATTAGTGCTTTTAGAGATAATCACAAGGAC
  I   S   A   F   R   D   N   H   K   D 640           650           660
TGTTATACCAGCAGGAGAGAAAGTGGTGAA
  V   I   P   A   G   E   K   V   V   N 750           760           770
TAGTAAGTGGCTACAGAGTAAGAAATGGAC
  V   S   G   Y   R   V   R   N   G   Q
```

Fig. 13(D)

```
            780         790         800         810
        AGTGGACACTGATTGGACGTCAGAGCCCCCAGCTGCCACA
          W  T  L  I  G  R  Q  S  P  Q  L  P  Q 890         900         910         920
        ACTGGTGAAGGAAGGACAGAAGCCACGCACATTGGTGGCA
          T  G  E  G  R  T  E  A  T  H  I  G  G  T 1000        1010        1020        1030
        GACCTGTACCCAGAATGTAGCTCCAGAAATGTTCAGAACC
          T  C  T  Q  N  V  A  P  E  M  F  R  T 1110        1120        1130        1140
        AAACAGAGAACAAAGATAAGACTTCACTACAACAGCCAAA
          T  E  N  K  D  K  T  S  L  Q  Q  P  K 1220        1230        1240        1250
        GATGTTGTTCATGTGCATAAATATAACCCTACAGAAAAGG
          D  V  V  H  V  H  K  Y  N  P  T  E  K  A 1330        1340        1350        1360
        TGCCAGAGAGAGTGCAGAGCATGAGGACAGGGGCAATGCT
          A  R  E  S  A  E  H  E  D  R  G  N  A 1440        1450        1460        1470
        TTATCTCAGTACCGCAGCCCCTACCTGGTGAAGGCACCTG
           I  S  V  P  Q  P  L  P  G  E  G  T  W
```

Fig. 13(E)

```
       820         830         840         850
GGCTTTCTACCCTGTGGAACACCCAGTAGATGTCAGTTTT
  A  F  Y  P  V  E  H  P  V  D  V  S  F 930         940         950         960
CATCTAGTGATGAAATGTGCAACTTATACATTATGTATTA
  S  S  D  E  M  C  N  L  Y  I  M  Y  Y 1040        1050        1060        1070
ATCCCCCCAGAGGCCAATATTCCAATTCCTGTGAAGTCCG
  I  P  P  E  A  N  I  P  I  P  V  K  S  D 1150        1160        1170        1180
ACAAGAAGAAGAAGTGTTAGAACAGGGTGATTTCTATTCA
  Q  E  E  E  V  L  E  Q  G  D  F  Y  S 1260        1270        1280        1290
CAGAATCAGAGTCAGACCTGGTAGCTGAGATTGCAAATGT
  E  S  E  S  D  L  V  A  E  I  A  N  V 1370        1380        1390        1400
ATTCTTGTCAGAGACAGAATTCACAAATTCCACAGACTAG
  I  L  V  R  D  R  I  H  K  F  H  R  L  E 1480        1490        1500        1510
GGAACCAGAACACACAGGAGATTTCCATGTAGAAGAGGCA
  E  P  E  H  T  G  D  F  H  V  E  E  A
```

Fig. 13(F)

```
         860       870       880
GGTGACATACTGGCAGCAAGATGTGTGTTC
 G   D   I   L   A   A   R   C   V   F 970       980       990
CATGGAAGCCAAGCACGCAGTTTCTTTCAT
 M   E   A   K   H   A   V   S   F   M 1080      1090      1100
ACATGGTTATGATGCATGGACATCACAAAG
 M   V   M   M   H   G   H   H   K   E 1190      1200      1210
CTGCTTTCCAAGCTGCTAGGAGAAAGGGAA
 L   L   S   K   L   L   G   E   R   E 1300      1310      1320
AGTCCAAAAGAAGGATCTCGGTCGATCTGA
 V   Q   K   K   D   L   G   R   S   D 1410      1420      1430
AATCTACTTTGAGGCCAACAGAGAGCAGAG
   S   T   L   R   P   T   E   S   R   V 1520      1530      1540
CTGGATTGGCCTGGAGTATACTTGTTACCA
 L   D   W   P   G   V   Y   L   L   P
```

Fig. 13(G)

```
          1550          1560          1570          1580
      GGCCAGGTTTCTGGGGTAGCTCTGGACCTTCAGAATAACC
       G   Q   V   S   G   V   A   L   D   L   Q   N   N   L 1660          1670          1680          1690
      AAGAGGACTCGGGCCAATTGAAGAAGATACTATTCTTGTC
       R   G   L   G   P   I   E   E   D   T   I   L   V 1770          1780          1790          1800
      GCATAGACAAAGATGGAAATTATTGGGTCACAGACGTGGC
       I   D   K   D   G   N   Y   W   V   T   D   V   A 2000          2010          2020          2030
      ACTGGAAGGTTCATCACACAGTGGGGAGAAGAGTCTTCTG
       G   R   F   I   T   Q   W   G   E   E   S   S   E 2110          2120          2130          2140
      ATGTGTGGCCGACCGGGAAAATGGTCGGATCCAGTGTTTT
       C   V   A   D   R   E   N   G   R   I   Q   C   F 2220          2230          2240          2250
      CGTATATACCAGGTTTGCTCTTTGCCGTAAATGGGAAGCC
       Y   I   P   G   L   L   F   A   V   N   G   K   P 2330          2340          2350          2360
      TTCAAGCCAGTGCGCAAGCACTTTGACATGCCTCATGACA
       F   K   P   V   R   K   H   F   D   M   P   H   D   I
```

Fig. 13(H)

```
           1590          1600          1610          1620
         TGGTGATTTTCCACAGAGGTGACCATGTCTGGGATGGAAA
           V  I  F  H  R  G  D  H  V  W  D  G  N 1700          1710          1720          1730
         ATAGATCCAAATAATGCTGCAGTCCTCCAGTCCAGTGGAA
           I  D  P  N  N  A  A  V  L  Q  S  S  G  K 1930          1940          1950          1960
         AGATCCAAACACTGGGACCATCTTTGTATCAGATGGTTAC
           D  P  N  T  G  T  I  F  V  S  D  G  Y 2040          2050          2060          2070
         AGAGCAATCCTAAACCAGGCCAGTTCAGGGTTCCTCACAG
           S  N  P  K  P  G  Q  F  R  V  P  H  S 2150          2160          2170          2180
         AAAACTGACACCAAAGAATTTGTGCGAGAGATTAAGCATG
           K  T  D  T  K  E  F  V  R  E  I  K  H  A 2260          2270          2280          2290
         TTACTTTGGGGACCAAAAACCAGTACAAGGATTTGTGATG
           Y  F  G  D  Q  K  P  V  Q  G  F  V  M 2370          2380          2390          2400
         TTACTGCATCTGAAGACGGGACTGTGTATGTTGGAGATGC
           T  A  S  E  D  G  T  V  Y  V  G  D  A
```

Fig. 13(1)

```
        1630        1640        1650
CTCTTTTGACAGCAAGTTTGTGTACCAGCA
  S   F   D   S   K   F   V   Y   Q   Q 1740        1750        1760
AAAATCTGTTTTACTTGCCACATGGCTTGA
  N   L   F   Y   L   P   H   G   L   S 1970        1980        1990
TGCAACAGTCGGATCGTGCAGTTTTCACCA
  C   N   S   R   I   V   Q   F   S   P   T 2080        2090        2100
CTTGGCCCTTGTGCCTCATTTGGGCCAATT
  L   A   L   V   P   H   L   G   Q   L 2190        2200        2210
CATCATTTGGAAGAAATGTATTTGCAATTT
  S   F   G   R   N   V   F   A   I   S 2300        2310        2320
AACTTTTCCAGTGGGGAAATTATAGATGTC
  N   F   S   S   G   E   I   I   D   V 2410        2420        2430
TCACACCAACACCGTGTGGAAGTTCACTTC
  H   T   N   T   V   W   K   F   T   S
```

Fig. 13(J)

```
      2440           2450           2460           2470
GACTGAA|ACAGCCCAGGTCTGGTTCCCGGGTGTGGACCTA
  T  E |T  A  Q  V  W  F  P  G  V  D  L 2550           2560           2570           2580
ATCTCAGGGCCAATCTTCCTCAGCAAATGAAAAAAAA|AG
  L  R  A  N  L  P  Q  Q  M  K  K  K |R 2660           2670           2680           2690
GAAACCAAAATGGAGAACAAACCCGCCTCCTCAGAATTGC
  E  T  K  M  E  N  K  P  A  S  S  E  L  Q 2770           2780           2790           2800
CCTTCTGGTTATTCCGGTGGTTGTCCTGCTGGCCATTGCC
  L  L  V  I  P  V  V  V  L  L  A  I  A 2880           2890           2900           2910
GAGTACTGGGAAGACTTAGAGGAAAAGGAAGTGGAGGCTT
  V  L  G  R  L  R  G  K  G  S  G  G  L
```

Fig. 13(K)

```
       2480        2490        2500        2510
CATCACTCGTCAGTGGCCATGCTGTGGTGGCAGCTCACAT
 H  H  S  S  V  A  M  L  W  W  Q  L  T  Y 2590        2600        2610        2620
AGTGGAGCATCGATCAGTTAAAAAGGCTGGCATTGAGGTC
 V  E  H  R  S  V  K  K  A  G  I  E  V 2700        2710        2720        2730
AGAAGATGCAAGAGAAACAGAAACTGATCAAAGAGCCAGG
 K  M  Q  E  K  Q  K  L  I  K  E  P  G 2810        2820        2830        2840
ATATTTATTCGGTGGAAAAAATCAAGGGCCTTTGGAGAGT
 I  F  I  R  W  K  K  S  R  A  F  G  E  S 2920        2930        2940        2950
AAACCTCGGAAATTTCTTTGCGAGCCGTAAAGGCTACAGT
 N  L  G  N  F  F  A  S  R  K  G  Y  S
```

Fig. 13(L)

```
         2520        2530        2540
     ACAAAAAGAGGAAGATTGACAACAGATGTT
       K  K  R  K  I  D  N  R  C  Y 2630   (C)  2640        2650
     CAGGAAATCAAAGAATCCGAGGCAGTTGTT
       Q  E  I  K  E  S  E  A  V  V 2740        2750        2760
     CTCGGGAGTGCCCGTTGTTCTCATTACAAC
       S  G  V  P  V  V  L  I  T  T 2850        2860        2870
     CTGAACACAAAGTCGAGGCAAGTTCAGGAA
       E  H  K  V  E  A  S  S  G  R 2960        2970        2980
     CGGAAAGGGTTTGACCGGCTCAGCACCGAG
       R  K  G  F  D  R  L  S  T  E
```

Fig. 13(M)

```
           2990        3000        3010        3020
          GGGAGTGACCAGGAGAAAGATGAGGATGACGGAAGTGAAT
           G   S   D   Q   E   K   D   E   D   D   G   S   E   S 3100        3110        3120        3130
          AGTTGATGAGATTACCAAGAATGCCAGGTTCCTTTCCCT 3210        3220        3230        3240
          TTTACTTCGTTTTGGTTTAGTTGGCTTCTGTTTCTGGTTG 3320        3330        3340        3350
          TCTTCCATCACGTTACTAATTTAATGATGGAAGCTTTGCT 3430        3440        3450        3460
          ATAGCACTTCCATTGCCAGTGTCTTTCTTTGGTGCCTTTC 3540        3550        3560        3570
          TTCTTCTATTTTTTAAAATCACTAACATTATATTGCAAC 3650        3660        3670        3680
          GATGTCTTATTTTAGATGGTTACACTGTTAGAACACTAT
```

Fig. 13(N)

```
       3030        3040        3050        3060
CAGAAGAAGAATATTCAGCACCTCTGCCCGCACCTGTACC
  E   E   E   Y   S   A   P   L   P   A   P   V   P 3140        3150        3160        3170
TTAGCACGATTAGAGTTTTGTGTATTTAATTGTAAACTGT 3250        3260        3270        3280
AGGAGTTTCCTAAAAGTTCATAACAGTGCCATTGTCTTTA 3360        3370        3380        3390
CATTTACATTTTGAGACTTTTCTGTAGGTGTAAATAGCCC 3470        3480        3490        3500
CTGTTCAGCATTCTCAGCCTGTGGCAGTAAAGAGAAACTT 3580        3590        3600        3610
AAGGGAAAGAAAAAAGTCTCTATTTAAATTCTTTTTTTA 3690        3700        3710        3720
TTTCAGAATCTGAATGTAATTTGTGTAATAAAGTGTTTTC
```

Fig. 13(O)

```
        3070         3080         3090
TTCCTCCTCCTGAAAACTGGGCTTTGATTT
  S    S   S 3180         3190         3200
ACTAGTCTGTGTGGGACTGTACACATTTTA 3290         3300         3310
TCTGAACATAGAATAGAGAAACAGTCCTCT 3400         3410         3420
CATTCTCTGCTTGGACACAGTCTTTTCCCA 3510         3520         3530
TGTGCTACACGACGACGAAGCTGCTAAATC 3620         3630         3640
AATTTTCTTCTTTAGTTGGTGTGTTTTGG 3730         3740         3750
AGAGCATTAGCTGTCAGAGTGTATTTTGCC
```

Fig. 13(P)

```
      3760      3770      3780      3790      3800
AATTTTTGCATATGTCCAGGGTTTTGTATACTTTTGTAATAATTACATAAACCACA 3870      3880      3890      3900      3910
TTAAAATCAAGAAGATATTTTGTTATGTAGCTGATACAAATTAAAACCAGCCTAA 3980      3990      4000      4010      4020
GCCTGTATATCAATCAGAAGGTAAATACTTGAATAAAAGGTGATCATAGCTGAGAG 3810      3820      3830      3840      3850      3860
GATTGAGTGAAACCTACTCAATGTCTTCAACCAAAGAAATGTGTTGTATTGTA 3920      3930      3940      3950      3960      3970
GAGCTTACATACATGTGTAAAATCAGGCTCTCTGATGATTCAACGAGAGTGTTT 4030      4040
GAAAAAAAAAAAAAAAA
```

Fig. 14(A)

```
         10           20           30           40
ATGGCCGGACGCGCCCGCAGCGGTCTGCTACTGCTGCTGC 120          130          140          150
AGAAACTACCAGATCATTTTCCAATGAATGCCTTGGTACC 230          240          250          260
AAGAGTCTGACACATACTTCTGCATGTCCATGCGTCTGCC 340          350          360          370
CTGTTTGGATGCAATATGCCCTCGTCCACTGGAAGTTACT 450          460          470          480
CACCCGGCTCCCGAAAGGTGTTGGATTCAGAGTTGGAGGA 560          570          580          590
AAGACTGCTCTGGCGTGTCCGTACATCTCACACGTGTGCC
```

Fig. 14(B)

```
          50            60            70            80
     TGGGGCTGCTCGCCCTGCAGACCAGCTGCCTGGCCTTCAG 160           170           180           190
     ATTGGACCAGTCACCCTCTTGATGCATCAGATTTTGCGC 270           280           290           300
     TGTGGATGAGGAAGCCTTCGTGATTGACTTCAAGCCTCGT 380           390           400           410
     GGTTTTGTGATGAAGGAACCTGTACAGATAAAGCCAATAT 490           500           510           520
     GAAACTGGAAGCAAATACTTCGTCCTTCAAGTTCACTATG 600           610           620           630
     CCAGCCTTTAATTGCGGGCATGTACCTTATGATGTCTGTT
```

Fig. 14(C)

```
         90        100        110
    AAGCCCACTTTCTGTCTTTAAGAGGTTTAA 200        210        220
    TGGATATTCGCATGCCTGGGGTTACACCTA 310        320        330
    GCCAGCATGGATACTGTCCACCATATGCTG 420        430        440
    TCTATATGCCTGGGCAAGGAATGCTCCCCC 530        540        550
    GCGATATCAGTGCTTTTCGAGATAATCACA
```

Fig. 15(A)

```
         10          20          30          40
TGCATGTGTTTGCCTACAGAGTCCACACTCACCATTTAGG 120         130         140         150
CCACAGGCTTTCTACCCTGTGGAACACCCCGTTGATGTTA 230         240         250         260
CGGCACTTCTAGTGACGAAATGTGTAACCTGTACATCATG 340         350         360         370
GAACTATCCAGCAGAGGCCAATATCCCAATTCCTGTCAA 450         460         470         480
CAGCCAAAACAGGGAGAGGAAGAAGTATTAGAGCAGGGTG 560         570         580         590
AGAAAAGACAGAATCTGGGTCAGACCTGGTAGCTGAGATT
```

Fig. 15(B)

```
           50         60         70         80
       TAAGGTGGTGAGCGGATACAGAGTAAGAAACGGACAGTGG 160        170        180        190
       CTTTTGGTGATATACTGGCAGCCAGATGTGTGTTCACTGG 270        280        290        300
       TATTACATGGAAGCCAAATATGCACTTTCCTTCATGACCT 380        390        400        410
       ACCGGACATGGTTATGATGCACGGGCATCACAAAGAAGCA 490        500        510        520
       ATTTCTATTCACTGCTTTCCAAGCTGCTAGGAGAAAGGGA 600        610        620        630
       GCAAACGTGGTCCAGAAAAGGACCTTGGTCGGTCTGACG
```

Fig. 15(C)

```
          90        100        110
    ACACTGATTGGACGCCAGAACCCCCAGCTG 200        210        220
    TGAAGGGAGGACAGAGGCCACCCATATCGG 310        320        330
    GTACAAAGAACGTGGCTCCAGATATGTTCA 420        430        440
    GAAAACAAAGAAAAGAGTGCTTTAATGCAG 530        540        550
    AGATGTTCATGTGCACAAGTATAATCCTAC 640        650        660
    CCAGAGAAGGTGCAGAGCATGAGGAATGGG
```

Fig. 15(D)

```
              670          680          690          700
         GTAATGCTATCCTAGTCAGAGACAGGATCCACAGATTCCA 780          790          800          810
         TGGGAACCAGAACCCTCAGGAGATTTCCATGTGGAAGAAG 890          900          910          920
         CCTAGTGATTTTCCACAGAGGTGACCATGTTTGGGATGGA 1000         1010         1020         1030
         TCATTGACCCAAATAATGCTGAAATCCTCCAGTCCAGTGG 1110         1120         1130         1140
         GCTCTCCACCAGGTGTTCAAATTGGACCCGCATAGCAAAG
```

Fig. 15(E)

```
      710       720       730       740
CCAGCTAGAGTCAACTCTGAGGCCAGCTGAGAGCAGAGCT 820       830       840       850
AACTGGACTGGCCTGGAGTGTACTTGTTACCAGGCCAGGT 930       940       950       960
AACTCTTTTGACAGCAAGTTTGTTTACCAGCAAAGAGGTC 1040      1050      1060      1070
CAAGAACCTGTTTTATTTACCACACGGCTTGAGCATAGAT 1150      1160      1170
AAGGCCCTCTCTTAATTCTGGGAAGGAGCATG
```

Fig. 15(F)

```
         750        760        770
TTCTCGTTCCAGCAGCCTGGCGAAGGCCCT 860        870        880
TTCTGGGGTGGCCCTGGATTCTAAGAATAA 970        980        990
TTGGGCCAATTGAAGAAGACACCATCCTGG 1080       1090       1100
ACAGATGGAAATTATTGGGTCACAGATGTG
```

PURIFIED ENZYMES PARTICIPATING IN C-TERMINAL AMIDATION

This application is a 371 of Application No. PCT/JP90/01036, filed Aug. 14, 1990.

TECHNICAL FIELD

This invention relates to a novel enzyme participating in a C-terminal amidation of a peptide C-terminal glycine adduct, a method of preparing same, and the use thereof. The term "participating in a C-terminal amidation" as used herein means possessing an action promoting any step for converting a peptide C-terminal glycine adduct into its peptide C-terminal amidated compound.

BACKGROUND ART

In the past, the enzyme participating in the enzymatic reaction in vivo, i.e., a C-terminal amidation of a C-terminal glycine adduct of peptides (compound in which glycine is peptide-bonded to C-terminal residue) is called peptidylglycine-α-amidating monooxygenase (C-terminal amidating enzyme) (EC.1.14.17.3) (Bradbury et. al., Nature, 298, 686, 1982: Glembotski et. al., J. Biol. Chem., 259. 6385, 1984), and is considered to catalyze the following reaction:

To clarify the amidation mechanism in vivo and utilize the enzyme for the method of converting the peptides which exhibit a physilogical activity for the first time by an amidation of the C-terminal with the peptide produced by the recombinant DNA technique, for example, calcitonin and gastrin, in vitro, attempts have been made to purify this enzyme. For example, there have been reported those derived from bovine pituitary gland middle lobe (Murthy et. al., J. Biol. Chem., 261, 1815, 1986), porcine pituitary gland (Kizer et. al., Endocrinology, 118, 2262, 1986; Bradbury et. al., Eur. J. Biochem., 169, 579, 1987), porcine heart atrium (Kojima et. al., J. Biochem., 105, 440, 1989), Xenopus body skin (Mizuno et. al., Biochem., Biophys. Res. Commun., 137, 984, 1986), rat thyroid gland tumor (Mehta et. al., Arch. Biochem., Biophys., 261, 44, 1988).

On the other hand, since it is difficult to procure a large amount of these purified enzymes, attempts have been made to isolate the cDNA's necessary for expression of these enzymes by use of the recombinant DNA technique generally practiced in recent years, and the production of the enzymes by utilizing same. For example, Eipper B. A, et. al. in Mol. Endocrinol. 1, 777–790, 1987, Ohsuye K. et. al. in Biochem. Biophys. Res. Commun., 150, 1275–1281, 1988, Stoffers, D. A. et. al. in Proc. Natl. Acad. Sci., USA, 86, 735–739, 1989, and Glauder, J. et. al. in Biochem. Biophys. Res. Commun., 169, 551–558, 1990, have reported peptide C-terminal amidating enzyme cDNA's derived from bovine pituitary gland, frog skin, rat atrium and human thyroid gland cell, respectively. Further, although not necessarily having a satisfactory productivity, there are also known examples of peptide C-terminal amidating enzymes produced by using of the recombinant DNA technique utilizing the cDNA derived from frog and bovine (e.g., see Japanese Unexamined Patent Publication (Kokai) No. 1-104168, Published International Application: WO89/02460, and Perkins et. al., Mol. Endocrinol., 4, 132–139, 1990).

On the other hand, these proteins have been reported to have molecular weights of 38, 42 or 54 kDa in bovine, 39 kDa in frog, and 41, 50, or 75 kDa in rat, which are very different from each other, depending on the collecting methods, etc. For example, the literature of Bradbury et. al., described above, Ramer et. al., 110, 8526–8532 (1988) and Young et. al., J. Am. Chem. Soc. 111, 1933–1934 (1989) suggest the existence of reaction intermediatesm, but there are no current examples which clarify the isolation of an intermediate, and the relationship between the intermediate and the amidating enzyme.

As described above, the peptide C-terminal amidating enzyme exhibits a very interesting action in vivo, and a composition having a constant purity derived from a specific living body organ is known. Nevertheless, these compositions cannot be used for the production of a peptide C-terminal amidated compound in vivo, as the purity and stability as well as to production costs thereof are not satisfactory. To solve these problems, on the premise that it is necessary to collect basic knowledge concerning the enzyme, i.e., clarify the reaction mechanism when carrying out the C-terminal amidation reaction, the present inventors attempted to isolate the intermediate product, and consequently successfully isolated the intermediate and determined the structure thereof. From this result it was found that the enzymatic active substance called the C-terminal amidating enzyme of the prior art is not a one-step reaction as considered in the prior art, but is a two-step reaction through the intermediate (corresponding to C-terminal α-hydroxylglycine adduct).

Since it is predicted that an efficient conversion of a peptide C-terminal glycine adduct into the corresponding amidated compound can be carried out by the single or combined use of enzymes catalyzing the respective reaction under adequate conditions, it will become necessary to provide these enzymes. Further, where the existence of these enzymes can be confirmed, it will become necessary to provide an efficient method of preparing same.

DISCLOSURE OF THE INVENTION

According to the present invention, there are provided an enzyme participating in a C-terminal amidation which acts on a C-terminal glycine adduct represented by the following formula (I):

(wherein A represents a residue other than α-amino group or imino group and α-carboxylic group derived from naturally occurring α-amino acid, X represents a hydrogen atom or a residue of an amino acid derivative which is bonded to an N atom through a carbonyl group) to form a C-terminal α-hydroxylglycine adduct represented by the following formula (II):

(wherein A and X have the same meanings as above, hereinafter sometimes called "Enzyme-I"), and an enzyme participating in a C-terminal amidation of a C-terminal glycine adduct which acts on a C-terminal α-hydroxylglycine adduct represented by the above formula (II) to form a C-terminal amidated compound represented by the following formula (III):

(wherein A and X have the same meanings as above) (hereinafter sometimes called "Enzyme-II").

In the formulae (I), (II), and the formula (III), the hydrogen atom in the bracket (H) means no hydrogen atom exists when A is derived from an α-amino acid having an α-imino group.

By using each of these enzymes or a combination thereof, the peptide C-terminal glycine adduct represented by the formula (I) can be efficiently converted into the corresponding peptide C-terminal amidated compound represented by the formula (III).

According to the present invention, there are also provided a method of producing these enzymes from the above-mentioned enzyme activity-containing compound, by the use of a specific ligand, and a method of efficiently producing these enzymes by the use of a cDNA coding these enzyme activity-containing peptides.

Further, according to present invention, there are provided a method of assaying the activity of the above-mentioned enzyme and a method of screening said enzyme-containing compounds.

Furthermore, according to the present invention, a cDNA encoding said enzyme activity derived from horse.

BRIEF DESCRIPTION OF THE DRAWINGS

In the description and drawings, letters which are used in an amino acid sequence by one letter mean those which are usually used in the art, and "hyG" means α-hydroxyglycine.

FIG. 4 shows an HPLC pattern over a lapse of time when preparing FGF-NH$_2$ by using the enzyme-II of the present invention with FGFhyG as the substrate;

FIGS. 5(A)–5(F) show the amino acid sequences estimated from the peptide C-terminal amidating enzyme cDNA's cloned from human, horse, bovine, rat, frog, as a one letter representation;

FIGS. 6(A)–6(H) show the nucleotide sequence of the C-terminal amidating enzyme cDNA cloned from the rat pituitary mRNA and the amino acid sequence estimated therefrom;

B (Bam HI), N (Nsi I), RI (EcoRI), RV (EcoRV), S (SPhI), X (XmaI).

Figure 8:
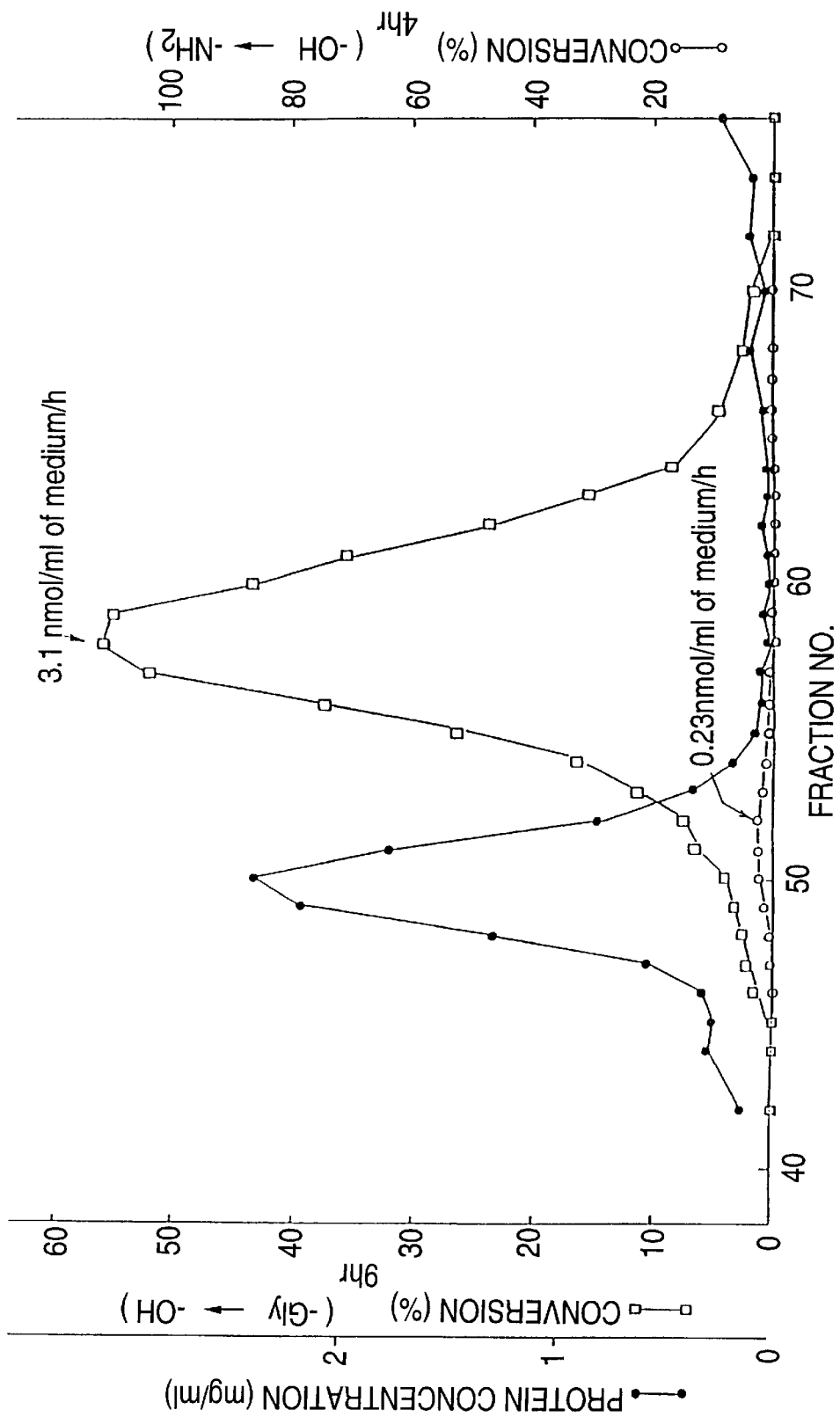
Figure 9:
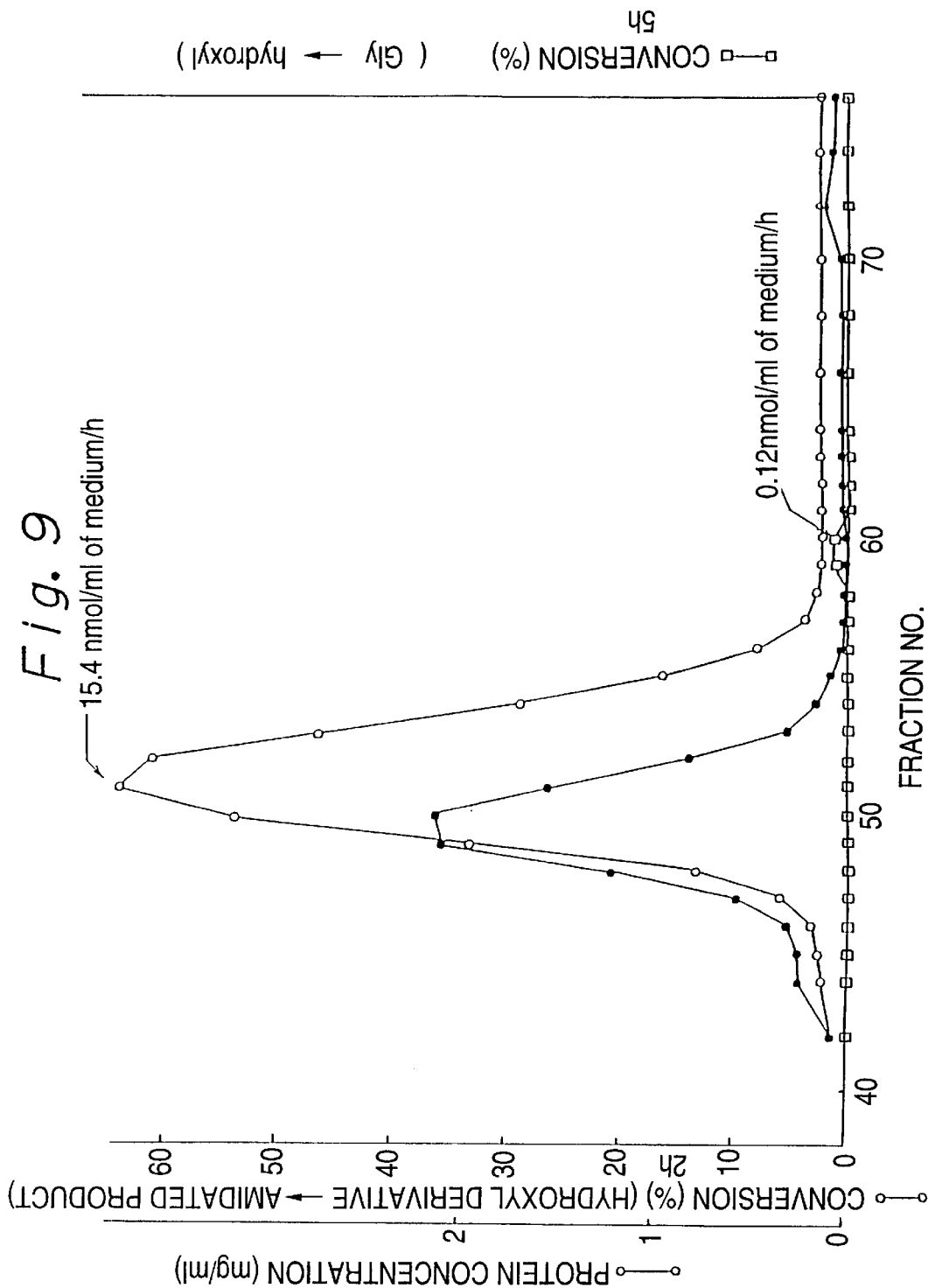
Figure 10:
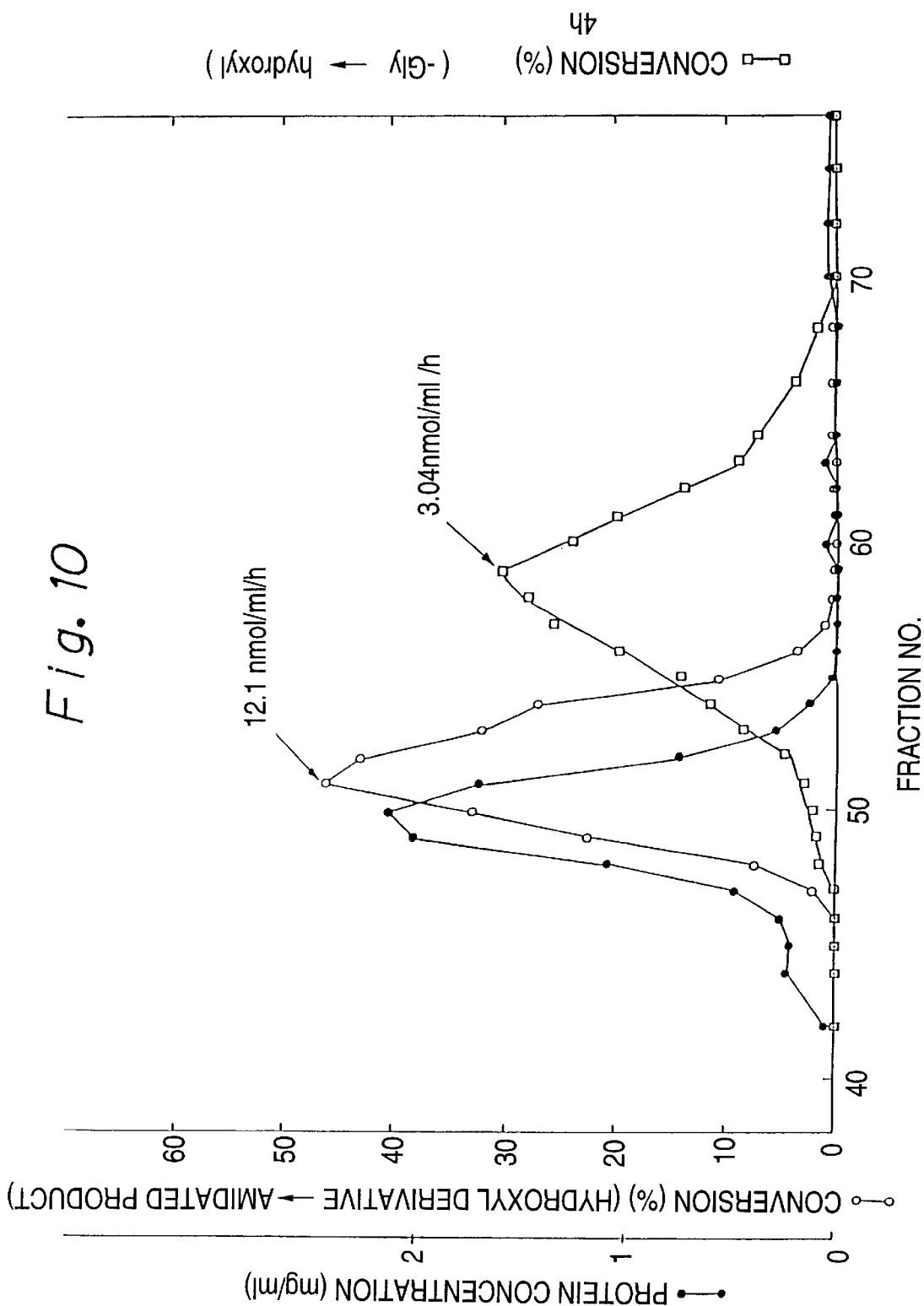
Figure 11:
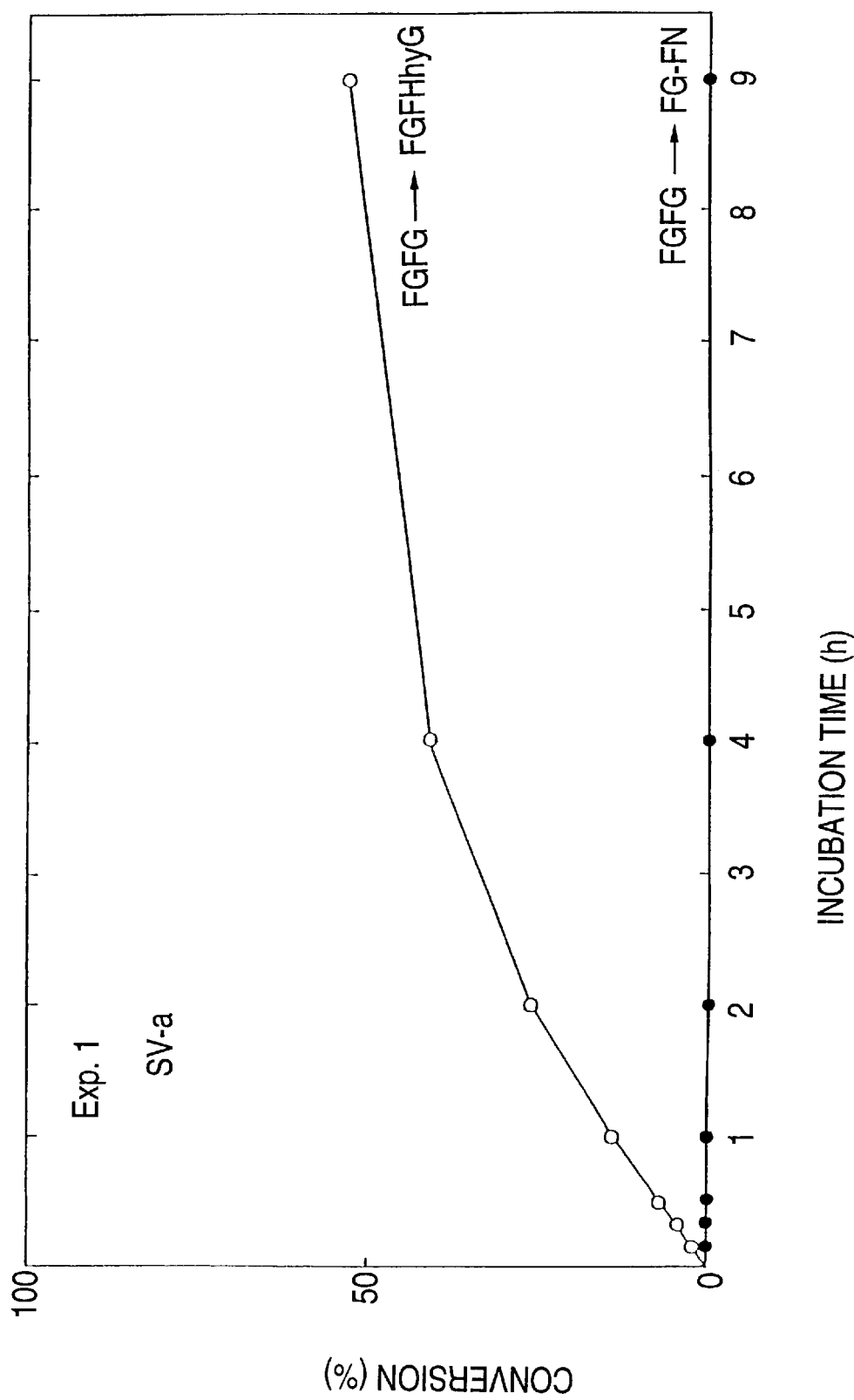
Figure 12:
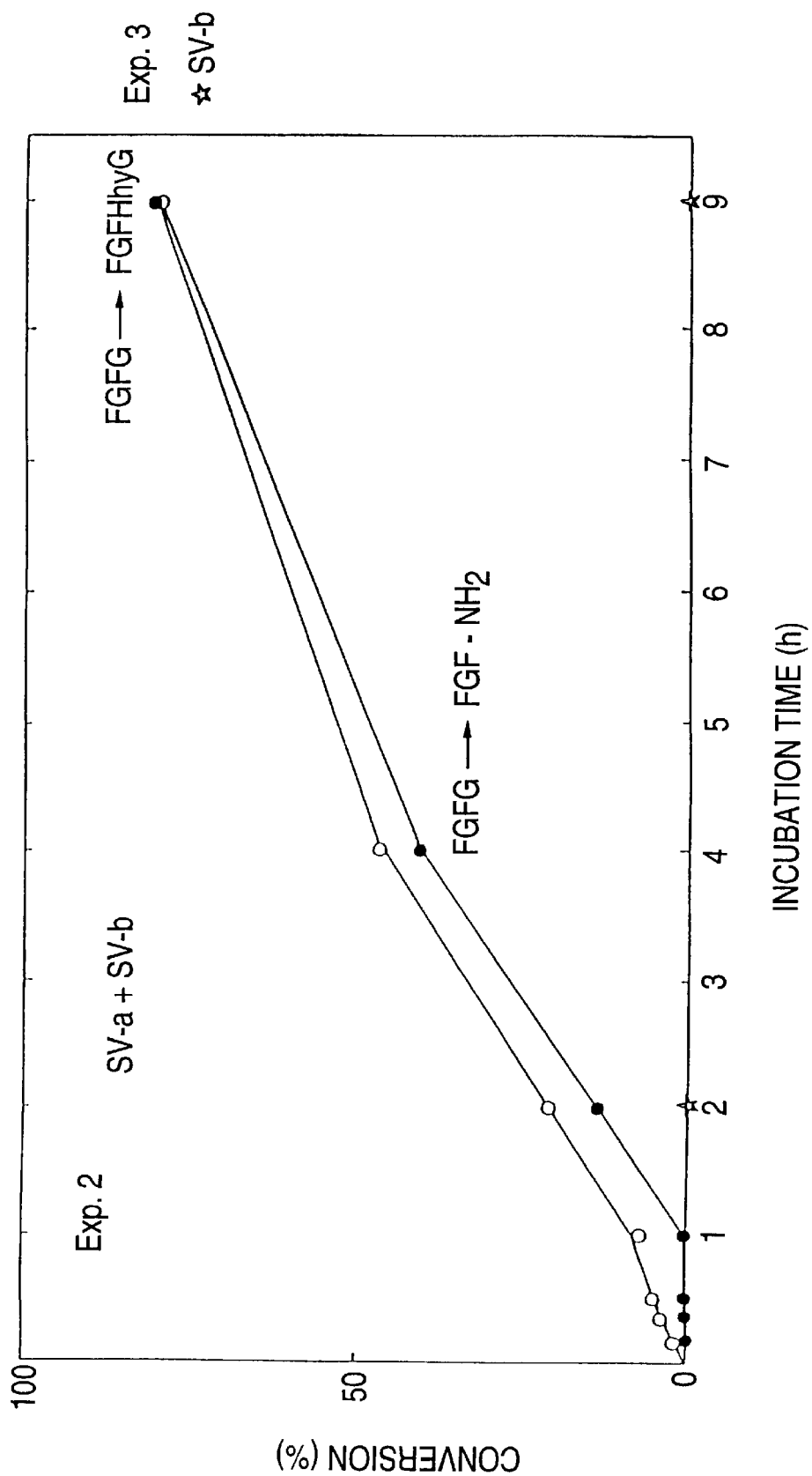

FIG. 8, FIG. 9, and FIG. 10 show the Sephacryl S-200 column chromatography patterns of the enzymes expressed by the plasmids SV-a, SV-b, SV-203, respectively;

FIG. 11 and FIG. 12 show the changes in production of the α-hydroxylglycine adduct, and the C-terminal amidated compound over a lapse of time when using PheGlyPheGly as the substrate;

FIGS. 13(A)–13(P) show the nucleotide sequence of the longest cDNA fragment among the cDNA's coding for the polypeptide having a peptide C-terminal amidating enzyme activity derived from isolated horse and the amino acid sequence coded for thereby as a one letter representation; and FIGS. 14(A)–FIGS. 14(C) and FIGS. 15(A)–15(F) respectively show a part of the base sequence of cDNA's coding for the peptide C-terminal amidating enzymes derived from rat used as the probe, which were digested with different restriction endonucleases, respectively.

BEST MODE OF CARRYING OUT THE INVENTION

The C-terminal glycine adduct represented by the formula (I) of the present invention, i.e., the substrate of the enzyme composition of the present invention, may generally include compounds derived from amino acid derivatives wherein the

moiety in the above formula is natural or synthetic, particularly the compounds derived from peptides or proteins, with glycine being bonded to the C-terminal acid residue thereof (represented by —N(H)—A—CO—). As the C-terminal amino acid residue, a residue derived from naturally occurring α-amino acid, particularly an amino acid constituting proteins, for example, an aliphatic amino acid such as glycine or alanine; branched amino acid such as valine, leucine or isoleucine; hydroxylated amino acid such as serine or threonine; acidic amino acid such as aspartic acid or glutamic acid; amide such as asparagine or glutamine; basic amino acid such as lysine, hydroxylysine, arginine; sulfur containing amino acid such as cysteine, cystine or methionine; aromatic amino acid such as phenylalanine or tyrosine; heterocyclic amino acid such as tryptophan or histidine; and imino acid such as proline or 4-hydroxyproline may be included. The hydrogen atom or the residue of the amino acid derivative bonded to the α-amino group or imino group of the amino acid residue (represented by X—) is not particularly limited with respect to the kind and chain length of the peptide of the constituent amino acid residue, provided that it is a peptide bonded through a single amino acid or α-amino group, and further, phosphoric acid, sugar or other substituent may be covalently bonded to the constituent amino acid residue and it may form a conjugate with a lipid. Specific examples of the above-mentioned substituents include, corresponding to the respective amino acid residues, the substituents on the guanidino group of arginine residue, for example, alkyl groups such as methyl, ethyl, etc., the residues derived from adenosine diphosphate ribose, citrulline or ornithine; substituents derived from ε-amino group of lysine residue, for example, the substituents derived from compounds having glycosyl group, pyridoxyl group, biotinyl group, lipoyl group, acetyl group, phosphoric acid or δ-hydroxyl group, compounds having δ-glycosyl group, residue derived from glutaraldehyde or citraconic anhydride, etc.; substituents on the imidazole group of hystidine residue, for example, methyl group, the substituents derived from phosphoric acid, iodine atom or flavin; substituents on proline residue, for example, hydroxyl group, dihydroxyl group, glycosyloxy group; substituents on the benzene ring of phenylalanine residue, for example, hydroxyl group or glycosyloxy group; substituents on the hydroxyl group of tyrosine residue, for example, glycosyloxy group, sulfonic acid group, iodine atom, bromine atom or chlorine atom, or a compound having hydroxyl group, bisether, adenine, residue derived from uridine or RNA (ribonucleic acid), etc.; substituents on the hydroxyl group of serine residue, for example, methyl group, glycosyl group, phosphopanteteic acid, adenosine diphosphoric acid ribosyl or phosphoric acid; substituents on the hydroxyl group of threonine residue, for example, glycosyl group, methyl group or phosphoric acid group; substituents on the SH group of cysteine residue, for example, glycosyl group, the substituents derived from cystinyl, dehydroalanyl group, selenium atom, or residue derived from heme or flavin; substituents on the carboxyl group of aspartic acid or glutamic acid residue, for example, methyl group, phosphoric acid group or γ-carboxyl group; substituents on asparagine or glutamine residue, for example, glycosyl group, pyrrolidonyl group or imino group, etc.

The peptide having glycine peptide bonded to the C-terminal residue as in the above substrate, or its derivative may be either naturally extracted or produced by chemical synthesis, or produced by a recombinant DNA technique. Therefore, as the substrate of the present invention, the compound represented by the formula (I) may include C-terminal glycine adducts (i.e., amide bonded compounds of C-terminal carboxyl group and glycine), for example, peptides with amino acid residues of about 2 to 100, phosphate peptides as represented by casein, protein kinase, adenovirus EIA protein, RAS 1 protein, etc. and hydrolyzates thereof, lipoproteins such as thromboplastin, α₁-lipoprotein, lipovitellin, etc. and hydrolyzates thereof, metal proteins as represented by hemoglobin, myoglobin, hemocyanin, chlorophyil, phycocyanin, flavin, rhodopsin, etc., and hydrolyzates thereof, glycoproteins as represented by collagen, laminin, interferon α, seroglycoide, avidin, etc., and hydrolyzates thereof, as well as other physiologically active peptides of the maturation type with amidated C-terminal carboxyl group, for example, calcitonin, secretin, gastrin, vasoactive intestinal peptide (VIP), cholecystokinin, caerulein, pancreatic polypeptide, growth hormone-releasing factor, corticotropin-releasing factor, calcitonin gene related peptide, etc. Of these, a preferable substrate for identifying the enzyme activity of the enzyme composition of the present invention includs D-tyrosyl-valyl-glycine, D-tyrosyl-tryptophanyl-glycine, glycyl-phenylalanyl-glycine, phenylalanyl-glycyl-phenylalanyl-glycine, D-tyrosyl-leucyl-asparaginyl-glycine, arginyl-phenylalanyl-arginyl-alanyl-arginyl-leusyl-glycine, leucyl-methionyl-glycine, glycyl-leucyl-methionyl-glycine, phenylalanyl-glycyl-leucyl-methionyl-glycine, asparaginyl-arginyl-phenylalanyl-glycine, tryptophanyl-asparaginyl-arginyl-phenylalanyl-glycine, alanyl-phenylalanyl-glycine, lysyl-alanyl-phenylalanyl-glycine, seryl-lysyl-alanyl-phenylalanyl-glycine, arginyl-tyrosyl-glycine, glycyl-methionyl-glycine, glycyl-tyrosyl-glycine, glycyl-histidyl-glycine, histidyl-glycyl-glycine, tryptophanyl-glycyl-glycine and glycyl-cysteinyl-glycine and the like (except for glycine, L-form is shown unless otherwise particularly noted as D-). On the other hand, a preferable substrate for effectively utilizing the present enzyme composition includs the peptides with glycine peptide bonded to the C-terminal carboxyl group thereof, which form a physiologically active peptide of the maturation type by amidation of the above-mentioned C-terminal carboxyl group.

Acting on the substrate as mentioned above, the enzyme-I of the present invention can form a C-terminal α-hydroxylglycine adduct represented by the following ormula (II):

(wherein specific examples of the

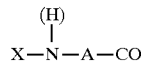

moiety have the meanings as defined for the above formula (I)).

The compound represented by the formula (II) can be converted by hydrolyzing under conditions whereby no deleterious influence is exerted on the moiety

or by treating with the second enzyme of the present invention, as described below, to be converted to the corresponding C-terminal amidated compound.

The above-mentioned enzyme-I has a molecular weight of about 25 kilo-dalton (kDa) in horse and of about 36 kDa in rat according to the molecular weight determination method by use of gel filtration. More specifically, the molecular weight can be measured according to the gel filtration method known per se (e.g., "Seikagaku Jikken Kouza 5, Enzyme Study Method, Former vol., p. 283–298", Tokyo Kogaku Dojin (1975)). Specifically by use of a 50 mM Tris-HCl (pH 7.4) containing 100 mM potassium chloride as the equilibration and eluting solution, gel filtration was effected on Toyopearl HW-55S (produced by Toso), and the molecular weight was determined with β-amylase (M.W. 200,000), alcohol dehydrogenase (M.W. 150,000), BSA (M.W. 66,000), carbonic anhydrolase (M.W. 29,000) and cytochrome C (M.W. 15,400) as the indices.

The enzyme-I of the present invention is further specified by the following physicochemical properties, namely:
 (a) the optimum pH is about 5 to 7 and the stable pH is 4 to 9;
 (b) the acting optimum temperature is from about 25° to 40° C.;
 (c) metal ions and ascorbic acid act as the cofactor.

The above properties (a) and (b) are measured by the use of conventional buffers, specifically, Tris-HCl, Mes-potassium hydroxide, Tes-sodium hydroxide, Hepes-potassium hydroxide buffers. The enzyme composition of the present invention can catalyze the above reaction within the temperature range of 1° C. to 55° C., but will be inactivated at 56° C. within about 10 minutes; a slight inactivation is also seen at around 40° C.

As the metal ion, $Cu^{2+}$, $Zn^{2+}$, $Ni^{2+}$, $Co^{2+}$, $Fe^{3+}$, etc. are suitable, but particularly preferably $Cu^{2+}$ and $Zn^{2+}$ are used.

The present invention further provides another kind of enzyme, as follows. More specifically, there is provided an enzyme participating in a C-terminal amidation of a C-terminal glycine adduct which acts on a C-terminal α-hydroxylglycine adduct represented by the above formula (II) to form a C-terminal amidated compound represented by the following formula (III):

(wherein A and X have the same meanings as defined above) and glyoxylic acid.

The molecular weight of this enzyme also depends on the origin thereof. When separated from the enzyme activity-containing compound described below, followed by purification, the enzyme-II is an enzyme participating in a C-terminal amidation of glycine adduct, which has a molecular weight of about 40 kDa when derived from horse, or about 43 kDa when derived from rat according to the molecular weight determination method by gel filtration. The molecular weight of the enzyme-II produced by utilizing cDNA is sometimes large and similar to the case of the enzyme-I. The significance and molecular weight determination of the moiety

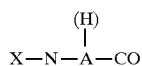

used for specifying this enzyme are the same as used for specifying the enzyme-I. As preferable substrates for identification of the enzyme activity of the enzyme-II, α-hydroxyglycine compounds corresponding to the substrates specifically enumerated above for the enzyme-I may be included.

Specific examples include D-tyrosyl-valyl-α-hydroxyglycine, D-tyrosyl-tryptophanyl-α-hydroxyglycine, glycyl-phenylalanyl-α-hydroxyglycine, phenylalanyl-glycyl-phenylalanyl-α-hydroxyglycine, D-tyrosyl-leucyl-asparaginyl-α-hydroxyglycine, arginyl-phenylalanyl-α-hydroxyglycine, arginyl-alanyl-arginyl-leusyl-α-hydroxyglycine, leucyl-methionyl-α-hydroxyglycine, glycyl-leucyl-methionyl-α-hydroxyglycine, phenylalanyl-glycyl-leucyl-methionyl-α-hydroxylglycine, asparaginyl-arginyl-phenylalanyl-α-hydroxyglycine, triptophanyl-asparaginyl-arginyl-phenylalanyl-α-hydroxyglycine, alanyl-phenylalanyl-α-hydroxyglycine, lysyl-alanyl-phenylalanyl-α-hydroxyglycine, seryl-lysyl-alanyl-phenylalanyl-α-hydroxyglycine, arginyl-tyrosyl-α-hydroxyglycine, glycyl-methionyl-α-hydroxyglycine, glycyl-tyrosyl-α-hydroxyglycine, glycyl-histidyl-α-hydroxyglycine, histidyl-glycyl-α-hydroxyglycine, triptophanyl-glycyl-α-hydroxyglycine, and glycyl-cysteinyl-α-hydroxyglycine and the like.

The enzyme-II is also specified by having substantially the same properties as the enzyme-I, as other physicochemical properties, namely:

(a) the optimum pH is about 5 to 6 and the stable pH is 4 to 9; and (b) the acting optimum temperature is from about 15° to 35° C.

The above properties (a) and (b) are measured by the use of conventional buffers, specifically, Tris-HCl, Mes-potassium hydroxide, Tes-sodium hydroxide, Hepes-potassium hydroxide buffers. The enzyme composition of the present invention can catalyze the above reaction within the temperature range of 1° C. to 55° C., but will be inactivated at 56° C. within about 10 minutes, a slight inactivation is also seen at around 40° C.

Preparation of Enzyme

The enzyme-I and the enzyme-II of the present invention as described above can be prepared according to the separation purification method of enzyme known per se, but preferably are obtained according to the preparation method of the present invention disclosed in the present specification. More specifically, it is possible to utilize the preparation method of the enzyme-I or the enzyme-II characterized by treating the enzyme activity containing compound of the enzyme-I or the enzyme-II with the substrate affinity chromatography by use of the C-terminal glycine adduct represented by the above formula (I) as the ligand and the anion exchange chromatography.

The enzyme activity-containing compound to be used in this method can include all of those containing the enzyme of the present invention, and may be either those derived from an organism or those provided artificially. Generally speaking, as the organism having these enzyme activities, there may be included preparations derived from mammals such as human, bovine, horse, porcine, sheep, rabbit, goat, rat, mouse, etc.; avian such as chicken, jungle fowl, rock-dove, etc.; reptiles such as stone-turtle, viper, rattling snake and cobra; tatrachian such as newt, xenopus, bullfrog, toad, etc.; fish such as lamprey, hagfish, oil shark, electric ray, sturgeon, herring, salmon, eel, Tetrodon rubripes, bream; insects such as coakroach, silkworm, drosophila and bee. As the suitable material to be extracted, there may be included homogenates derived from such organs as the brain, pituitary gland, stomach, heart and liver, as well as biological fluids containing body fluids such as blood and lymph.

More specifically, the enzyme of the present invention (enzyme-I or enzyme-II) can be obtained from the biological fluid having the present enzyme as mentioned above, by substrate affinity chromatography using the C-terminal glycine adduct represented by the following formula (I):

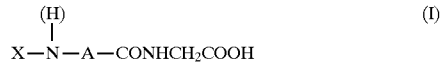

(wherein A and X have the meanings as defined above) as the ligand, used optionally in combination with the conventional method, such as:

(1) fractionation by precipitation;

(2) heparin affinity chromatography;

(3) molecular weight fractionation method by dialysis, gel filtration, etc.; and/or (4) ion-exchange chromatography.

As the above-mentioned ligand, all of the peptide C-terminal glycine adducts represented by the above formula (I) can be used, but preferably they include the peptides comprising 2 to 6 amino acid residues including glycine as specifically a preferable substrate for identification of the above-mentioned enzyme activity. Among them, D-Tyr-Trp-Gly, Phe-Gly-Phe-Gly and Gly-Phe-Gly are more preferable, but that using Phe-Gly-Phe-Gly as the ligand is particularly preferred as having a strong affinity for the enzyme composition of the present invention (also called the present enzyme).

These ligands are generally used as bound to a water-insoluble carrier, and it is important that the carboxyl group of the C-terminal glycine residue of the peptide to be used as the ligand should be in a free state or bondable to the carrier through the amino group of the amino acid residue at the N-terminal. In other words, the carrier may be any one which can be bound to the amino group of the peptide, and an active group reactive with the amino group may be chemically introduced into the carrier, or alternatively a commercially available carrier having the active group already introduced wherein may be used. The method of introducing chemically may be any method generally employed. For example, as described in "Seikagaku Jikkenhou, Vol. 5, Former vol., p. 257–281" written by Kasai, Tokyo Kagaku Dojin (1975), imidocarboxyl group is introduced into agarose by the use of cyanogen bromide. Commercially available activated carriers may include agarose type, cellulose type, hydrophilic polyvinyl type, etc. with the substrate as the index, but any of these may be employed. As the agarose type carrier, there may be included CNBr activated Sepharose 4B (produced by Pharmacia) in which the CNBr method is used for binding the ligand with the amino group, CH-Sepharose 4B, ECH-Sepharose 4B (all produced by Pharmacia) by the carbodiimide method, Affigel 10, Affigel 15 (all are produced by Biorad), the tresyl activated Sepharose 4B (produced by Pharmacia) by use of the tresyl chloride method, etc. As the cellulose type carrier, Formylcellulofine (produced by Chisso) by using the formyl method may be included. As the hydrophilic polyvinyl type carrier, there may be included AF-carboxyltoyopearl 650 by using the carbodiimide method, AF-formyltoyopearl 650 by use of the formyl method, AF-tresyltoyopearl 650 by use of the tresyl chloride method, AF-epoxytoyopearl 650 by use of the epoxy activation method (all are produced by Toso), etc. The binding reaction with the ligand may be carried out according to the instructions for each carrier.

Of these, the method of preparing Affigel 10 is described. The reaction between Affigel 10 and the peptide is carried out in a buffer such as Mopspotassium hydroxide, etc. of 0.001 to 1M, preferably 0.1M. The reaction conditions can be 0° to 20° C., 10 minutes to 24 hours and about pH 3 to 11, but preferably are 4° C., 4 to 24 hours and pH 5 to 9. The mixing ratio of Affigel 10 to the peptide to be used for binding may be within the range of up to 25 μmol per 1 ml of Affigel, because more will be bound as the peptide is added in a larger amount within this range, but conveniently about 1 to 20 μmol may be used with respect to the binding efficiency. After the reaction, the mixture is thoroughly washed with the buffer used during the reaction, and then Tris-HCl (pH 8.0) is added to the final concentration of 50 mM, and the unreacted active groups are blocked according to the shaking method, at 4° C. for one hour, etc., whereby the substrate affinity gel is prepared.

The substrate affinity chromatography may be carried out either batchwise or continuously with the gel packed in a column. The time for contacting the sample with the gel may be such that the present enzyme can be sufficiently adsorbed, but may be generally 20 minutes to 24 hours. Nonadsorbed components are washed away with a buffer having the same composition as that used for equilibration of the gel with a low ionic strength and pH of 6.0 to 11.0, preferably 7.0 to 9.0, for example, 10 mM Hepes-potassium hydroxide (pH 7.0). Among them, the fractions in which the present enzyme activity exists are eluted. The eluting solution may have any composition which can give the present enzyme with a good efficiency, but preferable examples include buffers with a pH of between 7.0 to 9.0 containing about 1 to 40% of acetonitrile together with 0.1 to 1M sodium chloride, such as 10 mM Hepes-sodium hydroxide (pH 7.0) containing 20% acetonitrile and 0.4M sodium chloride. Also, when filled in the column, elution may be carried out with application of the concentration gradient.

In some cases, before or after practicing the above substrate affinity chromatography (hereinafter represented by (5)), or both before and after, the fractionation by way of precipitation as mentioned above (hereinafter represented by (1)), heparin affinity chromatography (hereinafter represented by (2)) dialysis, molecular weight fractionation by gel filtration, etc. (hereinafter represented by (3)) and/or ion-exchange chromatography (hereinafter represented by (4)) may be also practiced. Thus, the present enzymes (enzyme-I and enzyme-II) can be separated form other intervening matters, and for separation of the enzyme-I and enzyme-II, it is effective to practice the steps of (3) and/or (4). Generally speaking, it is preferable to practice the total number of 1 to 6 steps, and further, the above step (5) or (3) as the final step. Specific examples of the combinations of the respective steps may include only (5), (1)→(5), (5)→(3), (2)→(5), (1)→(3)→(5), (2)→(3)→(5), (1)→(5)→(3), (2)→(5)→(3), (2)→(1)→(5), (1)→(2)→(3)→(5), (1)→(2)→(5)→(3), (1)→(3)→(5)→(3), (1)→(2)→(1)→(5), (1)→(2)→(1)→(3)→(5), (2)→(1)→(5)→(3), (2)→(1)→(3)→(5), (2)→(1)→(3)→(5)→(3), (1)→(2)→(3)→(5)→(3), (1)→(3)→(2)→(3)→(5), (1)→(3)→(2)→(3)→(5)→(3), (4)→(3)→(5), (5)→(3)→(5)→(3), (1)→(5)→(3)→(5)→(3), (4)→(5), (1)→(3)→(5)→(4)→(3), (1)→(3)→(4)→(3)→(5), (1)→(2)→(3)→(5)→(3)→(4), (1)→(2)→(3)→(5)→(4)→(3), or (4)→(5)→(3).

Among them, it is preferred that the steps should proceed in the order of (1)→(2)→(3)→(5), (1)→(2)→(3)→(5)→(3), (1)→(3)→(2)→(3)→(5) or (1)→(3)→(2)→(3)→(5)→(3), (1)→(2)→(3)→(5)→(4)→(3).

In the following, the above steps (1) to (4) are described. These steps are all carried out at 0° C. to 10° C., preferably 4° C.

As the substance to be used for fractionation according to precipitation of (1), there may be included salts such as ammonium sulfate, etc., organic solvents such as ethanol, acetone, etc., polymers such as polyethylene glycol, etc. The concentration added is not particularly limited, but it is preferable to use the conditions under which the present enzyme can be recovered with a good efficiency, and can be separated from other protein components. For example, when 30 to 50% of saturated ammonium sulfate, 10 to 15% (w/v) of polyethylene glycol 6000 are added, the present enzyme comes into the precipitated fraction, while many proteins exist in the supernatant portion, whereby purification can be effected with a good efficiency. Addition may be preferably done gradually while stirring with a stirrer. After the mixture is left to stand for at least one hour after completion of the addition, the fractions in which the present enzyme exists are recovered by centrifugation. When the precipitated fraction is recovered, this is dissolved in an appropriate buffer. The buffer, provided that it has pH 6.0 to 11.0, preferably 7.0 to 9.0, may have any composition, for example, Tris-HCl, Hepes-potassium hydroxide, Tes-sodium hydroxide, etc. The concentration is not particularly limited within the range which can maintain the buffering ability, but is preferably about 5 to 50 mM.

The active fraction obtained according to (1) may be subjected again to (1) or proceed to any step of (2) to (5), but when proceeding to (2), (4) or (5) by using a salt such as ammonium sulfate for fractionation of (1), it is necessary to lower the salt concentration to a level at which the present enzyme can be bound to the gel used in the step of (3) or in the subsequent step with addition of an appropriate buffer. On the other hand, when the precipitates are dissolved and left to stand for one hour or longer, or when dialysis is performed, insoluble substances may be formed, which are removed by centrifugation or filtration.

As for heparin affinity chromatography of (2), it may be carried out either batchwise or continuously by filling the gel in a column. Commercially available gels having heparin as the ligand may include heparin Sepharose CL-6B (produced by Pharmacia), Affigel heparin (produced by Biorad), heparin agarose (produced by Sigma), AF-heparintoyopearl 650 (produced by Toso).

The biological extract is contacted directly, or after the treatment of the fraction by precipitation as shown in (1), with the heparin affinity gel. The contact time may be such that the present enzyme can be sufficiently adsorbed, but generally 20 minutes to 12 hours. The components having no affinity for heparin are removed with a buffer having a low ionic strength to the extent that no present enzyme is eluted with pH of 6.0 to 11.0, preferably 7.0 to 9.0, for example, 10 mM Hepes-potassium hydroxide (pH 7.0). Thereafter, the fractions containing the present enzyme are eluted. As the eluting solution, one having a higher recovery of the present enzyme activity is preferred. For example, one having a pH of 6.0 to 11.0 containing a salt generally used for enzyme purification such as 0.5M–2M sodium chloride, potassium chloride, ammonium sulfate, etc. Elution may be performed according to the salt concentration gradient when packed in column, but one-step elution may be also practiced. For example, elution may be effected with 10 mM hepes-potassium hydroxide buffer (pH 7.0) containing 0.3 to 2.0M sodium chloride.

The active fraction obtained in the step (2) may be also provided for any of the steps (1) to (4), or when performing again the step (2), proceeding to the step (4) or (5), the step (3) may be previously conducted, or the ionic strength lowered to a level at which the present gel can be adsorbed to the gel used in (2), (4) or (5) by addition of a large amount of a buffer of 50 mM or lower having a low ionic strength and pH 6.0 to 11.0, preferably 7.0 to 9.0, for example 5 mM Hepes-potassium hydroxide (pH 7.0).

As for the step of removing low molecular weight substances by dialysis, gel filtration, etc. of (3), in the case of dialysis, the membrane to be used may have a cut-off molecular weight to the extent that the present enzyme cannot pass therethrough, but is preferably 1,000 to 10,000. The method of dialysis may be one generally employed as described in, for example, "Seikagaku Jikken Kouza, Vol. 5, Former Vol., p. 252–253" written by Soda, Tokyo Kagaku Dojin (1975), and may be carried out for several hours to several days, against a buffer with low ionic strength having pH 6.0 to 11.0, preferably pH 7.0 to 9.0, such as 10 mM Hepes-potassium hydroxide (pH 7.0), 10 mM Tris-HCel (pH 7.5), etc. Also, during dialysis, when insoluble substances are precipitated, they are removed by, for example, centrifugation, filtration, etc.

Concerning gel filtration, any carrier generally used for gel filtration may be employed. It is preferable that, for example, Sephadex G-10, G-15, G-25, G-50, G-75, G-100, Sephacryl S-200, S-300 (all produced by Pharmacia), Toyopearl HW-40, HW-55 (produced by Toso), Biogel P-2, P-4, P-6, P-10, P-30, P-60, P-100 (all produced by Biorad), etc. The buffer to be used may have the same composition as that used during dialysis. If the ionic strength is too low, however, it may be considered that adsorption of the present enzyme onto the gel well occur, and therefore, the concentration is made 5 to 200 mM, preferably 10 to 20 mM. The method of gel filtration may be practiced as described in, for example, "Seikagaku Jikken Kouza, Vol. 5, Former vol., p. 283–298", written by Soda, Tokyo Kagaku Dojin (1975). After a sample is added in an amount sufficient to obtain separation capacity relative to the bed volume of the gel filtration carrier, elution is effected and the fraction in which the present enzyme activity exists is recovered.

The active fraction obtained by the step of (3) can be permitted to proceed to the respective steps of (1) to (5) without any particular treatment.

For the ion-exchange chromatography, any carriers commercially available for ion-exchange chromatography in general may be used. For example, Aminex, Dowex, Amberlite, SP-Sephacryl M, Asahipak, DEAE-Toyopearl, DEAE-Sephadex, CM-Sepharose, DEAE Bio-Gel A, CM-Cellulose, DEAE-Cellulofine, Partisil SCY, Mono Q and Mono S, etc. are preferred. The buffer to be used and the use method may follow the method as described in the heparin affinity gel item. The basic operational methods may follow those described in general in "Shinkiso Seikagaku Jikkenho 2, Extraction-Purification-Analysis I" (Maruzen, 1988), etc.

The active fractions obtained in the step of (4) may be subjected to any of the steps (1) to (5), but when carrying out again (4) or proceeding to (2) to (5), it (3) must be previously conducted, or a large amount of a buffer of pH 5.0 to 11.0, preferably 6.0 to 8.0, with low ionic strength of 50 mM or lower, for example, Hepes-sodium hydroxide (pH 7.0), etc. must be added to lower the ionic strength to a level at which the present enzyme can be adsorbed onto the gel used in (2), (4) or (5). By passing through the purification steps as mentioned above, the crude product of the enzyme of the present invention can be obtained. Such a crude enzyme of product can be further isolated as fractions having peaks at a molecular weight of about 25,000 and at a molecular weight of 40,000, respectively, by protein separation means using the gel filtration step (3) to give a preparation of the present enzyme.

The respective steps as described above may be practiced by monitoring the activity of the enzyme-I and/or the enzyme-II by use of the compound of the formula (I) or the formula (II) as the substrate following the assaying method of the activity of enzyme which is another present invention as described below, respectively, to obtain the active fraction.

The enzyme-I and the enzyme-II of the present invention also can be prepared by culturing host cells transformed with a plasmid containing a cDNA coding for these enzyme, which can express the cDNA, and collecting either or both of the enzymes from the cultured product produced and accumulated thereby.

The cDNA coding for the enzyme of the present invention which can be used in this method may be any one regardless of its origin, provided that it is derived from a DNA coding for the amino acid sequence a peptide C-terminal amidating enzyme existing in mammals such as human, bovine, horse, porcine, sheep, rabbit, goat, rat, mouse, etc.; avian such as chicken, turkey, etc.; tatrachian such as frog, etc.; reptiles such as snake, etc.; fish such as sardine, mackerel, eel, salmon, etc., and the sequence of Lys-Lys exists at approximately the central portion of the cDNA, but may be preferably one derived from a mammal. More specifically, it is a DNA fragment coding for the amino acid sequence as shown in FIG. 5 obtained by inserting the amino acid sequence of a peptide C-terminal amidating enzyme presently known by one letter representation of the amino acid and yet the deficient portion (represented by –) as desired so as to enhance homology between the species, and the cDNA with the portion corresponding to the hydrophobic amino acid region in the vicinity of the C-terminal thereof being removed can be advantageously used. The respective cDNA's are described, for human, horse, bovine, rat, frog I and frog II, respectively in Biochem. Biophys. Res. Commun. 169, 551–558, 1990; Japanese Patent Application No. 2 (1990)-76331; Mol. Endocrinol, 1, p. 777–790, 1987; Proc. Natl. Acad. Sci. USA, 86, p. 735–739, 1989; Biochem. Biophys. Res. Commun., 148, p. 546–552, 1987; and Biochem. Biophys. Res. Commun., 150, 1275–1281, 1988. Of these, for example, according to the sequence of horse in FIG. 5, the 441st and the 442th K (lysine) and K (lysine) sequences are correspondent. The sequences are well stored in the cDNA's of human, horse, bovine, rat. The cDNA at the former half portion (5' side) than these sequences codes for the protein having the activity of acting on a peptide C-terminal glycine adduct represented by the formula (I) to produce a peptide C-terminal α-hydroxylglycine represented by the formula (II), while the cDNA at the latter half portion (3' side) than the KK sequences codes for the protein having the activity of acting on a C-terminal glycine adduct to form a C-terminal amidated compound represented by the formula (III) and glyoxylic acid. At the site in the vicinity of such KK sequences, the cDNA can be separated into the former half portion and the latter half portion by use of a restriction endonuclease known per se.

For example, according to the sequence of horse in FIG. 5, the region from V (valine) of the 880th to I (isoleucine) of the 901th corresponds to the above-mentioned hydrophobic amino acid region. Therefore, the membrane transport region as mentioned in the present invention refers to the above-mentioned hydrophobic amino acid region of the desired cDNA. Surprisingly, since the cDNA from which the region mentioned above is removed will not only secrete the enzyme produced out of the host all, but also markedly increase the whole amount produced; such a cDNA is particularly preferred for use in the present invention. Since the enzyme-I and the enzyme-II are coded on cDNA mutually adjacent to each other as described above, but these enzymes are released separately by processing in the secretion process in the cells, it is preferable to use the cDNA from which the above-mentioned membrane-transport region is removed. Such a cDNA may be prepared by cutting the portion by using a known restriction endonuclease known Per se from the known cDNA, or also can be chosen from various cDNA's formed by difference in splicing of mRNA at the stage of cloning of said cDNA. A cDNA coding for the enzyme-I and the enzyme-II independently which is separated as described above also may be used.

Cloning of the cDNA utilized in the present invention can be practiced according to the method known per se by the use of a diversity of tissues of various animals as mentioned above. Specifically, it is practiced according to the method generally employed, such as the +, − method, hybridization method, PCR method, etc. (see, for example, Methods in Enzymology, Vol. 152; Guide to Molecular Cloning Techniques, S. L. Berger and A. R. Kimmel, editors, 1987, Acadamic Press, INC.; Methods in Molecular Biology, vol. 4; New Nucleic Acid Techniques, J. M. Walker, editor, 1988, The Humana Press Inc.; Molecular Cloning A Laboratory Manual 2nd Ed., J. Sambrook, E. F. Fritsch, T. Maniatis, editors, 1989, Cold Spring Harbor Laboratory Press), the cDNA region coding for the protein is determined by determining the base sequence of the cDNA clone obtained, and the desired cDNA can be obtained by dividing the cDNA at around the KK sequence portion at the central portion as described above.

Referring to an example of rat, a tissue which forms abundantly a peptide C-terminal amidating enzyme, for example, a pituitary of rat is homogenized together with guanidyl thiocyanate to crush the cells, and RNA fraction is obtained by cecium chloride equilibration density gradient ultra-centrifugation. Subsequently, by affinity chromatography having an oligo-dT-cellulose carried thereon, an RNA having a poly-A (poly-$A^+$RNA) is isolated from the above-mentioned RNA fraction.

By use of the poly-$A^+$RNA as the template, a cDNA library is obtained according to the method known in the art, preferably the method of Okayama-Berg (Mol. Cell. Biol. 2, 161, 1982). From these cDNA libraries, an appropriate probe can be used to screen a positive clone, a positive cDNA clone obtained by rescreening by use of an appropriate probe from the amplified cDNA libraries isolated, and the structure of the desired cDNA can be determined by mapping and sequencing these restriction endonuclease. Also, by incorporating the above-mentioned cDNA into an expression vector, and evaluating the productivity of the peptide C-terminal amidating enzyme of the host transformed therewith, a plasmid containing the desired cDNA can be selected.

The host for expressing the cDNA may be cells of microorganisms such as *E. coli., Bacillus subtilis*, yeast, etc., cultured cells derived from insects, animals, etc., conventionally used. The expression plasmid may be any plasmid which can express efficiently the cDNA in these cells. For example, it can be appropriately chosen from those described in the textbooks as shown below.

Zoku Seikagaku Jikken Koza I, Idenshi Kenkyuho II-Recombinant DNA technique—Chapter 7 Expression of Recombinant (1986), edited by Society of Biochemical Society of Japan, Tokyo Kagaku Dojin; Recombinant DNA, Part D, Section II, Vectors for Expression of Cloned Genes, (1987) edited by RayWu and Lawrence Grossman, Academic Press, INC.; Molecular Cloning, A Laboratory Manual 2nd Ed. Book 3, (1989) edited by J. Sambrook, E. F. Fritsch and T. Maniatis, Cold Spring Harbor Laboratory Press; etc.

For example, when CV-1 conventionally used as the animal culturing cells is used as the host, a promotor of the type pSV, pL2n, pCol and having optionally formulated a selection marker therewith can be used. As for *E. coli*, a vector of the type pGH, pKYP, PHUB, while for yeast, a type of YRp, YEp can be used. Recombination with these cDNA's of these vectors, and transformations, transfections of the host cells with the recombinant plasmids can be practiced according to the procedures of the methods known per se described in the literatures as mentioned above. The transformed cells thus obtained can be cultured in a medium and under cultural conditions conventionally used for proliferation of the cells derived.

The peptide C-terminal amidating enzyme produced and accumulated from such cultured product can be collected easily from the culture broth after removal of the cells in the case of, for example, using animal cultured cells, because the produced enzyme is excreted out of the cells, but may be also collected from the cell lyzate, if necessary. Such collection and purification can be practiced by conventional enzyme purification methods, such as combination of fractionation by precipitation, heparin affinity chromatography and dialysis, etc., but further preferably by joint use of the substrate affinity chromatography with the use of the peptide C-terminal glycine adduct as the ligand.

According to FIGS. 5(A)–5(B), the enzyme-I of the present invention corresponds to the amino acid sequence from the 42th residue P or S to the 442th residue K in the case of human, horse, bovine and rat, and corresponds to the amino acid sequence from the 42th residue P or S to the 231th residue K in the case of horse and bovine. On the other hand, the enzyme-II obtained corresponds to the amino acid sequence from the 443th residue D to the 830th residue K in the case of human, horse, bovine and rat respectively. The term "corresponding" as used herein includes those to which a saccharide is bonded through N-acetylglucosamine.

Use of Enzyme

The present invention provides the use of the enzyme of the present invention as described below, i.e., a method of producing a peptide C-terminal α-hydroxylglycine adduct represented by the above formula (II), which comprises treating a peptide C-terminal glycine adduct represented by the above formula (I) with the above enzyme-I, and a method of producing a peptide C-terminal amidated compound represented by the above formula (III) which comprises treating the above adduct represented by the formula (II) with the enzyme-II. Also, by use of these enzyme-I and enzyme-II in combination, the compound of the formula (I) can be converted to the compound of the formula (III) in a single reaction composition. The use of the enzyme-II in the step of converting the compound from the formula (I) to the formula (III) would be clearly understood to be significant, because the above-mentioned conversion can be accomplished under milder enzyme reaction conditions compared with the case under the presence only of the enzyme of the enzyme-I type where it must be subjected to chemical hydrolysis conditions in converting the compound from the formula (II) to the formula (III). Particularly, these methods are suitable for a treatment of unstable substrates under alkaline conditions.

The preparation methods can be used, provided they contain the enzyme of the present invention, regardless of the concentration, purity, but it is advantageous to use the enzyme containing product from which the intervening proteins are removed to great extent, in view of isolation purification the product from the reaction mixture of the compound of the formula (II).

As the compounds of the formula (I) and (II), all of those described above are included, the corresponding compounds represented by the formula (I) or the formula (II) which can be converted according to the present preparation method to the compound of the formula (III), for example, arginine vasotocin (AVT), lutenizing hormone-release hormone (LH-RH), oxytocin, gastrin, gastrin secretion promoting peptide (GGRP), calcitonin (CT), vasoactive intestinal polypeptide (VIP), throtropin-releasing hormone (TRH), melanophore stimulating hormone (MSH), MSH release inhibiting hormone (MIH), cholecystokinin-octapeptide (CCK-8), substance P (SP), adipokinin, pancreatic polypeptide (PP) growth hormone releasing factor, secretin, caerulein, mollusk cardiostimulant neuropeptide, vasopressin, adrenocorticotropic hormone (ACTH), allochroic hormone, bombesin, light adaptation hormone, motilin, apamin, allitecine, eredoicin, catcinin, granulibelline R, scotophobin, hyranbatecaerulein, obesity cell degranulation peptide, physaremin, phyllocaerulein, phyllomezcin, promellitin, bombinin, mastoballan, manitoballan-X, mellitin-1, lanatensin, lanatensin-R.

The above-mentioned treatment can be practiced in a common buffer, particularly with addition of ascorbic acid and catalase in the reaction mixture in the reaction by use of the enzyme-I, but it is preferable to practice the reaction in view of the conditions of the assaying method of enzyme activity as shown below.

Assaying Method of Enzyme Activity and Screening Method of Novel Enzyme by Use Thereof The enzyme-I and the enzyme-II of the present invention as described above can be monitored according to the assaying method of activity as described below, and the assaying method is useful for practicing the preparation method of the present enzymes as described above.

These assaying methods are based on the finding that the peptide C-terminal amidating reaction is not a one-step reaction as considered in the prior art, but a two-step reaction through an intermediate (peptide C-terminal α-hydroxylglycine adduct).

Initially, the activity of the enzyme-I is assayed according to the method comprising step (a) of buffering a sample to be tested expected to have its activity to pH 5 to 8, and step (b) of adding a peptide C-terminal glycine adduct represented by the above formula (I), L-ascorbic acid and catalase to the buffer followed by incubation, and then measuring the product represented by the formula (II), which has been isolated by chromatography described later, or measuring the product, which has been converted from the compound (II) into the compound (III) under alkaline conditions and then isolated. As a preferable isolation measurement, there may be used the step of detecting the reaction product by HPLC with the use of an acetonitrile-containing buffer (pH 6–10).

The activity of the enzyme-II is assayed according to the method comprising the step (a) of buffering a sample to be tested expected to have its activity to pH 4 to 8, the step (b) of adding a C-terminal α-hydroxylglycine adduct represented by the formula (II) to the buffer followed by incubation, and then detecting the reaction product of the formula (III) or glyoxylic acid by the method known per se. The activity of the enzyme-II is also preferably detected by the above HPLC.

As the sample to be tested as mentioned in the present invention, there may be included any fluid having those activities, particularly biological fluids having those activities, namely homogenates of biological organs, as well as body fluids, such as blood and lymph, and further treated solutions of these obtained by purification treatment, etc. Also, treated solutions derived from microorganism cells are included in the biological fluid.

The buffering agent to be used for the buffering these samples to be tested is not particularly limited, but those conventionally used may be employed. For example, trishydrochloric acid and hepes-potassium hydroxide may be included. The concentration of the buffering agent in the buffer may be any concentration, provided that the buffering action can be accomplished, with a concentration of 20 to 200 mM being suitable in general.

The respective buffers may be controlled to pH 6 to 8, preferably pH 6.5, for the former method, while pH 4 to 8, preferably around pH 6 for the latter method. As the peptide C-terminal glycine adduct to be added to the buffer thus prepared in the former, it is preferable to use one which is a substrate for said enzyme, and represented by the formula (I) enumerated as preferable substrate for identifying the activity of the enzyme-I as described above. The concentration of the compound should be suitably about 0.1 $\mu$M to 2 mM. Further, it is required to add L-ascorbic acid which is considered to function as the cofactor, and catalase as the activating agent. Generally speaking, the concentration of L-ascorbic acid may be preferably 0.5 to 2 mM, and the concentration of catalase suitably 40 to 100 $\mu$g/ml. A metal ion may be also added in the buffer, but this addition is not particularly required for the present activity assay, which addition however is preferable because higher activity may be sometimes obtained as compared in the case of no addition. As the metal ion to be employed, $Zn^{2+}$, $Cu^{2+}$, $Ni^{2+}$, $Ni^{2+}$, $Co^{2+}$, $Fe^{3+}$, etc. is appropriate, particularly preferably $Cu^{2+}$ and $Zn^{2+}$. The concentration of the metal ion in the buffer may be suitably 0 to 1000 $\mu$M, preferably 0 to 10 $\mu$M. The compounds for providing such metal ions are not particularly limited, but may include $CuSO_4$, $CuCl_2$, $ZnCl_2$, $NiCl_2$, $CoCl_2$, $FeCl_3$, etc.

For a specific example of such reaction composition, reference may be made to the reaction composition A of Example 7 as described below. On the other hand, the reaction composition in the latter is prepared by use of the corresponding compound of the formula (II) in place of the above formula (I). In this case, no cofactor such as ascorbic acid, catalase, etc. is required.

In these both assaying methods, the amount of the test sample employed is not particularly limited and can be varied, but preferably is suitably adjusted to contain a pmol/hr or more, more preferably 10×a pmol/hr or more, most preferably 10×a pmol/hr to a mol/hr, based on the amount of the substrate existing in the reaction system (defined as a nanomol (nmol)) (unit indicates enzyme activity, represented in the substrate amount which can be reacted at 37° C. for one hour (e.g., picomol (pmol)).

Incubation may be carried out at 1° to 55° C., particularly in the former preferably 25° to 40° C., particularly preferably around 30° C. with stirring for 2 to 24 hours, while in the latter preferably at 15° to 35° C., most preferably around 25° C. stationarily for one minute to 48 hours.

For detection of the compound of the formula (II) and the compound of the formula (III) formed respectively in the steps as described above, there can be employed and method which can measure by separation those substrate and the product, for example, the compound of the formula (I) and the compound of the formula (II) in the former, while the compound of the formula (II) and the compound of the formula (III) in the latter. Generally speaking, separation measurement can be conducted by separation, purification by chromatography as mentioned below. As the chromatography which can be used for the above treatment, there may be included ion-exchange chromatography, reverse phase chromatography, gel filtration, affinity chromatography, high performance liquid chromatography (HPLC), thin layer chromatography (TLC), etc. The substrate represented by the formula (II) and the amidated product represented by the formula (III) in the reaction system of the latter have peptide C-terminals of carboxyl group and amide group, respectively, with the charges being different. Ion-exchange chromatography, reverse phase chromatography, etc. using this property are preferred. Affinity chromatography by use of the antibody of the product may be also effectively used. However, although separation of the substrate represented by the formula (I) and the product represented by the formula (II) in the reaction system of the former, according to the high performance liquid chromatography (HPLC) with the use of an acetonitrile containing buffer (pH 6 to 10, preferably pH 9) as the eluate attempted for the first time by the present inventors, separation measurement can be done advantageously. The eluate should be particularly preferably applied with a straight line concentration gradient of acetonitrile concentration. As the column for HPLC, any kind of commercially available columns suited for the present object can be used, but it is particularly advantageous to use Capcell Pak C18SG, 300 Å (produced by Shiseido).

The substrate and the product thus separated may be assayed for either the chemical or physical labels (optionally bound) of them. For such measurement, known labels, known assaying methods can be used, and it would be generally convenient to utilize the UV-absorption derived from the amino acid constituting the substrate peptide.

Since the assaying methods as described are correct and simple, by applying these to the biological fluids as mentioned above, the enzymes having the respective activities of the enzyme-I and the enzyme-II, can be searched. Such searching methods are provided as the eighth and the ninth inventions of the present application, respectively.

The biological fluid to be searched is inclusive of those of which enzymatic activity can be expected as described above, as a matter of course, and also all of living body cells, tissues, extracts of other animals and vegetables. For example, extracts may be prepared according to the extraction methods in general, as described in "Jikken Seibutsugaku Koza 6, Saibo Bunkakuho" (Maruzen, 1984), "Seikagaku Jikken Koza 5, Kosokenkyuho (Former)" (Tokyo Kagaku Dojin, 1975), "Kiso Seikagaku Jikkenho 1, Seibutsu Zairyo no Toriatsukaikata" (Maruzen, 1974).

DNA Sequences for Enzyme-I and Enzyme-II Derived from Horse

According to the present invention, there is provided a cDNA sequence coding for a polypeptide having a peptide C-terminal activities of enzyme-I and the enzyme-II. Since these enzymes provide the possibility of an excellent activity and stability in comparison with those of peptide C-terminal amidating enzymes known in the art (see Published International Application: WO89/1209), the reasons for providing the above DNA sequences will be clear. For the source of the enzyme, any kind may be available, provided that it is an organ or a tissue where the such enzyme exists, but primarily those derived from atrium, pituitary gland, brain or stomach are to be used.

The cDNA coding for the peptide having the C-terminal amidating enzyme activity according to the present invention is specifically shown in FIG. 13. In this Figure, the base sequence of the longest cDNA fragment and the amino acid sequence coded for thereby is shown by one letter representation. The content within the [ ] in FIG. 13 (No. 4) is a cDNA deleted portion which appears to be formed through the difference in mRNA splicing found as the result of analysis of some cDNA's. Therefore, several kinds of the cDNA according to the present invention exist also for the amino acid sequences of the polypeptide to be coded for thereby. For example, as for the amino acid sequence of the polypeptide having the peptide C-terminal amidating enzyme activity derived from horse as described in the present invention, there exist 4 kinds having at least the common sequence up to a certain chain lenth and the 4 kinds of sequences, respectivly, upstream thereof.

Common amino acid sequence 10                    20
MetAlaGlyLeuArgSerLeuLeuValLeuLeuLeuValPheGlnSerSerCysLeuGly 30                    40
PheArgSerProLeuSerValPheLysArgPheLysGluThrThrArgProPheSerAsn 50                    60
GluCysLeuGlyThrThrArgProValIleProIleAspSerSerAspPheAlaLeuAsp 70                    80
IleArgMetProGlyValThrProLysGlnSerAspThrTyrPheCysMetSerMetArg 90                    100
LeuProMetAspGluGluThrPheValIleAspPheLysProArgAlaSerMetAspThr 110                  120
ValHisHisMetLeuLeuPheGlyCysAsnMetProSerSerThrGlySerTyrTrpPhe -continued 130    140
CysAspGluGlyValCysThrAspLysAlaAsnIleLeuTyrAlaTrpAlaArgAsnAla 150    160
ProProThrArgLeuProLysGlyValGlyPheArgValGlyGlyGluThrGlySerLys 170    180
TyrPheValLeuGlnValHisTyrGlyAspIleSerAlaPheArgAspAsnHisLysAsp 190    200
CysSerGlyValSerLeuHisLeuThrArgLeuProGlnProLeuIleAlaGlyMetTyr 210    220
LeuMetMetAlaLeuAspThrValIleProAlaGlyGluLysValValAsnSerAspLeu 230    240
SerCysHisTyrLysLysTyrProMetHisValPheALaTyrArgValHisThrHisHis 250    260
LeuGlyLysValValSerGlyTyrArgValArgAsnGlyGlnTrpThrLeuIleGlyArg 270    280
GlnSerProGlnLeuProGlnAlaPheTyrProValGluHisProValAspValSerPhe 290    300
GlyAspIleLeuAlaAlaArgCysValPheThrGlyGluGlyArgThrGluAlaThrHis 310    320
IleGlyGlyThrSerSerAspGluMetCysAsnLeuTyrIleMetTyrTyrMetGluAla 330    340
LysHisAlaValSerPheMetThrCysThrGlnAsnValAlaProGluMetPheArgThr 350    360
IleProProGluAlaAsnIleProIleProValLysSerAspMetValMetMetHisGly 370    380
HisHisLysGluThrGluAsnLysAspLysThrSerLeuGlnGlnProLysGlnGluGlu 390    400
GluValLeuGluGlnGlyAspPheTyrSerLeuLeuSerLysLeuLeuGlyGluArgGlu 410    420
AspValValHisValHisLysThrAsnProThrGluLysAlaGluSerGluSerAspLeu 430    440
ValAlaGluIleAlaAsnValValGlnLysLysAspLeuGlyArgSerAspAlaArgGlu 450    460
SerAlaGluHisGluAspArgGlyAsnAlaIleLeuValArgAspArgIleHisLysPhe 470    480
HisArgLeuGluSerThrLeuArgProThrGluSerArgValIleSerValProGlnPro 490    500
LeuProGlyGluGlyThrTrpGluProGluHisThrGlyAspPheHisValGluGluAla 510    520
LeuAspTrpProGlyValTyrLeuLeuProGlyGlnValSerGlyValAlaLeuAspLeu 530    540
GlnAsnAsnLeuValIlePheHisArgGlyAspHisValTrpAspGlyAsnSerPheAsp 550    560
SerLysPheValTyrGlnGlnArgGlyLeuGlyProIleGluGluAspThrIleLeuVal 570    580
IleAspProAsnAsnAlaAlaValLeuGlnSerSerGlyLysAsnLeuPheTyrLeuPro 590    600
HisGlyLeuSerIleAspLysAspGlyAsnTyrTrpValThrAspValAlaLeuHisGln 610    620
ValPheLysLeuAspProAsnSerLysGluGlyProLeuLeuIleLeuGlyArgSerMet 630    640
GlnProGlySerAspGlnAsnHisPheCysGlnProThrAspValAlaValAspProAsn 650    660
ThrGlyThrIlePheValSerAspGlyTyrCysAsnSerArgIleValGlnPheSerPro 670    680
ThrGlyArgPheIleThrGlnTrpGlyGluGluSerSerGluSerAsnProLysProGly 690    700
GlnPheArgValProHisSerLeuAlaLeuValProHisLeuGlyGlnLeuCysValAla 710    720
AspArgGluAsnGlyArgIleGlnCysPheLysThrAspThrLysGluPheValArgGlu 730    740
IleLysHisAlaSerPheGlyArgAsnValPheAlaIleSerTyrIleProGlyLeuLeu 750    760
PheAlaValAsnGlyLysProTyrPheGlyAspGlnLysProValGlnGlyPheValMet 770    780
AsnPheSerSerGlyGluIleIleAspValPheLysProValArgLysHisPheAspMet 790    800
ProHisAspIleThrAlaSerGluAspGlyThrValTyrValGlyAspAlaHisThrAsn ThrValTrpLysPheThrSerThrGlu Amino acid sequences in different regions (i)

810    820
ThrAlaGlnValTrpPheProGlyValAspLeuHisHisSerSerValAlaMetLeuTrp 830    840
TrpGlnLeuThrTyrLysLysArgLysIleAspAsnArgCysTyrLeuArgAlaAsnLeu 850    860
ProGlnGlnMetLysLysLysArgValGluHisArgSerValLysLysAlaGlyIleGlu 870    880
ValGlnGluIleLysGluSerGluAlaValValGluThrLysMetGluAsnLysProAla 890    900
SerSerGluLeuGlnLysMetGlnGluLysGlnLysLeuIleLysGluProGlySerGly 910    920
ValProValValLeuIleThrThrLeuLeuValIleProValValValLeuLeuAlaIle 930 940
AlaIlePheIleArgTrpLysLysSerArgAlaPheGlyGluSerGluHisLysValGlu 950 960
AlaSerSerGlyArgValLeuGlyArgLeuArgGlyLysGlySerGlyGlyLeuAsnLeu 970 980
GlyAsnPhePheAlaSerArgLysGlyTyrSerArgLysGlyPheAspArgLeuSerThr 990 1000
GluGlySerAspGlnGluLysAspGluAspAspGlySerGluSerGluGluGluTyrSer 1010 1020
AlaProLeuProAlaProValProSerSerSer (ii)

810 820
ArgValGluHisArgSerValLysLysAlaGlyIleGluValGlnGluIleLysGluSer 830 840
GluAlaValValGluThrLysMetGluAsnLysProAlaSerSerGluLeuGlnLysMet 850 860
GlnGluLysGlnLysLeuIleLysGluProGlySerGlyValProValValLeuIleThr 870 880
ThrLeuLeuValIleProValValValLeuLeuAlaIleAlaIlePheIleArgTrpLys 890 900
LysSerArgAlaPheGlyGluSerGluHisLysValGluAlaSerSerGlyArgValLeu 910 920
GlyArgLeuArgGlyLysGlySerGlyGlyLeuAsnLeuGlyAsnPhePheAlaSerArg 930 940
LysGlyTyrSerArgLysGlyPheAspArgLeuSerThrGluGlySerAspGlnGluLys 950 960
AspGluAspAspGlySerGluSerGluGluGluTyrSerAlaProLeuProAlaProVal

970
ProSerSerSer (iii)
810                                       820
ThrAlaGlnValTrpPheProGlyValAspLeuHisHisSerSerValAlaMetLeuTrp 830                                       840
TrpGlnLeuThrTyrLysLysArgLysIleAspAsnArgCysTyrLeuArgAlaAsnLeu 850                                       860
ProGlnGlnMetLysLysLysArgValGluHisArgSerValLysLysAlaGlyIleGlu 870                                       880
ValGlnGluIleLysAlaGluSerGluHisLysValGluAlaSerSerGlyArgValLeu 890                                       900
GlyArgLeuArgGlyLysGlySerGlyGlyLeuAsnLeuGlyAsnPhePheAlaSerArg 910                                       920
LysGlyTyrSerArgLysGlyPheAspArgLeuSerThrGluGlySerAspGlnGluLys 930                                       940
AspGluAspAspGlySerGluSerGluGluGluTyrSerAlaProLeuProAlaProVal 950
ProSerSerSer, and (iv)
810                                       820
ArgValGluHisArgSerValLysLysAlaGlyIleGluValGlnGluIleLysAlaGlu 830                                       840
SerGluHisLysValGluAlaSerSerGlyArgValLeuGlyArgLeuArgGlyLysGly 850                                       860
SerGlyGlyLeuAsnLeuGlyAsnPhePheAlaSerArgLysGlyTyrSerArgLysGly 870                                       880
PheAspArgLeuSerThrGluGlySerAspGlnGluLysAspGluAspAspGlySerGlu 890                                       900
SerGluGluGluTyrSerAlaProLeuProAlaProValProSerSerSer The polypeptides having these amino acid sequences can be translated not merely by the 4 kinds of cDNA sequences, but also by use of a DNA comprising a combination of different codons coding for the same amino acid, and the DNA sequences of the present invention are inclusive of all of those. Further, it may be interpreted that, even if a part of the amino acid sequence may be modified by replacement, addition or removal to the extent that the C-terminal amidating enzyme activity is not lost, such a modified sequence can be suitable for the purpose of the present invention. Specific examples of these may include those having the common base sequence shown below and the respective different base sequence portions downstream thereof.

Common base sequence

CGGCGTGGA CATGGCTGGC CTTCGTAGCC TGCTAGTTCT CCTCCTTGTT

TTTCAGAGCA GCTGTTTGGG TTTCAGAAGC CCACTTTCTG TCTTTAAGAG

GTTTAAAGAA ACTACCAGAC CATTTTCCAA TGAATGTCTT GGTACCACCA

GACCAGTCAT TCCTATTGAT TCATCAGATT TTGCATTGGA TATTCGCATG

CCTGGAGTCA CACCTAAACA GTCTGATACA TACTTCTGCA TGTCGATGCG

TTTGCCAATG GATGAGGAAA CCTTCGTGAT TGACTTCAAA CCTCGTGCCA

GCATGGATAC TGTCCATCAT ATGTTACTTT TTGGTTGCAA TATGCCCTCA

TCCACTGGAA GTTACTGGTT TTGTGATGAA GGCGTCTGTA CAGACAAAGC

CAATATTCTC TATGCCTGGG CAAGAAATGC TCCCCCCACC AGACTCCCCA

AAGGTGTTGG ATTCAGAGTT GGAGGAGAGA CTGGAAGTAA ATACTTCGTA

CTACAAGTAC ACTATGGGGA TATTAGTGCT TTTAGAGATA ATCACAAGGA

CTGTTCTGGT GTGTCCTTAC ACCTCACACG CCTGCCACAG CCTTTAATTG

CTGGCATGTA CCTTATGATG GCTCTTGACA CTGTTATACC AGCAGGAGAG

AAAGTGGTGA ATTCTGACCT TTCATGCCAT TATAAAAAGT ACCCAATGCA

TGTCTTTGCC TATAGAGTTC ACACTCACCA TTTAGGTAAG GTAGTAAGTG

GCTACAGAGT AAGAAATGGA CAGTGGACAC TGATTGGACG TCAGAGCCCC

-continued

```
CAGCTGCCAC AGGCTTTCTA CCCTGTGGAA CACCCAGTAG ATGTCAGTTT

TGGTGACATA CTGGCAGCAA GATGTGTGTT CACTGGTGAA GGAAGGACAG

AAGCCACGCA CATTGGTGGC ACATCTAGTG ATGAAATGTG CAACTTATAC

ATTATGTATT ACATGGAAGC CAAGCACGCA GTTTCTTTCA TGACCTGTAC

CCAGAATGTA GCTCCAGAAA TGTTCAGAAC CATCCCCCCA GAGGCCAATA

TTCCAATTCC TGTGAAGTCC GACATGGTTA TGATGCATGG ACATCACAAA

GAAACAGAGA ACAAAGATAA GACTTCACTA CAACAGCCAA AACAAGAAGA

AGAAGTGTTA GAACAGGGTG ATTTCTATTC ACTGCTTTCC AAGCTGCTAG

GAGAAAGGGA AGATGTTGTT CATGTGCATA AATATAACCC TACAGAAAAG

GCAGAATCAG AGTCAGACCT GGTAGCTGAG ATTGCAAATG TAGTCCAAAA

GAAGGATCTC GGTCGATCTG ATGCCAGAGA GAGTGCAGAG CATGAGGACA

GGGGCAATGC TATTCTTGTC AGAGACAGAA TTCACAAATT CCACAGACTA

GAATCTACTT TGAGGCCAAC AGAGAGCAGA GTTATCTCAG TACCGCAGCC

CCTACCTGGT GAAGGCACCT GGGAACCAGA ACACACAGGA GATTTCCATG

TAGAAGAGGC ACTGGATTGG CCTGGAGTAT ACTTGTTACC AGGCCAGGTT

TCTGGGGTAG CTCTGGACCT TCAGAATAAC CTGGTGATTT CCACAGAGG

TGACCATGTC TGGGATGGAA ACTCTTTTGA CAGCAAGTTT GTGTACCAGC

AAAGAGGACT CGGGCCAATT GAAGAAGATA CTATTCTTGT CATAGATCCA

AATAATGCTG CAGTCCTCCA GTCCAGTGGA AAAAATCTGT TTTACTTGCC

ACATGGCTTG AGCATAGACA AAGATGGAAA TTATTGGGTC ACAGACGTGG

CTCTCCATCA GGTGTTCAAA CTGGATCCAA ACAGTAAAGA AGGCCCTCTG

TTGATCCTGG GAAGAAGCAT GCAACCAGGC AGTGACCAGA ATCACTTCTG

TCAACCCACC GATGTGGCTG TAGATCCAAA CACTGGGACC ATCTTTGTAT

CAGATGGTTA CTGCAACAGT CGGATCGTGC AGTTTTCACC AACTGGAAGG

TTCATCACAC AGTGGGGAGA AGAGTCTTCT GAGAGCAATC CTAAACCAGG

CCAGTTCAGG GTTCCTCACA GCTTGGCCCT TGTGCCTCAT TTGGGCCAAT

TATGTGTGGC CGACCGGGAA AATGGTCGGA TCCAGTGTTT TAAAACTGAC

ACCAAAGAAT TTGTGCGAGA GATTAAGCAT GCATCATTTG GAAGAAATGT
```

ATTTGCAATT TCGTATATAC CAGGTTTGCT CTTTGCCGTA AATGGGAAGC

CTTACTTTGG GGACCAAAAA CCAGTACAAG GATTTGTGAT GAACTTTTCC

AGTGGGGAAA TTATAGATGT CTTCAAGCCA GTGCGCAAGC ACTTTGACAT

GCCTCATGAC ATTACTGCAT CTGAAGACGG GACTGTGTAT GTTGGAGATG

CTCACACCAA CACCGTGTGG AAGTTCACTT CGACTGAA

<u>Different base sequence portions</u>

(i)

AC AGCCCAGGTC

TGGTTCCCGG GTGTGGACCT ACATCACTCG TCAGTGGCCA TGCTGTGGTG

GCAGCTCACA TACAAAAAGA GGAAGATTGA CAACAGATGT TATCTCAGGG

CCAATCTTCC TCAGCAAATG AAAAAAAAAA GAGTGGAGCA TCGATCAGTT

AAAAAGGCTG GCATTGAGGT CCAGGAAATC AAAGAATCCG AGGCAGTTGT

TGAAACCAAA ATGGAGAACA AACCCGCCTC CTCAGAATTG CAGAAGATGC

AAGAGAAACA GAAACTGATC AAAGAGCCAG GCTCGGGAGT GCCCGTTGTT

CTCATTACAA CCCTTCTGGT TATTCCGGTG GTTGTCCTGC TGGCCATTGC

CATATTTATT CGGTGGAAAA AATCAAGGGC CTTTGGAGAG TCTGAACACA

AAGTCGAGGC AAGTTCAGGA AGAGTACTGG GAAGACTTAG AGGAAAAGGA

AGTGGAGGCT TAAACCTCGG AAATTTCTTT GCGAGCCGTA AAGGCTACAG

TCGGAAAGGG TTTGACCGGC TCAGCACCGA GGGGAGTGAC CAGGAGAAAG

ATGAGGATGA CGGAAGTGAA TCAGAAGAAG AATATTCAGC ACCTCTGCCC

GCACCTGTAC CTTCCTCCTC CTGAAAACTG GGCTTTGATT TAGTTGATGA

GATTTACCAA GAATGCCAGG TTCCTTTCCC TTTAGCACGA TTAGAGTTTT

GTGTATTTAA TTGTAAACTG TACTAGTCTG TGTGGGACTG TACACATTTT

ATTTACTTCG TTTTGGTTTA GTTGGCTTCT GTTTCTGGTT GAGGAGTTTC

CTAAAAGTTC ATAACAGTGC CATTGTCTTT ATCTGAACAT AGAATAGAGA

AACAGTCCTC TTCTTCCATC ACGTTACTAA TTTAATGATG GAAGCTTTGC

TCATTTACAT TTTGAGACTT TTCTGTAGGT GTAAATAGCC CCATTCTCTG

CTTGGACACA GTCTTTTCCC AATAGCACTT CCATTGCCAG TGTCTTTCTT

TGGTGCCTTT CCTGTTCAGC ATTCTCAGCC TGTGGCAGTA AAGAGAAACT

-continued
TTGTGCTACA CGACGACGAA GCTGCTAAAT CTTCTTCTAT TTTTTTAAAA

TCACTAACAT TATATTGCAA CAAGGGAAAG AAAAAAGTCT CTATTTAAAT

TCTTTTTTTT AAATTTTCTT CTTTAGTTGG TGTGTTTTTG GGATGTCTTA

TTTTTAGATG GTTACACTGT TAGAACACTA TTTTCAGAAT CTGAATGTAA

TTTGTGTAAT AAAGTGTTTT CAGAGCATTA GCTGTCAGAG TGTATTTTGC

CAATTTTTGC ATATGTCCAG GGTTTTGTAT ACTTTTGTAA TAATTACATA

AACCACAGAT TGAGTGAAAC CTACTCAATG TCTTCAACCA AAAGAAATGT

GTTGTATTGT ATTAAAATCA AGAAGATATT TTGTTATGTA GCTGATACAA

ATTAAAAACC AGCCTAAGAG CTTACATACA TGTGTAAAAT CAGGCTCTCT

GATGATTCAA CGAGAGTGTT TGCCTGTATA TCAATCAGAA GGTAAATATC

TGAATAAAAG GTGATCATAG CTGAGAGGAA AAAAAAAAAA AAAAAA (ii)
AG AGTGGAGCAT

CGATCAGTTA AAAAGGCTGG CATTGAGGTC CAGGAAATCA AAGAATCCGA

GGCAGTTGTT GAAACCAAAA TGGAGAACAA ACCCGCCTCC TCAGAATTGC

AGAAGATGCA AGAGAAACAG AAACTGATCA AAGAGCCAGG CTCGGGAGTG

CCCGTTGTTC TCATTACAAC CCTTCTGGTT ATTCCGGTGG TTGTCCTGCT

GGCCATTGCC ATATTTATTC GGTGGAAAAA ATCAAGGGCC TTTGGAGAGT

CTGAACACAA AGTCGAGGCA AGTTCAGGAA GAGTACTGGG AAGACTTAGA

GGAAAAGGAA GTGGAGGCTT AAACCTCGGA AATTTCTTTG CGAGCCGTAA

AGGCTACAGT CGGAAAGGGT TTGACCGGCT CAGCACCGAG GGGAGTGACC

AGGAGAAAGA TGAGGATGAC GGAAGTGAAT CAGAAGAAGA ATATTCAGCA

CCTCTGCCCG CACCTGTACC TTCCTCCTCC TGAAAACTGG GCTTTGATTT

AGTTGATGAG ATTTACCAAG AATGCCAGGT TCCTTTCCCT TTAGCACGAT

TAGAGTTTTG TGTATTTAAT TGTAAACTGT ACTAGTCTGT GTGGGACTGT

ACACATTTTA TTTACTTCGT TTTGGTTTAG TTGGCTTCTG TTTCTGGTTG

AGGAGTTTCC TAAAAGTTCA TAACAGTGCC ATTGTCTTTA TCTGAACATA

GAATAGAGAA ACAGTCCTCT TCTTCCATCA CGTTACTAAT TTAATGATGG

AAGCTTTGCT CATTTACATT TTGAGACTTT TCTGTAGGTG TAAATAGCCC

-continued

CATTCTCTGC TTGGACACAG TCTTTTCCCA ATAGCACTTC CATTGCCAGT

GTCTTTCTTT GGTGCCTTTC CTGTTCAGCA TTCTCAGCCT GTGGCAGTAA

AGAGAAACTT TGTGCTACAC GACGACGAAG CTGCTAAATC TTCTTCTATT

TTTTTAAAAT CACTAACATT ATATTGCAAC AAGGGAAAGA AAAAAGTCTC

TATTTAAATT CTTTTTTTTA AATTTTCTTC TTTAGTTGGT GTGTTTTTGG

GATGTCTTAT TTTTAGATGG TTACACTGTT AGAACACTAT TTTCAGAATC

TGAATGTAAT TTGTGTAATA AAGTGTTTTC AGAGCATTAA AAAAAAAAAA

AAAAAAAAAA AAAAAAAAAA AAAAAAAAAA A (iii)
AC AGCCCAGGTC

TGGTTCCCGG GTGTGGACCT ACATCACTCG TCAGTGGCCA TGCTGTGGTG

GCAGCTCACA TACAAAAAGA GGAAGATTGA CAACAGATGT TATCTCAGGG

CCAATCTTCC TCAGCAAATG AAAAAAAAAA GAGTGGAGCA TCGATCAGTT

AAAAAGGCTG GCATTGAGGT CCAGGAAATC AAAGCAGAGT CTGAACACAA

AGTCGAGGCA AGTTCAGGAA GAGTACTGGG AAGACTTAGA GGAAAAGGAA

GTGGAGGCTT AAACCTCGGA AATTTCTTTG CGAGCCGTAA AGGCTACAGT

CGGAAAGGGT TTGACCGGCT CAGCACCGAG GGGAGTGACC AGGAGAAAGA

TGAGGATGAC GGAAGTGAAT CAGAAGAACA ATATTCAGCA CCTCTGCCCG

CACCTGTACC TTCCTCCTCC TGAAAACTGG GCTTTGATTT AGTTGATGAG

ATTTACCAAG AATGCCAGGT TCCTTTCCCT TTAGCACGAT TAGAGTTTTG

TGTATTTAAT TGTAAACTGT ACTAGTCTGT GTGGGACTGT ACACATTTTA

TTTACTTCGT TTTGGTTTAG TTGGCTTCTG TTTCTGGTTG AGGAGTTTCC

TAAAAGTTCA TAACAGTGCC ATTGTCTTTA TCTGAACATA GAATAGAGAA

ACAGTCCTCT TCTTCCATCA CGTTACTAAT TTAATGATGG AAGCTTTGCT

CATTTACATT TTGAGACTTT TCTGTAGGTG TAAATAGCCC CATTCTCTGC

TTGGACACAG TCTTTTCCCA ATAGCACTTC CATTGCCAGT GTCTTTCTTT

GGTGCCTTTC CTGTTCAGCA TTCTCAGCCT GTGGCAGTAA AGAGAAACTT

TGTGCTACAC GACGACGAAG CTGCTAAATC TTCTTCTATT TTTTTAAAAT

CACTAACATT ATATTGCAAC AAGGGAAAGA AAAAAGTCTC TATTTAAATT

-continued

CTTTTTTTTA AATTTTCTTC TTTAGTTGGT GTGTTTTTGG GATGTCTTAT

TTTTAGATGG TTACACTGTT AGAACACTAT TTTCAGAATC TGAATGTAAT

TTGTGTAATA AAGTGTTTTC AGAGCATTAG CTGTCAGAGT GTATTTTGCC

AATTTTTGCA TATGTCCAGG GTTTTGTATA CTTTTGTAAT AATTACATAA

ACCACAGATT GAGTGAAACC TACTCAATGT CTTCAACCAA AAGAAATGTG

TTGTATTGTA TTAAAATCAA GAAGATATTT TGTTATGTAG CTGATACAAA

TTAAAAACCA GCCTAAGAGC TTACATACAT GTGTAAAATC AGGCTCTCTG

ATGATTCAAC GAGAGTGTTT GCCTGTATAT CAATCAGAAG GTAAATACTT

GAATAAAAGG TGATCATAGC TGAGAGGAAA AAAAAAAAAA AAAAA (iv)
                                AG AGTGGAGCAT

CGATCAGTTA AAAAGGCTGG CATTGAGGTC CAGGAAATCA AAGCAGAGTC

TGAACACAAA GTCGAGGCAA GGTCAGGAAG AGTACTGGGA AGACTTAGAG

GAAAAGGAAG TGGAGGCTTA AACCTCGGAA ATTTCTTTGC GAGCCGTAAA

GGCTACAGTC GGAAAGGGTT TGACCGGCTC AGCACCGAGG GGAGTGACCA

GGAGAAAGAT GAGGATGACG GAAGTGAATC AGAAGAAGAA TATTCAGCAC

CTCTGCCCGC ACCTGTACCT TCCTCCTCCT GAAAACTGGG CTTTGATTTA

GTTGATGAGA TTTACCAAGA ATGCCAGGTT CCTTTCCCTT TAGCACGATT

AGAGTTTTGT GTATTTAATT GTAAACTGTA CTAGTCTGTG TGGGACTGTA

CACATTTTAT TTACTTCGTT TTGGTTTAGT TGGCTTCTGT TTCTGGTTGA

GGAGTTTCCT AAAAGTTCAT AACAGTGCCA TTGTCTTTAT CTGAACATAG

AATAGAGAAA CAGTCCTCTT CTTCCATCAC GTTACTAATT TAATGATGGA

AGCTTTGCTC ATTTACATTT TGAGACTTTT CTGTAGGTGT AAATAGCCCC

ATTCTCTGCT TGGACACAGT CTTTTCCCAA TAGCACTTCC ATTGCCAGTG

TCTTTCTTTG GTGCCTTTCC TGTTCAGCAT TCTCAGCCTG TGGCAGTAAA

GAGAAACTTT GTGCTACACG ACGACGAAGC TGCTAAATCT TCTTCTATTT

TTTTAAAATC ACTAACATTA TATTGCAACA AGGGAAAGAA AAAAGTCTCT

ATTTAAATTC TTTTTTTTAA ATTTTCTTCT TTAGTTGGTG TGTTTTTGGG

ATGTCTTATT TTTAGATGGT TACACTGTTA GAACACTATT TTCAGAATCT

-continued
GAATGTAATT TGTGTAATAA AGTGTTTTCA GAGCATTAAA AAAAAAAAAA

AAAAAAAAAA AAAAAAAAAA AAAAAAAAA

The cloning of the cDNA of the present invention can be practiced according to the method known per se by the use of various tissues of horse as in the description concerning rat.

In the following, the cDNA preparation method of the present invention is described in more detail.

A tissue which forms abundantly a peptide C-terminal amidating enzyme in horse (hereinafter called "plus tissue"), for example, an atrium of horse is homogenized together with guanidyl thiocyanate to crush the cells, and RNA fraction is obtained by cecium chloride equilibration density gradient ultracentrifugation. Subsequently, by affinity chromatography having an oligo-dT-cellulose carried thereon, an RNA having a poly-A (poly-A$^+$RNA) is isolated from the above-mentioned RNA fraction.

By use of the poly-A$^+$RNA as the template, a cDNA library is obtained according to the method known in the art, preferably the method of Okayama-Berg (Mol. Cell. Biol. 2, 161, 1982). The method of Okayama-Berg is practiced as described below. That is, the poly-A portion of poly-A$^+$RNA is adsorbed onto the poly-T portion of the Okayama-Berg vector, whereby the reaction of the reverse transcriptase is carried out to synthesize a cDNA. After addition of an oligodC to the 3'-end of the cDNA with a terminal deoxynucleotidyl transferase, the vector DNA is cleaved with a restriction endonuclease HindIII. After ligation of an oligodG linker, the vector is cyclized and then the RNA portion is replaced with DNA with a DNA polymerase to obtain a cDNA containing plasmid. By the use of these plasmids, E. coli is transformed according to such method as the calcium chloride method (Strik, P. et. al., J. Bacteriol. 138, 1033, 1979). By selecting an ampicillin-resistant strain with an ampicillin-added flat plate medium, a plasmid-accepting microorganism is procured.

On the other hand, the above-mentioned plus tissue, namely a tissue of producing abundantly a C-terminal amidating enzyme, and a tissue of producing not so much a C-terminal amidating enzyme (hereinafter called "minus tissue"), for example, liver of horse, are prepared, and poly-A$^+$RNA is isolated according to the methods as described above from the respective cells. The 5'-OH of RNA is labelled with $^{32}$P by use of polynucleotide kinase and [γ-$^{32}$]PATP, and this is used as the probe.

Next, according to the colony hybridization method (Hanahan, D. et. al., Gene, 10, 63, 1980), a colony complimentary to the probe derived from the plus tissue but not complimentary to the minus tissue is selected from among the cDNA library as described above. Thus, a plasmid DNA is procured from the colony thus selected, and the base sequence determined according to the dideoxynucleotide method (Messing, J. Methods in Enzymology 101, 20, 1983), etc.

Whether or not these are cDNA's of the peptide C-terminal amidating enzyme can be identified by incorporating the region coding or its amino acid sequence into an expression vector system of E. coli., Bacillul substilis, yeast, animal culture cells, etc., producing the protein coded for by the cDNA, and then assaying the amidating enzyme activity (see e.g., PCT/JP89/00521). The cDNA obtained may be also chosen by comparison of the homology with a known C-terminal amidating enzyme cDNA. Further, a partial amino acid sequence of the enzyme purified by use of the purification method of horse C-terminal amidating enzyme described in International Published Application WO89/12096 may be also determined by a peptide sequencer, etc. and identified to be the same amino acid sequence estimated from the cDNA. Still further, antibodies with the purified enzyme as the antigen may be prepared with rabbit, rat, etc., and then identification may be made by carrying out the antigen-antibody reaction with the protein expressed in E. coli, etc. with the cDNA as described above.

These identification means can be also used as the cDNA cloning method utilizing those characteristics. More specifically, there may be included the method in which among the known different kinds of C-terminal amidating enzyme cDNA's, the region with high homology between those kinds is considered to be also high in the cDNA derived from horse, and the cDNA library DNA is screened as the DNA in such region as the probe; the screening method with the use of an antibody by a cDNA cloning system by use of λgt11 phage as the probe; the screening method of cDNA library of preparing from a part of amino acid sequences of the purified enzyme a synthetic DNA (several kinds) having the codons corresponding thereto by a DNA synthesizer, etc., and preparing this as the probe by use of a plasmid, phage, etc.

The DNA sequence coding for the protein having the peptide C-terminal amidating enzyme activity of the present invention thus prepared can produce the peptide C-terminal amidating enzyme in a large amount by linking its DNA to an appropriate expression vector, thereby expressing the enzyme with E. coli, Bacillus subtilis, yeast, animal cells, etc. as the host.

EXAMPLES

The present invention is described in detail with reference to Examples, which is no way limit, the present invention.

Example 1

Preparation of Gel for Substrate Affinity Chromatography

An amount of 5 ml of Affigel 10 was measured into a 10 ml volume Econocolumn (produced by Biorad) filled with isopropanol. After isopropanol was washed out, the gel was washed with 50 ml of 10 mM sodium acetate buffer (pH 4.5) and then with 10 ml of 0.1M Mops-sodium hydroxide buffer (containing 80 mM calcium chloride, pH 7.5). After the gel was transferred into a bottle of 20 ml volume, it was mixed with 10 ml of the above Mops-sodium hydroxide buffer containing 40 mg (about 100 μmol) of phenylalanyl-glycyl-phenylalanyl-glycine (Phe-Gly-Phe-Gly, produced by Sigma) dissolved therein and a shaking reaction was carried out at 4° C. for 18 hours. Then, 0.5 ml of 1M Tris-HCl buffer (pH 8.0) was added and a shaking reaction was carried out at 4° C. for one hour to deactivate the unreacted active groups. After the gel was washed with the above Mops-sodium hydroxide buffer, then, with deionized water, it was suspended in 0.02% NaN$_3$ filled in a column and stored at 4° C. From the amount of the peptide (Phe-Gly-Phe-Gly) provided for the reaction and the peptide amount in the solution, about 10 μmol per 1 ml of gel was calculated to be bound.

Example 2

Preparation of phenylalanyl-qlycyl-phenylalanyl-hydroxylglycine as Substrate

Figure 1:
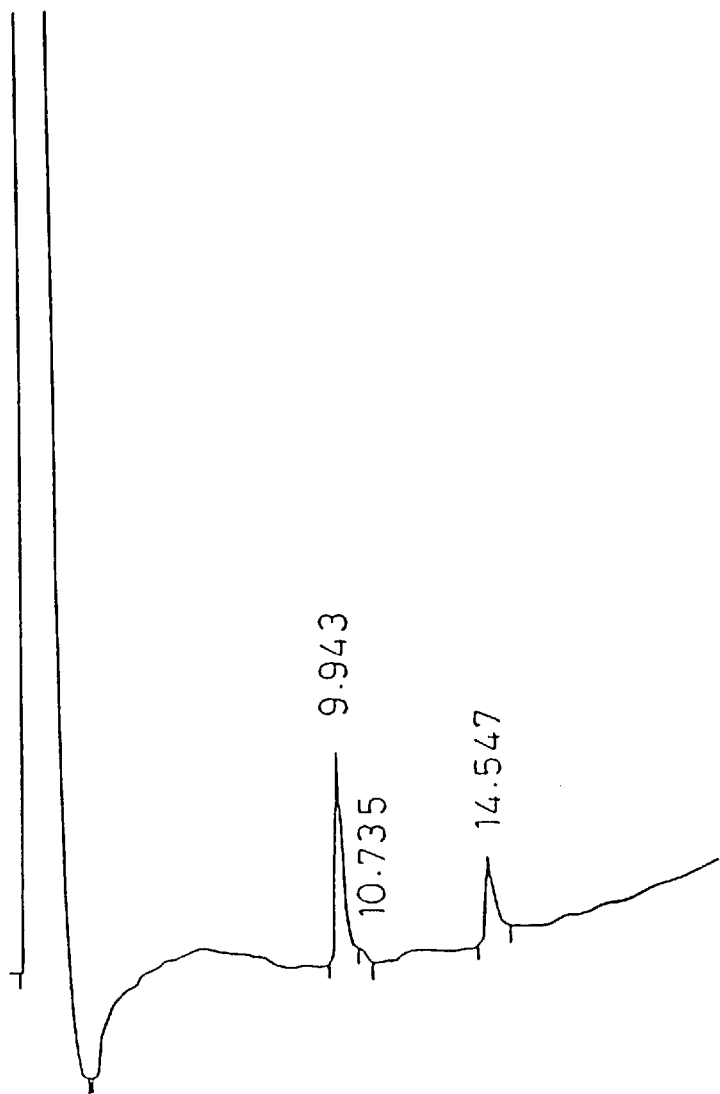
FIG. 1 is an HPLC pattern when preparing FGFhyG by using the enzyme-I of the present invention, with FGFG as the substrate.
Figure 2:
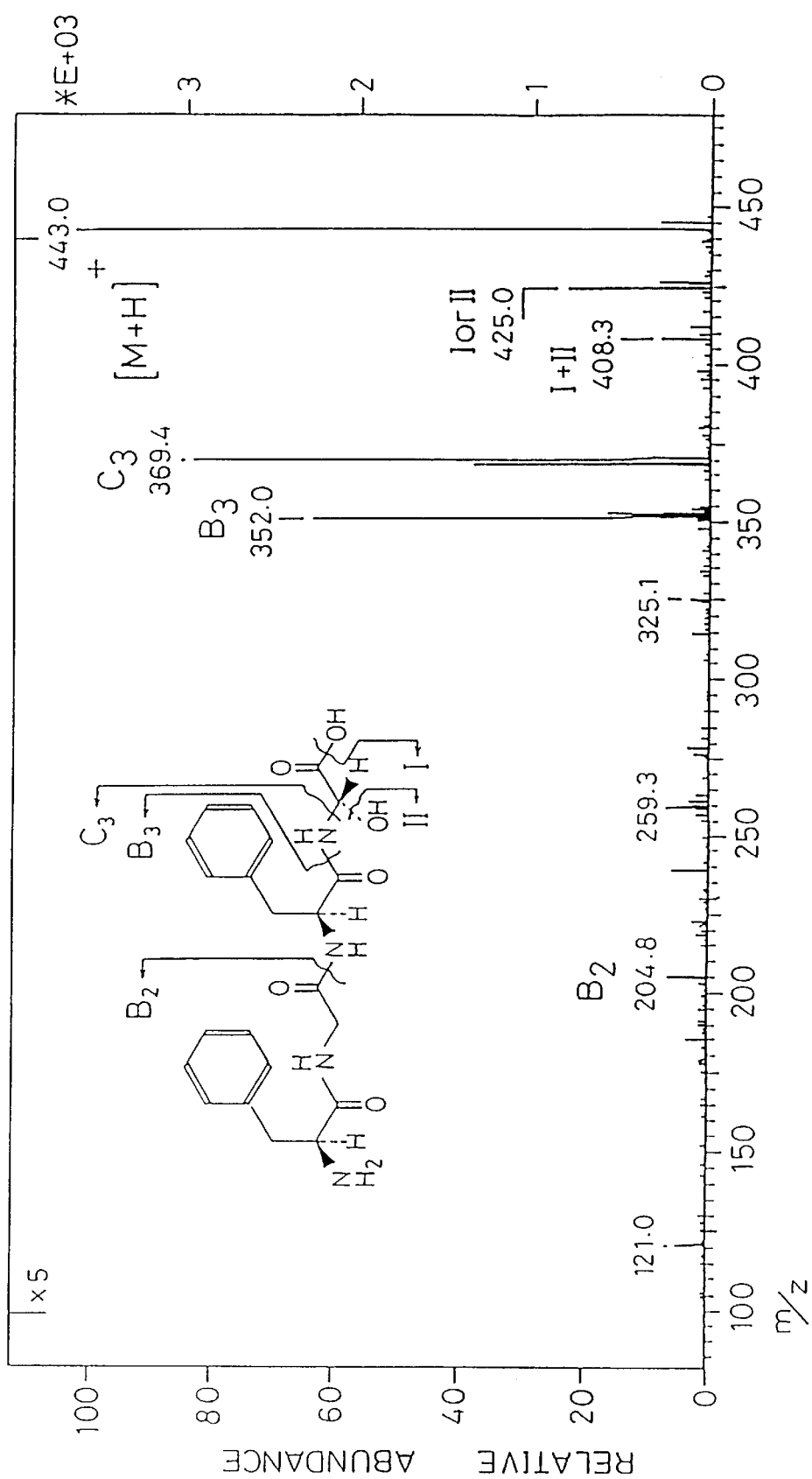
FIG. 2 shows the results of an FAB-MS spectrum analysis conducted for confirmation of the molecular structure of FGFhyG prepared.

An amount of 3 mg of phenylalanyl-glycyl-penylalanylglycine (FGFG) (produced by Sigma) was weighed, and 50 mM Hepes-KOH buffer (pH 5.5), 3 mM ascorbic acid, 10 mM potassium iodide, 0.25 mg/ml catalase, 0.25 mM cupric sulfate, 7.5% acetonitrile and 200 µl of an amidated enzyme composition derived from horse serum as described in Example 2 in International Patent Application JP89-00521 to make up the total amount to 10 ml, followed by aerobic amidation reaction at 30° C. for 20 hours. The reaction was stopped by addition of 10% formic acid, and phenylalanyl-glycyl-phenylalanyl-hydroxylglycine (FGFhyG) was separated by high performance liquid chromatography (HPLC). The column of HPLC used was Capscell Pack C18SG, 300 Å (manufactured by Shiseido). The eluting solvent used was 1 mM ammonium dicarbonate (pH 9.0) and acetonitrile, and a linear gradient of increasing acetonitrile from 0% to 40% for 30 minutes applied. The peptide was detected by the absorption at 214 nm. The results are shown in FIG. 1. The peak of phenylalanyl-glycyl-phenylalanyl-glycine at 10.7 minute was substantially extinguished after the C-terminal amidating reaction. As accompanied therewith, the peaks of the α-hydroxyglycine derivative at 9.9 minute and the amidated compound at 14.5 minute were observed. The structures of these substances were identified by FAB-MS spectrum analysis and NMR analysis. FIG. 2 shows the results of the FAB-MS spectrum in glycerine solution. The parent peak represents the molecular weight of 442, and as the result of its fragmentation, fragments of 425 and 408 m/z with one or two —OH groups existing at C-terminal being cleaved off were identified, thus indicating that it is α-hydroxylglycine adduct. The peak at 9.9 min. was separated, formed swiftly into a 10% formic acid solution, which was then lyophilized to prepare the substrate for the enzyme II of the present invention. The substrate could be similarly prepared even when the enzyme-I containing product of the present invention was used in place of the above amidating enzyme composition. As described above, the α-hydroxylglycine derivative is stable under acidic conditions, but unstable under alkaline conditions and will be decomposed into the amidated compound and glyoxylic acid irrespectively of the enzyme reaction. Therefore, the C-terminal amidation reaction initially conducted in this Example was practiced under acidic conditions. At this time, if the reaction is carried out at pH 7.5 or higher, it becomes impossible to identify the α-hydroxylglycine derivative. The known C-terminal amidating enzyme has been considered to be converted from the C-terminal glycine adduct represented by the formula (I) as described above to the C-terminal amidated compound represented by the formula (III) and glyoxylic acid, because non-enzymatic conversion under the alkaline conditions was included, and the catalytic reaction of the enzyme itself is the conversion reaction from the C-terminal glycine adduct represented by the formula (I) to the C-terminal α-hydroxylglycine adduct represented by the formula (II). Therefore, conversion of the amidating reaction under acidic conditions by the C-terminal amidating enzyme in the prior art has been generally low.

Example 3

Preparation of Enzyme-I from Horse Serum (1) To 100 ml of a commercially available horse serum (produced by Gibco) was gradually added under stirring 100 ml of a 25% aqueous polyethylene glycol 6000 (w/v) (produced by Wako Junyaku), namely to a final concentration of 12.5%. The following operations were all conducted at 4° C. After standing for 12 hours, the mixture was centrifuged (10,000×g, 10 min.) and the resultant precipitates were dissolved in 120 ml of Hepes-potassium hydroxide buffer (pH 7.0). Further after standing for 2 hours, the insoluble substance formed was again removed by centrifugation (10,000×g, 10 min.) to obtain a supernatant containing the C-terminal amidating enzyme activity (127 ml).

Figure 3:
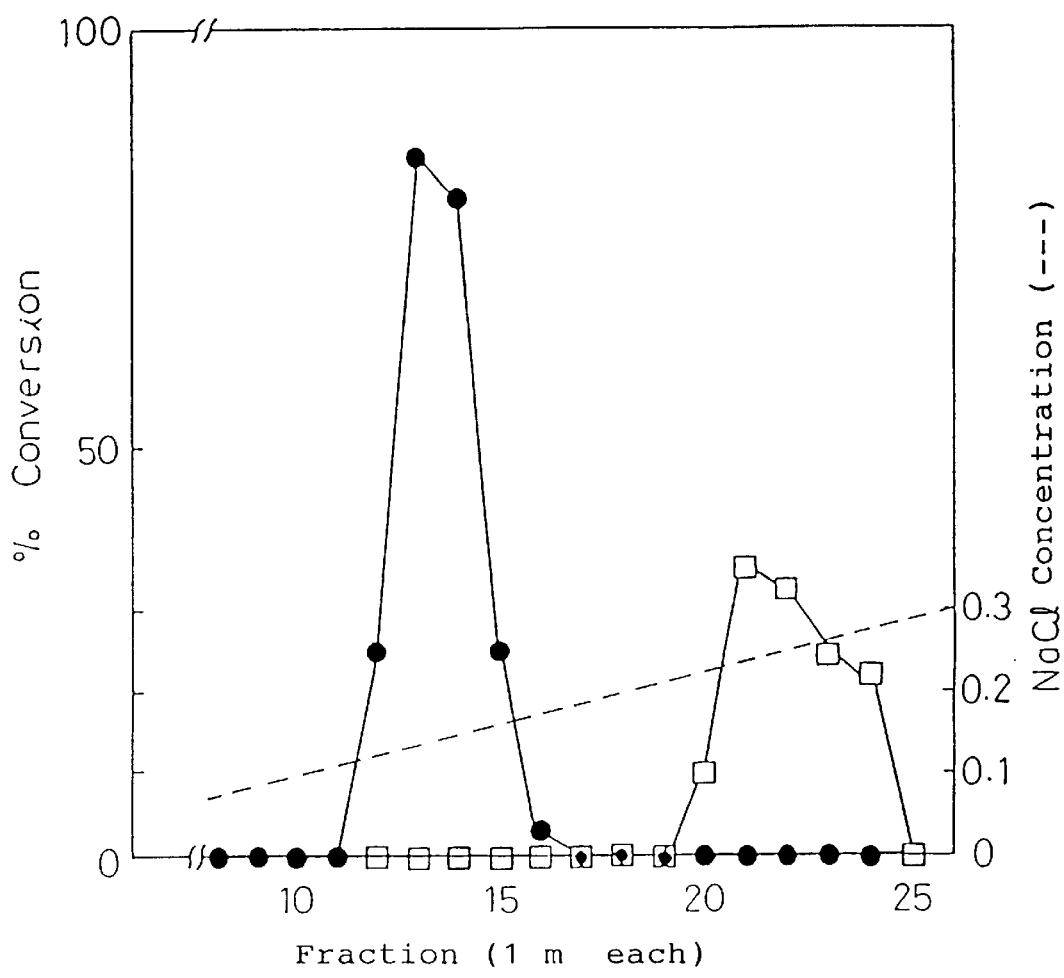
FIG. 3 is a chromatogram pattern showing a separation of the enzyme-I and the enzyme-II of the present invention according to chromatography by a Mono Q column, wherein the open square plots indicate the activity of the enzyme-II, the filled circle plots show the activity of the enzyme-I, and the broken line shows the linear concentration gradient of sodium chloride.

(2) The active fraction obtained in the above (1) was applied to a column (1.6×15 cm) filled with heparin Sepharose CL-6B (produced by Pharmacia) equilibrated with 10 mM Hepes-potassium hydroxide buffer (pH 7.0). After the nonadsorbed substances were washed out with 96 ml of the same buffer, elution was effected with 10 mM Hepes-potassium hydroxide buffer (pH 7.0) containing 0.5M sodium chloride (flow rate 30 ml/hr). FIG. 3 shows the elution pattern. The present enzyme-I was eluted with 0.5M sodium chloride containing buffer [fractions Nos. 14–16 were collected (100 ml)].

(3) The above fractions were subjected to gel filtration by use of Sephadex G-25 Fine (produced by Pharmacia) column chromatography (5 cmφ×23 cm). By use of 10 mM Hepes-KOH (pH 7.0) as the solvent, elution was effected at a flow rate of 2 ml/min. The proteins were detected by absorbance at 280 nm, and 100 ml of fractions containing the proteins was collected.

(4) Affigel 10-Phe-Gly-Phe-Gly gel prepared according to Example 1 in an amount of 5 ml of filled in a column (1.0×6.3 cm), and the column was equilibrated with 10 mM Hepes-potassium hydroxide buffer (pH 7.0) containing 0.1M sodium chloride. To the column was applied the sample (18.1 ml) obtained in the above (3). To ensure that the enzyme-I was adsorbed onto the gel, the liquid passed through the column was circulated many times through the column (flow rate 20 ml/hr). After 12 hours, the circulation was stopped, and the nonadsorbed substances were washed out with 35 ml of the buffer used for equilibration, followed by elution with 8 mM Hepes-potassium hydroxide buffer (pH 7.0) containing 0.4M sodium chloride and 20% acetonitrile (flow rate 20 ml/hr). The enzyme-I activity was recognized only in the eluted fraction (10 ml).

(5) The purified product obtained in the above (4) was subjected against to the treatment (3) as described above, then carried on Mono column (produced by Pharmacia, 0.5×5 cm) equilibrated with 10 mM hepes-potassium hydroxide buffer (pH 7.0), and an NaCl linear concentration gradient was applied in the same buffer as shown in FIG. 3, to elute the proteins. The flow rate at this time was made 0.5 ml/min.

Table 1 shows the total protein amounts, the total enzyme activities, specific activities, yields and purification folds in the respective steps of purification conducted in the above (1) to (5).

TABLE 1

Preparation of enzyme-I from horse serum

| Step | Total protein (mg) | Total activity (U) | Specific activity (U/mg) | Yield (%) | Purification fold |
|---|---|---|---|---|---|
| Serum | 7,500 | 10,500* | 1.4 | 100 | |
| (1) Polyethylene glycol 6000 Precipitation | 4,100 | 9,020 | 2.2 | 86 | 1.6 |
| (2) Heparin Sepharose CL-6B | 1,400 | 5,740 | 4.1 | 55 | 2.9 |
| (3) Sephadex G-25 | 1,100 | 3,960 | 3.6 | 38 | 2.6 |
| (4) Affigel 10-Phe—Gly—Phe—Gly | 2.0 | 800 | 400 | 8 | 290 |
| (5) Mono Q column | 0.5 | 350 | 700 | 3 | 500 |

*Probably because of the influence of the protease existing in the serum, the substrate and product were partially decomposed to give a relatively lower activity.

The activity assay was conducted by practicing the reaction according to the preparation method from FGFG to FGFhyG as described in Example 2 and quantitating FGFhyG by HPLC as described there. The enzyme activity 1 U was defined as the enzyme amount forming 1 nmole of FGFhyG at 37° C. for one hour.

A measurement of the protein amount was conducted by using the improved method of Lowry (Bensadoun et al. Anal. Biochem., 70 265, 1976), and the standard curve was prepared with bovine serum albumin (fraction V, produced by Sigma).

As shown in Table 1, the present enzyme could be purified to about 500-fold with a yield of 2%. When further purification is required, the above-described steps (3) to (5) may be repeated, or either one of those steps may be repeated.

Example 4
Preparation of Enzyme-II from Horse Serum

Horse serum was treated in the same manner as in Example 3 except for performing the respective purification steps while monitoring the activity of the enzyme-II.

Table 2 shows the total proteins, the total enzyme activities, specific activities, yields and purification folds in the respective purification steps (1) to (5).

TABLE 2

Preparation of enzyme-II from horse serum

| Step | Total protein (mg) | Total activity (U) | Specific activity (U/mg) | Yield (%) | Purification fold |
|---|---|---|---|---|---|
| Serum | 7,500 | 2,100* | 0.28 | | |
| (1) Polyethylene glycol 6000 Precipitation | 4,000 | 5,300 | 1.3 | 250 | 4.6 |
| (2) Heparin Sepharose CL-6B | 1,500 | 3,800 | 2.5 | 180 | 9.0 |
| (3) Sephadex G-25 | 1,200 | 3,000 | 2.5 | 140 | 9.0 |
| (4) Affigel 10-Phe—Gly—Phe—Gly | 1.2 | 360 | 300 | 17 | 1070 |
| (5) Mono Q column | 0.1 | 50 | 500 | 2 | 1790 |

*Probably because of the influence of the protease existing in the serum, the substrate and product were partially decomposed to give a relatively lower activity.

Activity assay was carried out at 30° C. by dissolving the phenylalanyl-glycyl-phenylalanyl-hydroxylglycine (FGFhyG) obtained in Example 1 in 10 mM hepes-potassium hydroxide (pH 6.5) to 5 mM concentration, adding the samples at the respective steps, and making up the total amount to 100 ml. After the reaction for one hour, the reaction was stopped by addition of 10% formic acid, and the reaction product was quantitated by HPLC using the conditions of Example 2. At this time, the reaction of Control with no addition of the sample was also conducted to confirm that substantially no non-enzymatic conversion proceeded. The HPLC pattern of the reaction mixture is shown in FIG. 4 (the reaction conditions in the Figure are 37° C., pH 6.9, with the reaction time being indicated in the Figure), and the activity represented in unit (U). 1 U is defined as the enzyme amount which forms 1 nmole of FGF-$NH_2$ at 30° C. for one hour.

Measurement of the protein mass was carried out in the same manner as in Example 3.

As shown in Table 2, the present enzyme could be purified to about 1800-fold with a yield of 2%.

In the following Examples, production of said enzyme utilizing a peptide C-terminal amidating enzyme cDNA derived from rat pituitary is described, but the present invention is not limited thereby.

Example 5
Construction of Expression Plasmid

Figure 7:
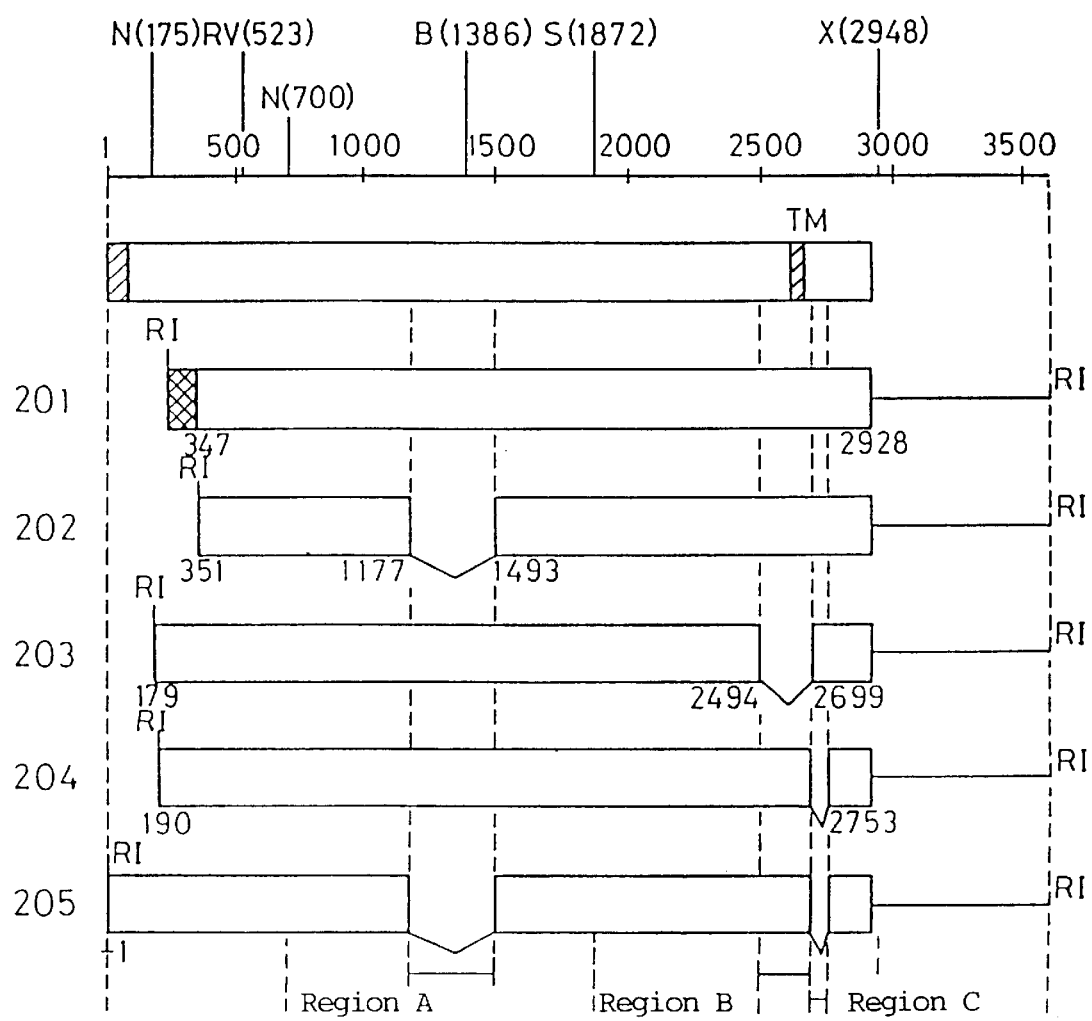
FIG. 7 schematically shows the five C-terminal amidating enzymes cloned from the rat pituitary mRNA, wherein the region coding for the enzyme estimated is shown by boxes. The numerals indicate the base numbers (bp) with the translation initiation point being made 1, TM represents the portion corresponding to the membrane-transport region, KK represents the lysine—lysine sequence, and the restriction endonucleases are shown by the following abbreviations, respectively.

By use of the poly-$A^+$RNA derived from rat pituitary, 5 cDNA clones were obtained (see FIG. 6, FIG. 7, Seikagaku, 61, 842 (1989)).

The DNA fragment of 2.58 kbp (kilobase pairs) of the cDNA clone 205 cleaved by EcoRI-XmaI was inserted into an expression vector of an animal culture cell system, pSV2 vector [S. Subramani, R. Mulligan, P. Berg, Mol. Cell. Biol. 1, 854 (1981)] via a synthetic linker at the HindIII-BglII, and the plasmid was designated as SV-205. Next, the NsiI(700)—XmaI fragment of SV-205 was replaced with the respective NsiI(700)—XmaI fragments of cDNA clones 201, 202, 203, 204. These expression plasmids were called SV-201, SV-202, SV-203, SV-204. The SV-203 DNA was deleted the DNA region coding trans membrane domain. From the SV-203 plasmid DNA this obtained, an expression plasmid SV-A which expresses an enzyme by acting on a C-terminal glycine adduct according to the present invention to convert it to a C-terminal α-hydroxylglycine adduct was constructed. The DNA portion of the BamHI site [FIG. 7 B (1386)] existing in the vicinity of the cDNA region coding for the KK sequence portion around the center was deleted by digestion with BamHI, XmaI [FIG. 7 X (1948)], and a synthetic linker:

5'-CATCTGAAAC-3'
3-ACTTTGGGCC-5' was inserted into the cleaved site, ligation was effected, followed by completion of the SV-A plasmid. The synthetic DNA was synthesized in conventional manner by use of a DNA synthesizer produced by ABI and purified. The synthetic DNA is constituted of the BamHI cleaved site-stop codon-XmaI cleaved site.

Next, an expression plasmid SV-B according to the present invention which expresses an enzyme for converting a C-terminal α-hydroxylglycine adduct to a C-terminal amidated compound and glyoxylic acid was constructed. The SV-203 DNA was cleaved at the KpnI site [FIG. 7, N (175)] existing immediately downstream of the region coding for the signal peptide and the BamHi site existing at the position corresponding to the vicinity of the KK site at the center, and linked in between thereof with a synthetic DNA:

5'-GATCGTAC-3'
3'-CATGCTAG-5' to form an expression plasmid SV-B. As the result, the signal peptide region were combined with the cDNA latter part site in reading frame.

Example 6
Expression in Animal Culture Cells

The cultured cell COS-7 was grown in a synthetic medium (DMEM) containing a 10% fetal bovine serum and transformed by use of the expression plasmid of Example 5 according to the known method (see C. Chen and H. Okayama, Mol. Cell. Biol. 7, 2745 (1987)). In the transformation, 20 μg of the expression plasmid was employed per 5×10⁵ cells. After cultivation under the conditions of 3% carbon dioxide, 35° C. for 24 hours, the cells were washed twice with 10 ml of a DMEM medium containing 0.2% bovine serum albumin (BSA), and then further cultured in 10 ml of the DMEM medium containing 0.2% BSA under the conditions of 5% carbon dioxide and 37° C. for 48 hours.

Example 7
C-terminal Amidating Enzyme Activity Produced by the Recombinant Cells The cell culture broth expressed in Example 6 was separated by centrifugation into cells and supernatant (medium).

For the supernatant, enzyme activity was assayed. Assay of the activity was carried out following basically the method by use of HPLC shown in a literature (J. Biol. Chem. 265, 9602–9605). Shortly speaking, the conversion activity of the C-terminal glycine adduct to the α-hydroxylglycine adduct was determined by permitting the reaction to proceed with the reaction composition (A) as shown below and quantitating the substrate (PheGlyPheGly) and the product (PheGlyPhehydroxyGly) after a certain time of the reaction.

Reaction composition (A):
15 μM PheGlyPheGly
5 mM $CuSO_4$
5 μl/reaction mixture 1 ml Catalase (Sigma)
100 mM MES buffer (pH 5.6)
1 mM Ascorbic acid
+ Culture supernatant (medium)

The converting activity of the α-hydroxylglycine adduct to the amidated compound and glyoxylic acid was assayed similarly by use of the following reaction composition (B).

Reaction composition (B):
15 μM PheGlyPhehydroxyGly*
100 mM MES buffer (pH 5.6)
+ Culture supernatant (medium)

* The reaction was permitted to proceed in the reaction composition (A), and prepared from the α-hydroxylglycine adduct separated by HPLC.

The assay results are shown in Table 3.

TABLE 3

| | | Enzyme activity n mole/h/ml medium | |
| --- | --- | --- | --- |
| | | Substrate | |
| | | PheGlyPheGly | PheGlyPhehydroxyGly Product |
| Plasmid | | PheGlyPhe-hydroxyGly | PheGlyPhe—$NH_2$ + Glyoxylic acid |
| SV-203 | (Signal sequence + N-terminal domain + C-terminal domain; present invention) | 2.5 | 4.2 |
| SVa | (Signal sequence + N-terminal domain; present invention) | 2.8 | <2 |
| SVb | (Signal sequence + C-terminal domain; present invention) | 0.4 | 10.8 |
| PSV2 | (Control) | 0.3 | <2 |
| NO Plasmid | (Control) | 0.5 | <2 |

In medium of the transformant with the SV-a plasmid, a markedly improved α-hydroxylglycine adduct producing activity was recognized, and it did not participate in the reaction with the α-hydroxylglycine adduct as the substrate. In contrast, in the strain transformed with the SV-b plasmid, no reaction occurred at all on the C-terminal glycine adduct, but only an activity of converting the α-hydroxylglycine adduct to the amidated compound was recognized. In the strain transformed with the plasmid SV-203 having substantially the whole region of the cDNA, both enzyme activities were recognized, but the respective enzyme activities were lower as compared with SV-a, SV-b.

Next, whether or not the enzyme expressed in these transformed strains is single was confirmed by gel filtration chromatography. By the use of a Sephacryl S-200 (produced by Pharmacia) column (1×95 cm), the column was equilibrated with an elution buffer 10 mM HEPES-KOH (pH 7.0), 50 mM NaCl. The elution rate was 6 ml/hour, and 1 ml fractions were collected. The results of the both enzyme activities and the protein masses assayed are shown in FIG. 8 to FIG. 10. The enzyme activities derived from SV-a (FIG. 8) and from SV-b (FIG. 9) became respectively the single peaks, and also the molecular weights assayed were found to be 36 kDa, and 54 kDA, corresponding to the molecular weights of the proteins coded for by the cDNA's possessed by the respective plasmids. However, the protein derived from SV-203 plasmid, as shown in FIG. 10, was separated into the two peaks of the activity for producing the α-hydroxylglycine adduct (□—□) by acting on the C-terminal glycine and the activity for producing the amidated compound and glyoxylic acid (○—○) by acting on the α-hydroxylglycine adduct. Besides, these molecular weights were found to be the same as those of the respective enzymes shown in FIG. 8, FIG. 9 expressed solely. This result showed that the KK sequence positioned at the central portion of the protein coding for the cDNA was cleaved by processing the culture cells. Therefore, it was shown that the two kinds of enzymes according to the present invention can be also produced by expression of the cDNA having such whole cDNA region.

Next, the synergetic effect by using the two kinds of enzymes in the present invention in the C-terminal amidating reaction was shown by use of FIG. 11 and FIG. 12. FIG. 11 and FIG. 12 show the change in conversion of amidated compound with a lapse of time when PheGlyPheGly was employed as the substrate. The enzyme samples were prepared by purifying the medium supernatants obtained by expression of SV-a, SV-b plasmids by the gel filtration as described above, and concentrating the respective active fractions. FIG. 11 shows one derived from SV-a, which shows that only the α-hydroxyl adduct is produced with no amidated compound being produced. FIG. 12 shows the case when using only the enzyme derived from SV-b (☆), and the case when using those derived from SV-a and SV-b in combination. It was shown that none of the α-hydroxyl adduct and the amidated compound were produced at all with only the enzyme derived from SV-b, while both the α-hydroxyl adduct and the amidated compound could be produced well by using the both enzymes in combination (the amounts of the enzymes added were the same). Note, the reaction efficiency is increased when they were used after 4 hours or later, and after the reaction for 9 hours, a conversion as high as 1.5-fold is obtained compared with the case of use of only the enzyme derived from SV-a shown in FIG. 11. Thus, the use of both enzymes proved to be a very effective means for carrying out the C-terminal amidating reaction.

Example 8
Preparation of poly-A$^+$RNA from Horse Heart Atrium (1) Preparation of whole RNA Horse heart atrium after enucleation was minced swiftly, and about 2 g thereof was placed in a 50 ml plastic tube (No. 2070, produced by Falcon) and freezed in liquid nitrogen. An amount 20 ml of guanidine thiocyanate solution (4M guanidine thiocyanate, 25 mM sodium citrate (pH 7.0), 0.5% laurylsarcosine sodium, 0.1% Antifoam A, 0.1M 2-mercaptoethanol) were added, and the cells were crushed by means of Polytron (Central Kagaku Boeki), followed by take-out and introduction of the crushed liquor by a 10 ml syringe (produced by Terumo Co., Ltd.) equipped with an 18 G injection needle. The sedimentation was removed by a low speed centrifugation (300×g, 5 minutes), and 7.3 ml of the supernatant was overlaid in a 3.7 ml CsTFA vessel (produced by Pharmacia, aqueous cesium trifluoroacetic acid containing 0.5M EDTA, adjusted to a density of 1.64 g/ml) and treated by a ultra-centrifugation machine by use of a swing rotor RPS-40T (produced by Hitachi Seisakusho, SCP85H) at 33,000 rpm for 16 hours. The precipitates were washed with 3 ml of 4M guanidine solution, then with 3 ml of 95% ethanol and thereafter dissolved in 1.5 ml CsTFA solution. To the solution were added 60 μl of 5M NaCl Solution, 3.9 ml of ethanol, and ethanol precipitation was effected at −80° C. for 30 minutes, followed by centrifugation at 16,000×g for 15 minutes to obtain precipitates. The precipitates were washed with 70% ethanol, and then dried by a concentrator (produced by Sakuma Seisakusho, EC-57C). After dissolved in sterilized distilled solution, absorbance at 260 nm was measured to quantitate the RNA amount. According to this method, 350 μg of RNA could be obtained from about 2 g of a horse heart atrium tissue.

(2) Preparation of poly-A$^+$ RNA

Preparation of a poly-A$^+$RNA from the whole RNA was carried out by use of "mRNA Purification Kit" (produced by Pharmacia) according to the accompanying protocol. Affinity chromatography was carried out twice by an oligo(dT) column to obtain 13 μg of a poly-A$^+$RNA from 350 μg of a horse heart atrium whole RNA.

Example 9
Preparation of cDNA Library (1) Preparation of cDNA

By the use of "cDNA Synthesis System Plus" (RPN1256Y, produced by Amersham), cDNA synthesis was carried out by the use of 5 μg of a horse heart atrium poly-A$^+$RNA. The synthesis procedure followed faithfully the accompanying protocol. As the primer, an oligo-dT nucleotide was employed, and the cDNA synthesis efficiency was calculated from the radio-activity according to a synthetic system containing [α-$^{32}$P]-dCTP. As the result, the reverse transcription efficiency was found to be about 20%, and the second strand synthesis efficiency 90% or higher.

(2) Preparation of cDNA library

By use of "cDNA Cloning System λgt10, version 2.0" (RPN 1257, produced by Amersham) for linking to the phage DNA, and "Gigapack;Gold" (produced by Stratagene) for packaging into the phage, a cDNA library was prepared from the synthetic cDNA according to the accompanying protocols of these.

(3) Infection of *E. coli*

As the host microorganism, *E. coli* Y1089 (ATCC37196) was employed, and the competent cells were prepared as described below. Single colony cells were inoculated into 5 ml of an NZY medium (0.5% NaCl, 1% NZ amine, type A (Wako Junyaku), 0.5% yeast extract (DIFCO), 0.2% magnesium sulfate, pH 7.5) added with 0.2% maltose, and shaking cultivation was carried out at 37° C. overnight. An amount of 100 μl of the culture broth was transplated into 5 ml of the same fresh medium, and after culturing at 37° C. to OD$_{660}$=0.5, the microorganisms were collected by centrifugation. The competent cells were prepared by suspending the cells in 1 ml of a 10 mM magnesium sulfate solution.

To 0.2 ml of the competent cell suspension was added 0.1 ml of the phage solution prepared in (2), and the mixture was mixed with 3 ml of top agarose (NZY medium containing 0.7% type I-LowEEO-agarose (produced by Sigma)) maintained at a temperature of 56° C., followed by casting into the upper part of an NZY agar plate (30 ml of NZY medium containing 1.5% Bactoagar (produced by DIFCO) added to the 1005 Plate produced by Falcon). After solidifcation of top agarose, stationary cultivation was carried out at 37° C. overnight. By identifying the plaques, the phage-infected cells were identified.

According to the method as described above, a horse heart atrium cDNA library containing $2.0 \times 10^7$ independent phage.

Example 10

Isolation of C-terminal Amidating Enzyme cDNA (1) Preparation of DNA probe

A peptide C-terminal amidating enzyme cDNA derived from rat has been already isolated, and its sequence reported (D. A. Soffer et. al., Proc. Natl. Acad. Sci. USA, 86, 735–739 (1989), Kato et. al., Seikagaku, 61, 842 (1989)). The present inventors considered that there is homology to some extent between the rat cDNA and the C-terminal amidating enzyme cDNA derived from horse, procured a part of the rat cDNA and progressed isolation of the horse cDNA with the use of this as the probe. The rat cDNA was gifted from Tohoku University, School of Medicine (Kato et. al., Seikagaku, 61, 842 (1989)), which was digested with restriction endonucleases EcoRI and HincII as well as Nsi I and Sph I, whereby the DNA fragments shown in FIG. 14 and FIG. 15 were respectively isolated, followed by $^{32}$P labelling by Multiprime DNA Labelling Kit (produced by Amersham) to provide a probe.

(2) Plaque hybridization

According to the method shown in the infection of E. coli in Example 9 (3) about 500,000 plaques were formed per one sheet of a plate of 15 cm in diameter (No. 1058, produced by FALCON). The cultivation for plaque formation was carried out at 37° C. for 4 hours. After the plate was left to stand at 4° C. for 2 hours, a nitrocellulose filter (BA85, produced by Schleicher & Schuell) was adhered to have the phage DNA migrated to the filter, and then the DNA was denatured in an alkaline solution (0.5M caustic soda, 1.5M sodium chloride). After neutralization with a neutralizing solution (1.5M sodium chloride, 0.5M Tris-HCl buffer, pH 7.0), the mixture was rinsed with a 2×SSC solution (0.3M sodium chloride, 30 mM sodium citrate buffer pH 7.0), and after air drying heated at 80° C. for 2 hours under a reduced pressure, followed by fixing of the DNA onto the filter.

For the nitrocellulose filter having the phage DNA fixed thereon, plaque hybridization was effected by use of the probe prepared in (1). The filter was placed in Lappybag (produced by Iwatani), and 30 ml of a prehybridization liquor (0.75M sodium chloride, 50 mM sodium phosphate buffer, pH 7.4, 5 mM EDTA, 0.05% Ficoll, 0.05% polyvinyl pyrrolidone, 0.05% bovine serum albumin (fraction V, produced by Sigma), 0.1% SDS, 0.2 mg/ml salmon sperm DNA) was added, followed by sealing of the bag by a sealer and heating at 65° C. for 4 hours. The prehybridization liquor was discarded, and 30 ml of a hybridization solution (0.75M sodium chloride, 50 mM sodium phosphate buffer, pH 7.4, 5 mM EDTA, 0.02% Ficoll, 0.02% polyvinyl pyrrolidone, 0.02% bovine serum albumin, 0.1% SDS, 0.1 mg/ml salmon sperm DNA having about $1.0 \times 10^7$ cpm of the radioactivities was added, and after sealing, hybridization was effected at 65° C. for 15 hours. The filter was washed twice with 250 ml of a washing solution (0.3 mM sodium chloride, 20 mM sodium phosphate buffer, pH 7.4, 2 mM EDTA, 0.1% SDS) and further twice with 250 ml of a washing solution (30 mM sodium chloride, 2 mM sodium phosphate buffer pH 7.4, 0.2 mM EDTA, 0.1% SDS) and dried on air. The positive clone was detected by autoradiography by an X-ray film (Fuji, HR-H) under the exposure conditions at −80° C. overnight.

For the two probes employed, 2,000,000 plaques were respectively screened, and about 1000 positive clones were obtained. The phage DNA was recovered from the positive plaques, and again E. coli was effected therewith according to the method as described above, and plaque hybridization practiced again, which operations were repeated until the plaque became single. Ordinarily, single plaques can be obtained by repeating the operations twice.

Example 11

Determination of cDNA Base Sequence

According to the method described on pages 371–372 in Molecular Cloning A Laboratory Manual (T. Maniatis, E. F. Fritsch, J. Sambrook, editors, Cold Spring Harbor Laboratory, 1982), DNA was separated and purified from the phage cloned. The DNA was digested with a restriction enconuclease EcoRI (produced by Takara Shuzo), and the cDNA insertion DNA fragment was separated from the phage DNA according to 1.5% Agarose gel electrophoresis. The cDNA fragment was extracted from the gel, and incorporated at the EcoRI site of the E. coli plasmid pUC 119 (produced by Takara Shuzo) by the ligation reaction. When the EcoRI site exists in the cDNA fragment, the cDNA fragment was obtained by partial digestion of the phage DNA with EcoRI. After the plasmid was amplified, the cDNA fragment was subcloned with M13 phages mp 18, mp 19 (produced by Takara Shuzo), to obtain a single-stranded DNA following conventional procedures. By the use of Sequenase (trade name, produced by Toyo Boseki K. K.) following the instructions thereof, the DNA base sequence was determined. The base sequence of single-stranded DNA was determined for about 400 bases, and for the DNA fragment with a length exceeding that length, the sequence was determined by subcloning by the use of an appropriate restriction endonuclease. For the cDNA fragment, the base sequences of both chains of the double-strand were determined.

FIGS. 13(A)–13(F) show the horse C-terminal amidating enzyme cDNA base sequence determined (this base sequence shows the longest cDNA as the result of many analyses of cDNA) and the amino acid sequence (one letter representation) expected from the base sequence. Also, cDNA's in which one or both of the portions shown by [ ] in the Figure were deficient could be confirmed. These cDNA's are considered to be derived from mRNA's by different mRNA splicing methods.

INDUSTRIAL APPLICABILITY

The present invention can be utilized for producing a peptide C-terminal amidation compound from the corresponding peptide C-terminal glycine adduct. Such a peptide C-terminal amidation compound includes valuable physiologically active substances.

We claim:

1. A purified enzyme participating in C-terminal amidation which acts on a peptide C-terminal glycine adduct represented by the following formula (I):

(I)

wherein A represents a residue excluding α-amino or imino group and α-carboxyl group derived from naturally occurring α-amino acid, X represents hydrogen atom or a residue of an amino acid derivative which is bonded to the N atom through a carbonyl group to form a peptide C-terminal α-hydroxyglycine adduct represented by the following formula (II):

$$\overset{(H)}{\underset{|}{X-N}}-A-CONH\overset{OH}{\underset{|}{C}}HCOOH \qquad (II)$$

wherein A and X have the same meanings as above, but which enzyme does not convert the peptide C-terminal α-hydroxyglycine adduct (II) to a C-terminal amidated compound represented by the following formula (III):

$$\overset{(H)}{\underset{|}{X-N}}-A-CONH_2 \qquad (III)$$

wherein A and X have the same meanings as defined above.

2. The enzyme according to claim 1, wherein
(a) the enzyme has an optimum pH of about 5 to 7, and a stable pH of 4 to 9,
(b) the enzyme has an optimum temperature of 25° to 40° C., and
(c) metal ions and ascorbic acid act as a cofactor for the enzyme.

3. The enzyme according to claim 1, wherein the enzyme has a molecular weight of about 25 kDa or about 36 kDa.

4. The enzyme according to claim 1, which has an amino acid sequence corresponding to the amino acid sequence selected from the amino acid sequences from the 42th residue, P or S to the 442th residue, K of human, horse, bovine and rat or corresponding to the amino acid sequence from the 42th residue P or S to the 231th residue K of horse or bovine as shown in the accompanying FIG. 5.

5. A method of preparing a C-terminal α-hydroxylglycine adduct represented by the above formula (II), which comprises treating a C-terminal glycine adduct represented by the above formula (I) with an enzyme according to claim 1.

6. A method of assaying the activity of the enzyme of claim 1 comprising:
(a) buffering a test sample expected to have the activity of an enzyme according to claim 1 to pH 5 to 8;
(b) adding to the resultant buffered sample a peptide C-terminal glycine adduct represented by the above formula (I), L-ascorbic acid and catalase followed by incubation; and
(c) detecting a peptide C-terminal α-hydroxylglycine adduct represented by the formula (II) isolated by HPLC using an acetonitrile containing an eluant of pH 6 to 10.

7. A method for preparing an enzyme participating in peptide C-terminal amidation according to claim 1, comprising the steps of:
(1) subjecting a material containing the enzyme to a substrate affinity chromatography using as a ligand the peptide C-terminal glycine adduct represented by the formula (I),
(2) subjecting the product from the step (1) to an anion exchange chromatography, and
(3) recovering a purified enzyme from the product of step (2) via an assay using a peptide C-terminal glycine adduct as a substrate.

8. The method of claim 7, wherein said ligand is a peptide in a free state or bound to a water-insoluble carrier through the amino group of the amino acid residue at the N-terminal and selected from the group consisting of D-Tyr-Trp-Gly, Phe-Gly-Phe-Gly and Gly-Phe-Gly.

9. The method of claim 7, wherein the material containing the enzyme is a homogenate of an organ selected from the group consisting of mammal brains, pituitary glands, mammal heart and mammal blood.

10. The method of claim 7, wherein the material containing the enzyme is horse serum.

11. A purified enzyme participating in peptide C-terminal amidation of a C-terminal glycine adduct which acts on a peptide C-terminal α-hydroxyglycine adduct represented by the above formula (II):

$$\overset{(H)}{\underset{|}{X-N}}-A-CONH\overset{OH}{\underset{|}{C}}HCOOH \qquad (II)$$

wherein A represents a residue excluding α-amino or imino group and α-carboxyl group derived from naturally occurring α-amino acid, X represents hydrogen atom or a residue of an amino acid derivative which is bonded to N atom through carbonyl group to form a C-terminal amidated compound represented by the following formula (III):

$$\overset{(H)}{\underset{|}{X-N}}-A-CONH_2 \qquad (III)$$

wherein A and X have the same meanings as defined above, but which enzyme does not convert a peptide C-terminal glycine adduct represented by the following formula (I):

$$\overset{(H)}{\underset{|}{X-N}}-A-CONHCH_2COOH \qquad (I)$$

wherein A and X have the same meaning as above to said peptide C-terminal α-hydroxyglycine adduct (II).

12. The enzyme according to claim 11, wherein
(a) the enzyme has an optimum pH of about 5 to 6, and a stable pH of 4 to 9, and
(b) the enzyme has an optimum temperature of from 15° to 35° C.

13. The enzyme according to claim 11, wherein the enzyme has a molecular weight of about 40 kDa or about 43 kDa.

14. The enzyme according to claim 11, which has an amino acid sequence corresponding to the amino acid sequence selected from the amino acid sequences from the 443th residue P or S to the 830th residue K of human, horse, bovine and rat as shown in the accompanying FIG. 5.

15. A method of preparing a C-terminal amidated compound represented by the above formula (III), which comprises treating a C-terminal α-hydroxylglycine adduct represented by the above formula (II) with an enzyme according to claim 11.

16. A method of assaying the activity of the enzyme of claim 11 comprising:
(a) buffering a test sample expected to have the activity of an enzyme according to claim 11 to pH 4 to 8;
(b) adding to the resultant buffered sample a peptide C-terminal glycine adduct represented by the above formula (II) followed by incubation; and
(c) detecting a C-terminal amidated compound represented by the formula (III) formed.

17. A method for preparing an enzyme participating in peptide C-terminal amidation according to claim 11, comprising the steps of:
(1) subjecting a material containing the enzyme to a substrate affinity chromatography using as a ligand the peptide C-terminal glycine adduct represented by the formula (I),
(2) subjecting the product from the step (1) to an anion exchange chromatography, and
(3) recovering a purified enzyme from the product of step (2) via an assay using a peptide C-terminal hydroxyglycine adduct as a substrate.

18. The method of claim 17, wherein said ligand is a peptide in a free state or bound to a water-insoluble carrier through the amino group of the amino acid residue at the N-terminal and selected from the group consisting of D-Tyr-Trp-Gly, Phe-Gly-Phe-Gly and Gly-Phe-Gly.

19. The method of claim 17, wherein the material containing the enzyme is a homogenate of an organ selected from the group consisting of mammal brains, pituitary glands, mammal heart and mammal blood.

20. The method of claim 17, wherein the material containing the enzyme is horse serum.

* * * * *

UNITED STATES PATENT AND TRADEMARK OFFICE
CERTIFICATE OF CORRECTION

PATENT NO. : 5,871,995
DATED : Februrary 16, 1999
INVENTOR(S) : Toshii Iiada, et al.

It is certified that error appears in the above-identified patent and that said Letters Patent is hereby corrected as shown below:

Column 14, line 54, delete "FIGS. 5(A)-5(B)" and insert --FIGS. 5(A)-5(F)--.

Column 44, line 49, delete "FIGS. 13(A)-13(F)" and insert --FIGS. 13(A)-13(P)--.

Signed and Sealed this

Fifteenth Day of June, 1999

Q. TODD DICKINSON

*Attest:*

*Attesting Officer*         Acting Commissioner of Patents and Trademarks

UNITED STATES PATENT AND TRADEMARK OFFICE
CERTIFICATE OF CORRECTION

PATENT NO. : 5,871,995
DATED : February 16, 1999
INVENTOR(S) : Toshii IIDA et al.

It is certified that error appears in the above-identified patent and that said Letters Patent is hereby corrected as shown below:

On the title page, Item [22], PCT Filed, delete "April 12, 1990" and insert "--August 14, 1990-- and Item [30] Foreign Application Priority Data, the second priority application date, delete "October 19, 1989" and insert --October 31, 1989--.

Signed and Sealed this

Thirty-first Day of August, 1999

*Attest:*

Q. TODD DICKINSON

*Attesting Officer*  *Acting Commissioner of Patents and Trademarks*

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 631 base pairs
        ( B ) TYPE: nucleic acid
        ( C ) STRANDEDNESS: single
        ( D ) TOPOLOGY: linear ( i i ) MOLECULE TYPE: DNA (genomic)

( v i ) ORIGINAL SOURCE:
        ( A ) ORGANISM: rat ( x i ) SEQUENCE DESCRIPTION: SEQ ID NO:1:

```
ATGGCCGGAC   GCGCCCGCAG   CGGTCTGCTA   CTGCTGCTGC   TCGCCCTGCA   TCGCCCTGCA      60
GACCAGCTGC   CTGGCCTTCA   GAAGCCCACT   TTCTGTCTTT   AAGAGGTTTA   AAGAAACTAC     120
CCAGATCATT   TTCCAATGAA   TGCCTTGGTA   CCATTGGACC   AGTCACCCCT   CTTGATGCAT     180
CAGATTTTGC   GCTGGATATT   CGCATGCCTG   GGGTTACACC   TAAAGAGTCT   GACACATACT     240
TCTGCATGTC   CATGCGTCTG   CCTGTGGATG   AGGAAGCTTC   GTGATTGACT   TCAAGCCTCG     300
TGCCAGCATG   GATACTGTCC   ACCATATGCT   GCTGTTTGGA   TGCAATATGC   CCTCGTCCAC     360
TGGAAGTTAC   TGGTTTTGTG   ATGAAGGAAC   CTGTAAACAG   ATAAAGCCAA   TATTCTATAT     420
GCCTGGGCAA   GGAATGCTCC   CCCACCCGGC   TCCCGAAAGG   TGTTGGATTC   AGATTGGAGG     480
AGAAACTGGA   AGCAAATACT   TCGTCCTTCA   AGTTCACTAT   GGCGATATCA   GTGCTTTTCG     540
AGATAATCAC   AAAGACTGCT   CTGGCGTGTC   CGTACATCTC   ACACGTGTGC   CCCAGCCTTT     600
AATTGCGGGC   ATGTACCTTA   TGATGTCTGT   T                                       631
```

( 2 ) INFORMATION FOR SEQ ID NO:2:

( i ) SEQUENCE CHARACTERISTICS:
        ( A ) LENGTH: 6638 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Horse ( i x ) FEATURE:
        ( A ) NAME/KEY: CDS
        ( B ) LOCATION: 11..3070

( x i ) SEQUENCE DESCRIPTION: SEQ ID NO:2:

```
CGGCGTGGAC   ATG   GCT   GGC   CTT   CGT   AGC   CTG   CTA   GTT   CTC   CTC   CTT   GTT        49
             Met   Ala   Gly   Leu   Arg   Ser   Leu   Leu   Val   Leu   Leu   Leu   Val
              1                 5                             10

TTT   CAG   AGC   AGC   TGT   TTG   GGT   TTC   AGA   AGC   CCA   CTT   TCT   GTC   TTT   AAG    97
Phe   Gln   Ser   Ser   Cys   Leu   Gly   Phe   Arg   Ser   Pro   Leu   Ser   Val   Phe   Lys
       15                      20                       25

AGG   TTT   AAA   GAA   ACT   ACC   AGA   CCA   TTT   TCC   AAT   GAA   TGT   CTT   GGT   ACC   145
Arg   Phe   Lys   Glu   Thr   Thr   Arg   Pro   Phe   Ser   Asn   Glu   Cys   Leu   Gly   Thr
 30                       35                       40                             45

ACC   AGA   CCA   GTC   ATT   CCT   ATT   GAT   TCA   TCA   GAT   TTT   GCA   TTG   GAT   ATT   193
Thr   Arg   Pro   Val   Ile   Pro   Ile   Asp   Ser   Ser   Asp   Phe   Ala   Leu   Asp   Ile
                   50                       55                             60
```

| | | | | | | | | | | | | | | | | |
|---|---|---|---|---|---|---|---|---|---|---|---|---|---|---|---|---|
| CGC | ATG | CCT | GGA | GTC | ACA | CCT | AAA | CAG | TCT | GAT | ACA | TAC | TTC | TGC | ATG | 241 |
| Arg | Met | Pro | Gly | Val | Thr | Pro | Lys | Gln | Ser | Asp | Thr | Tyr | Phe | Cys | Met | |
| | | | 65 | | | | 70 | | | | | 75 | | | | |
| TCG | ATG | CGT | TTG | CCA | ATG | GAT | GAG | GAA | ACC | TTC | GTG | ATT | GAC | TTC | AAA | 289 |
| Ser | Met | Arg | Leu | Pro | Met | Asp | Glu | Glu | Thr | Phe | Val | Ile | Asp | Phe | Lys | |
| | | 80 | | | | | 85 | | | | | | 90 | | | |
| CCT | CGT | GCC | AGC | ATG | GAT | ACT | GTC | CAT | CAT | ATG | TTA | CTT | TTT | GGT | TGC | 337 |
| Pro | Arg | Ala | Ser | Met | Asp | Thr | Val | His | His | Met | Leu | Leu | Phe | Gly | Cys | |
| | | 95 | | | | | 100 | | | | | 105 | | | | |
| AAT | ATG | CCC | TCA | TCC | ACT | GGA | AGT | TAC | TGG | TTT | TGT | GAT | GAA | GGC | GTC | 385 |
| Asn | Met | Pro | Ser | Ser | Thr | Gly | Ser | Tyr | Trp | Phe | Cys | Asp | Glu | Gly | Val | |
| 110 | | | | | 115 | | | | | 120 | | | | | 125 | |
| TGT | ACA | GAC | AAA | GCC | AAT | ATT | CTC | TAT | GCC | TGG | GCA | AGA | AAT | GCT | CCC | 433 |
| Cys | Thr | Asp | Lys | Ala | Asn | Ile | Leu | Tyr | Ala | Trp | Ala | Arg | Asn | Ala | Pro | |
| | | | | 130 | | | | | 135 | | | | | 140 | | |
| CCC | ACC | AGA | CTC | CCC | AAA | GGT | GTT | GGA | TTC | AGA | GTT | GGA | GGA | GAG | ACT | 481 |
| Pro | Thr | Arg | Leu | Pro | Lys | Gly | Val | Gly | Phe | Arg | Val | Gly | Gly | Glu | Thr | |
| | | | 145 | | | | | 150 | | | | | 155 | | | |
| GGA | AGT | AAA | TAC | TTC | GTA | CTA | CAA | GTA | CAC | TAT | GGG | GAT | ATT | AGT | GCT | 529 |
| Gly | Ser | Lys | Tyr | Phe | Val | Leu | Gln | Val | His | Tyr | Gly | Asp | Ile | Ser | Ala | |
| | | 160 | | | | | 165 | | | | | 170 | | | | |
| TTT | AGA | GAT | AAT | CAC | AAG | GAC | TGT | TCT | GGT | GTG | TCC | TTA | CAC | CTC | ACA | 577 |
| Phe | Arg | Asp | Asn | His | Lys | Asp | Cys | Ser | Gly | Val | Ser | Leu | His | Leu | Thr | |
| 175 | | | | | 180 | | | | | 185 | | | | | | |
| CGC | CTG | CCA | CAG | CCT | TTA | ATT | GCT | GGC | ATG | TAC | CTT | ATG | ATG | GCT | CTT | 625 |
| Arg | Leu | Pro | Gln | Pro | Leu | Ile | Ala | Gly | Met | Tyr | Leu | Met | Met | Ala | Leu | |
| 190 | | | | | 195 | | | | | 200 | | | | | 205 | |
| GAC | ACT | GTT | ATA | CCA | GCA | GGA | GAG | AAA | GTG | GTG | AAT | TCT | GAC | CTT | TCA | 673 |
| Asp | Thr | Val | Ile | Pro | Ala | Gly | Glu | Lys | Val | Val | Asn | Ser | Asp | Leu | Ser | |
| | | | | 210 | | | | | 215 | | | | | 220 | | |
| TGC | CAT | TAT | AAA | AAG | TAC | CCA | ATG | CAT | GTC | TTT | GCC | TAT | AGA | GTT | CAC | 721 |
| Cys | His | Tyr | Lys | Lys | Tyr | Pro | Met | His | Val | Phe | Ala | Tyr | Arg | Val | His | |
| | | | 225 | | | | | 230 | | | | | 235 | | | |
| ACT | CAC | CAT | TTA | GGT | AAG | GTA | GTA | AGT | GGC | TAC | AGA | GTA | AGA | AAT | GGA | 769 |
| Thr | His | His | Leu | Gly | Lys | Val | Val | Ser | Gly | Tyr | Arg | Val | Arg | Asn | Gly | |
| | | 240 | | | | | 245 | | | | | 250 | | | | |
| CAG | TGG | ACA | CTG | ATT | GGA | CGT | CAG | AGC | CCC | CAG | CTG | CCA | CAG | GCT | TTC | 817 |
| Gln | Trp | Thr | Leu | Ile | Gly | Arg | Gln | Ser | Pro | Gln | Leu | Pro | Gln | Ala | Phe | |
| | 255 | | | | | 260 | | | | | 265 | | | | | |
| TAC | CCT | GTG | GAA | CAC | CCA | GTA | GAT | GTC | AGT | TTT | GGT | GAC | ATA | CTG | GCA | 865 |
| Tyr | Pro | Val | Glu | His | Pro | Val | Asp | Val | Ser | Phe | Gly | Asp | Ile | Leu | Ala | |
| 270 | | | | | 275 | | | | | 280 | | | | | 285 | |
| GCA | AGA | TGT | GTG | TTC | ACT | GGT | GAA | GGA | AGG | ACA | GAA | GCC | ACG | CAC | ATT | 913 |
| Ala | Arg | Cys | Val | Phe | Thr | Gly | Glu | Gly | Arg | Thr | Glu | Ala | Thr | His | Ile | |
| | | | | 290 | | | | | 295 | | | | | 300 | | |
| GGT | GGC | ACA | TCT | AGT | GAT | GAA | ATG | TGC | AAC | TTA | TAC | ATT | ATG | TAT | TAC | 961 |
| Gly | Gly | Thr | Ser | Ser | Asp | Glu | Met | Cys | Asn | Leu | Tyr | Ile | Met | Tyr | Tyr | |
| | | | 305 | | | | | 310 | | | | | 315 | | | |
| ATG | GAA | GCC | AAG | CAC | GCA | GTT | TCT | TTC | ATG | ACC | TGT | ACC | CAG | AAT | GTA | 1009 |
| Met | Glu | Ala | Lys | His | Ala | Val | Ser | Phe | Met | Thr | Cys | Thr | Gln | Asn | Val | |
| | | 320 | | | | | 325 | | | | | 330 | | | | |
| GCT | CCA | GAA | ATG | TTC | AGA | ACC | ATC | CCC | CCA | GAG | GCC | AAT | ATT | CCA | ATT | 1057 |
| Ala | Pro | Glu | Met | Phe | Arg | Thr | Ile | Pro | Pro | Glu | Ala | Asn | Ile | Pro | Ile | |
| | 335 | | | | | 340 | | | | | 345 | | | | | |
| CCT | GTG | AAG | TCC | GAC | ATG | GTT | ATG | ATG | CAT | GGA | CAT | CAC | AAA | GAA | ACA | 1105 |
| Pro | Val | Lys | Ser | Asp | Met | Val | Met | Met | His | Gly | His | His | Lys | Glu | Thr | |
| 350 | | | | | 355 | | | | | 360 | | | | | 365 | |
| GAG | AAC | AAA | GAT | AAG | ACT | TCA | CTA | CAA | CAG | CCA | AAA | CAA | GAA | GAA | GAA | 1153 |
| Glu | Asn | Lys | Asp | Lys | Thr | Ser | Leu | Gln | Gln | Pro | Lys | Gln | Glu | Glu | Glu | |
| | | | | 370 | | | | | 375 | | | | | 380 | | |

```
GTG  TTA  GAA  CAG  GGT  GAT  TTC  TAT  TCA  CTG  CTT  TCC  AAG  CTG  CTA  GGA       1201
Val  Leu  Glu  Gln  Gly  Asp  Phe  Tyr  Ser  Leu  Leu  Ser  Lys  Leu  Leu  Gly
               385                           390                      395

GAA  AGG  GAA  GAT  GTT  GTT  CAT  GTG  CAT  AAA  TAT  AAC  CCT  ACA  GAA  AAG       1249
Glu  Arg  Glu  Asp  Val  Val  His  Val  His  Lys  Tyr  Asn  Pro  Thr  Glu  Lys
               400                           405                      410

GCA  GAA  TCA  GAG  TCA  GAC  CTG  GTA  GCT  GAG  ATT  GCA  AAT  GTA  GTC  CAA       1297
Ala  Glu  Ser  Glu  Ser  Asp  Leu  Val  Ala  Glu  Ile  Ala  Asn  Val  Val  Gln
               415                           420                      425

AAG  AAG  GAT  CTC  GGT  CGA  TCT  GAT  GCC  AGA  GAG  AGT  GCA  GAG  CAT  GAG       1345
Lys  Lys  Asp  Leu  Gly  Arg  Ser  Asp  Ala  Arg  Glu  Ser  Ala  Glu  His  Glu
430                      435                      440                      445

GAC  AGG  GGC  AAT  GCT  ATT  CTT  GTC  AGA  GAC  AGA  ATT  CAC  AAA  TTC  CAC       1393
Asp  Arg  Gly  Asn  Ala  Ile  Leu  Val  Arg  Asp  Arg  Ile  His  Lys  Phe  His
                         450                      455                      460

AGA  CTA  GAA  TCT  ACT  TTG  AGG  CCA  ACA  GAG  AGC  AGA  GTT  ATC  TCA  GTA       1441
Arg  Leu  Glu  Ser  Thr  Leu  Arg  Pro  Thr  Glu  Ser  Arg  Val  Ile  Ser  Val
               465                           470                      475

CCG  CAG  CCC  CTA  CCT  GGT  GAA  GGC  ACC  TGG  GAA  CCA  GAA  CAC  ACA  GGA       1489
Pro  Gln  Pro  Leu  Pro  Gly  Glu  Gly  Thr  Trp  Glu  Pro  Glu  His  Thr  Gly
               480                           485                      490

GAT  TTC  CAT  GTA  GAA  GAG  GCA  CTG  GAT  TGG  CCT  GGA  GTA  TAC  TTG  TTA       1537
Asp  Phe  His  Val  Glu  Glu  Ala  Leu  Asp  Trp  Pro  Gly  Val  Tyr  Leu  Leu
     495                           500                      505

CCA  GGC  CAG  GTT  TCT  GGG  GTA  GCT  CTG  GAC  CTT  CAG  AAT  AAC  CTG  GTG       1585
Pro  Gly  Gln  Val  Ser  Gly  Val  Ala  Leu  Asp  Leu  Gln  Asn  Asn  Leu  Val
510                           515                      520                 525

ATT  TTC  CAC  AGA  GGT  GAC  CAT  GTC  TGG  GAT  GGA  AAC  TCT  TTT  GAC  AGC       1633
Ile  Phe  His  Arg  Gly  Asp  His  Val  Trp  Asp  Gly  Asn  Ser  Phe  Asp  Ser
                    530                      535                      540

AAG  TTT  GTG  TAC  CAG  CAA  AGA  GGA  CTC  GGG  CCA  ATT  GAA  GAA  GAT  ACT       1681
Lys  Phe  Val  Tyr  Gln  Gln  Arg  Gly  Leu  Gly  Pro  Ile  Glu  Glu  Asp  Thr
               545                           550                      555

ATT  CTT  GTC  ATA  GAT  CCA  AAT  AAT  GCT  GCA  GTC  CTC  CAG  TCC  AGT  GGA       1729
Ile  Leu  Val  Ile  Asp  Pro  Asn  Asn  Ala  Ala  Val  Leu  Gln  Ser  Ser  Gly
               560                           565                      570

AAA  AAT  CTG  TTT  TAC  TTG  CCA  CAT  GGC  TTG  AGC  ATA  GAC  AAA  GAT  GGA       1777
Lys  Asn  Leu  Phe  Tyr  Leu  Pro  His  Gly  Leu  Ser  Ile  Asp  Lys  Asp  Gly
575                           580                      585

AAT  TAT  TGG  GTC  ACA  GAC  GTG  GCT  CTC  CAT  CAG  GTG  TTC  AAA  CTG  GAT       1825
Asn  Tyr  Trp  Val  Thr  Asp  Val  Ala  Leu  His  Gln  Val  Phe  Lys  Leu  Asp
590                           595                      600                 605

CCA  AAC  AGT  AAA  GAA  GGC  CCT  CTG  TTG  ATC  CTG  GGA  AGA  AGC  ATG  CAA       1873
Pro  Asn  Ser  Lys  Glu  Gly  Pro  Leu  Leu  Ile  Leu  Gly  Arg  Ser  Met  Gln
                         610                      615                      620

CCA  GGC  AGT  GAC  CAG  AAT  CAC  TTC  TGT  CAA  CCC  ACC  GAT  GTG  GCT  GTA       1921
Pro  Gly  Ser  Asp  Gln  Asn  His  Phe  Cys  Gln  Pro  Thr  Asp  Val  Ala  Val
               625                           630                      635

GAT  CCA  AAC  ACT  GGG  ACC  ATC  TTT  GTA  TCA  GAT  GGT  TAC  TGC  AAC  AGT       1969
Asp  Pro  Asn  Thr  Gly  Thr  Ile  Phe  Val  Ser  Asp  Gly  Tyr  Cys  Asn  Ser
               640                           645                      650

CGG  ATC  GTG  CAG  TTT  TCA  CCA  ACT  GGA  AGG  TTC  ATC  ACA  CAG  TGG  GGA       2017
Arg  Ile  Val  Gln  Phe  Ser  Pro  Thr  Gly  Arg  Phe  Ile  Thr  Gln  Trp  Gly
655                           660                      665

GAA  GAG  TCT  TCT  GAG  AGC  AAT  CCT  AAA  CCA  GGC  CAG  TTC  AGG  GTT  CCT       2065
Glu  Glu  Ser  Ser  Glu  Ser  Asn  Pro  Lys  Pro  Gly  Gln  Phe  Arg  Val  Pro
670                           675                      680                 685

CAC  AGC  TTG  GCC  CTT  GTG  CCT  CAT  TTG  GGC  CAA  TTA  TGT  GTG  GCC  GAC       2113
His  Ser  Leu  Ala  Leu  Val  Pro  His  Leu  Gly  Gln  Leu  Cys  Val  Ala  Asp
               690                           695                      700
```

| | | | | | | | | | | | | | | | | |
|---|---|---|---|---|---|---|---|---|---|---|---|---|---|---|---|---|
| CGG | GAA | AAT | GGT | CGG | ATC | CAG | TGT | TTT | AAA | ACT | GAC | ACC | AAA | GAA | TTT | 2161 |
| Arg | Glu | Asn | Gly | Arg | Ile | Gln | Cys | Phe | Lys | Thr | Asp | Thr | Lys | Glu | Phe | |
| | | | 705 | | | | | 710 | | | | | 715 | | | |
| GTG | CGA | GAG | ATT | AAG | CAT | GCA | TCA | TTT | GGA | AGA | AAT | GTA | TTT | GCA | ATT | 2209 |
| Val | Arg | Glu | Ile | Lys | His | Ala | Ser | Phe | Gly | Arg | Asn | Val | Phe | Ala | Ile | |
| | | 720 | | | | | 725 | | | | | 730 | | | | |
| TCG | TAT | ATA | CCA | GGT | TTG | CTC | TTT | GCC | GTA | AAT | GGG | AAG | CCT | TAC | TTT | 2257 |
| Ser | Tyr | Ile | Pro | Gly | Leu | Leu | Phe | Ala | Val | Asn | Gly | Lys | Pro | Tyr | Phe | |
| | 735 | | | | | 740 | | | | | 745 | | | | | |
| GGG | GAC | CAA | AAA | CCA | GTA | CAA | GGA | TTT | GTG | ATG | AAC | TTT | TCC | AGT | GGG | 2305 |
| Gly | Asp | Gln | Lys | Pro | Val | Gln | Gly | Phe | Val | Met | Asn | Phe | Ser | Ser | Gly | |
| 750 | | | | | 755 | | | | | 760 | | | | | 765 | |
| GAA | ATT | ATA | GAT | GTC | TTC | AAG | CCA | GTG | CGC | AAG | CAC | TTT | GAC | ATG | CCT | 2353 |
| Glu | Ile | Ile | Asp | Val | Phe | Lys | Pro | Val | Arg | Lys | His | Phe | Asp | Met | Pro | |
| | | | 770 | | | | | 775 | | | | | 780 | | | |
| CAT | GAC | ATT | ACT | GCA | TCT | GAA | GAC | GGG | ACT | GTG | TAT | GTT | GGA | GAT | GCT | 2401 |
| His | Asp | Ile | Thr | Ala | Ser | Glu | Asp | Gly | Thr | Val | Tyr | Val | Gly | Asp | Ala | |
| | | | 785 | | | | | 790 | | | | | 795 | | | |
| CAC | ACC | AAC | ACC | GTG | TGG | AAG | TTC | ACT | TCG | ACT | GAA | ACA | GCC | CAG | GTC | 2449 |
| His | Thr | Asn | Thr | Val | Trp | Lys | Phe | Thr | Ser | Thr | Glu | Thr | Ala | Gln | Val | |
| | | 800 | | | | | 805 | | | | | 810 | | | | |
| TGG | TTC | CCG | GGT | GTG | GAC | CTA | CAT | CAC | TCG | TCA | GTG | GCC | ATG | CTG | TGG | 2497 |
| Trp | Phe | Pro | Gly | Val | Asp | Leu | His | His | Ser | Ser | Val | Ala | Met | Leu | Trp | |
| 815 | | | | | 820 | | | | | 825 | | | | | | |
| TGG | CAG | CTC | ACA | TAC | AAA | AAG | AGG | AAG | ATT | GAC | AAC | AGA | TGT | TAT | CTC | 2545 |
| Trp | Gln | Leu | Thr | Tyr | Lys | Lys | Arg | Lys | Ile | Asp | Asn | Arg | Cys | Tyr | Leu | |
| 830 | | | | | 835 | | | | | 840 | | | | | 845 | |
| AGG | GCC | AAT | CTT | CCT | CAG | CAA | ATG | AAA | AAA | AAA | AGA | GTG | GAG | CAT | CGA | 2593 |
| Arg | Ala | Asn | Leu | Pro | Gln | Gln | Met | Lys | Lys | Lys | Arg | Val | Glu | His | Arg | |
| | | | | 850 | | | | | 855 | | | | | 860 | | |
| TCA | GTT | AAA | AAG | GCT | GGC | ATT | GAG | GTC | CAG | GAA | ATC | AAA | GAA | TCC | GAG | 2641 |
| Ser | Val | Lys | Lys | Ala | Gly | Ile | Glu | Val | Gln | Glu | Ile | Lys | Glu | Ser | Glu | |
| | | | 865 | | | | | 870 | | | | | 875 | | | |
| GCA | GTT | GTT | GAA | ACC | AAA | ATG | GAG | AAC | AAA | CCC | GCC | TCC | TCA | GAA | TTG | 2689 |
| Ala | Val | Val | Glu | Thr | Lys | Met | Glu | Asn | Lys | Pro | Ala | Ser | Ser | Glu | Leu | |
| | | 880 | | | | | 885 | | | | | 890 | | | | |
| CAG | AAG | ATG | CAA | GAG | AAA | CAG | AAA | CTG | ATC | AAA | GAG | CCA | GGC | TCG | GGA | 2737 |
| Gln | Lys | Met | Gln | Glu | Lys | Gln | Lys | Leu | Ile | Lys | Glu | Pro | Gly | Ser | Gly | |
| | 895 | | | | | 900 | | | | | 905 | | | | | |
| GTG | CCC | GTT | GTT | CTC | ATT | ACA | ACC | CTT | CTG | GTT | ATT | CCG | GTG | GTT | GTC | 2785 |
| Val | Pro | Val | Val | Leu | Ile | Thr | Thr | Leu | Leu | Val | Ile | Pro | Val | Val | Val | |
| 910 | | | | | 915 | | | | | 920 | | | | | 925 | |
| CTG | CTG | GCC | ATT | GCC | ATA | TTT | ATT | CGG | TGG | AAA | AAA | TCA | AGG | GCC | TTT | 2833 |
| Leu | Leu | Ala | Ile | Ala | Ile | Phe | Ile | Arg | Trp | Lys | Lys | Ser | Arg | Ala | Phe | |
| | | | | 930 | | | | | 935 | | | | | 940 | | |
| GGA | GAG | TCT | GAA | CAC | AAA | GTC | GAG | GCA | AGT | TCA | GGA | AGA | GTA | CTG | GGA | 2881 |
| Gly | Glu | Ser | Glu | His | Lys | Val | Glu | Ala | Ser | Ser | Gly | Arg | Val | Leu | Gly | |
| | | | | 945 | | | | | 950 | | | | | 955 | | |
| AGA | CTT | AGA | GGA | AAA | GGA | AGT | GGA | GGC | TTA | AAC | CTC | GGA | AAT | TTC | TTT | 2929 |
| Arg | Leu | Arg | Gly | Lys | Gly | Ser | Gly | Gly | Leu | Asn | Leu | Gly | Asn | Phe | Phe | |
| | | 960 | | | | | 965 | | | | | 970 | | | | |
| GCG | AGC | CGT | AAA | GGC | TAC | AGT | CGG | AAA | GGG | TTT | GAC | CGG | CTC | AGC | ACC | 2977 |
| Ala | Ser | Arg | Lys | Gly | Tyr | Ser | Arg | Lys | Gly | Phe | Asp | Arg | Leu | Ser | Thr | |
| | 975 | | | | | 980 | | | | | 985 | | | | | |
| GAG | GGG | AGT | GAC | CAG | GAG | AAA | GAT | GAG | GAT | GAC | GGA | AGT | GAA | TCA | GAA | 3025 |
| Glu | Gly | Ser | Asp | Gln | Glu | Lys | Asp | Glu | Asp | Asp | Gly | Ser | Glu | Ser | Glu | |
| 990 | | | | | 995 | | | | | 1000 | | | | | 1005 | |
| GAA | GAA | TAT | TCA | GCA | CCT | CTG | CCC | GCA | CCT | GTA | CCT | TCC | TCC | TCC | | 3070 |
| Glu | Glu | Tyr | Ser | Ala | Pro | Leu | Pro | Ala | Pro | Val | Pro | Ser | Ser | Ser | | |
| | | | | 1010 | | | | | 1015 | | | | | 1020 | | |

```
TGAAAACTGG GCTTTGATTT AGTTGATGAG ATTTACCAAG AATGCCAGGT TCCTTTCCCT   3130
TTAGCACGAT TAGAGTTTTG TGTATTTAAT TGTAAACTGT ACTAGTCTGT GTGGGACTGT   3190
ACACATTTTA TTTACTTCGT TTTGGTTTAG TTGGCTTCTG TTTCTGGTTG AGGAGTTTCC   3250
TAAAAGTTCA TAACAGTGCC ATTGTCTTTA TCTGAACATA GAATAGAGAA ACAGTCCTCT   3310
TCTTCCATCA CGTTACTAAT TTAATGATGG AAGCTTTGCT CATTTACATT TTGAGACTTT   3370
TCTGTAGGTG TAAATAGCCC CATTCTCTGC TTGGACACAG TCTTTTCCCA ATAGCACTTC   3430
CATTGCCAGT GTCTTTCTTT GGTGCCTTTC CTGTTCAGCA TTCTCAGCCT GTGGCAGTAA   3490
AGAGAAACTT TGTGCTACAC GACGACGAAG CTGCTAAATC TTCTTCTATT TTTTAAAAT    3550
CACTAACATT ATATTGCAAC AAGGGAAAGA AAAAAGTCTC TATTTAAATT CTTTTTTTA    3610
AATTTTCTTC TTTAGTTGGT GTGTTTTGG GATGTCTTAT TTTTAGATGG TTACACTGTT    3670
AGAACACTAT TTTCAGAATC TGAATGTAAT TTGTGTAATA AAGTGTTTTC AGAGCATTAG   3730
CTGTCAGAGT GTATTTTGCC AATTTTTGCA TATGTCCAGG GTTTTGTATA CTTTTGTAAT   3790
AATTACATAA ACCACAGATT GAGTGAAACC TACTCAATGT CTTCAACCAA AGAAATGTG    3850
TTGTATTGTA TTAAAATCAA GAAGATATTT TGTTATGTAG CTGATACAAA TTAAAAACCA   3910
GCCTAAGAGC TTACATACAT GTGTAAAATC AGGCTCTCTG ATGATTCAAC GAGAGTGTTT   3970
GCCTGTATAT CAATCAGAAG GTAAATATCT GAATAAAAGG TGATCATAGC TGAGAGGAAA   4030
AAAAAAAAAA GAGTGGAGCA TCGATCAGTT AAAAAGGCTG GCATTGAGGT CCAGGAAATC   4090
AAAGAATCCG AGGCAGTTGT TGAAACCAAA ATGGAGAACA AACCCGCCTC CTCAGAATTG   4150
CAGAAGATGC AAGAGAAACA GAAACTGATC AAAGAGCCAG GCTCGGGAGT GCCCGTTGTT   4210
CTCATTACAA CCCTTCTGGT TATTCCGGTG GTTGTCCTGC TGGCCATTGC CATATTTATT   4270
CGGTGGAAAA AATCAAGGGC CTTTGGAGAG TCTGAACACA AAGTCGAGGC AAGTTCAGGA   4330
AGAGTACTGG GAAGACTTAG AGGAAAAGGA AGTGGAGGCT TAAACCTCGG AAATTTCTTT   4390
GCGAGCCGTA AAGGCTACAG TCGGAAAGGG TTTGACCGGC TCAGCACCGA GGGGAGTGAC   4450
CAGGAGAAAG ATGAGGATGA CGGAAGTGAA TCAGAAGAAG AATATTCAGC ACCTCTGCCC   4510
GCACCTGTAC CTTCCTCCTC CTGAAAACTG GGCTTTGATT TAGTTGATGA GATTACCAA    4570
GAATGCCAGG TTCCTTTCCC TTTAGCACGA TTAGAGTTTT GTGTATTTAA TTGTAAACTG   4630
TACTAGTCTG TGTGGGACTG TACACATTTT ATTTACTTCG TTTTGGTTTA GTTGGCTTCT   4690
GTTTCTGGTT GAGGAGTTTC CTAAAAGTTC ATAACAGTGC CATTGTCTTT ATCTGAACAT   4750
AGAATAGAGA AACAGTCCTC TTCTTCCATC ACGTTACTAA TTTAATGATG GAAGCTTTGC   4810
TCATTTACAT TTTGAGACTT TTCTGTAGGT GTAAATAGCC CCATTCTCTG CTTGGACACA   4870
GTCTTTTCCC AATAGCACTT CCATTGCCAG TGTCTTTCTT TGGTGCCTTT CCTGTTCAGC   4930
ATTCTCAGCC TGTGGCAGTA AAGAGAAACT TTGTGCTACA CGACGACGAA GCTGCTAAAT   4990
CTTCTTCTAT TTTTTAAAA TCACTAACAT TATATTGCAA CAAGGGAAAG AAAAAAGTCT    5050
CTATTTAAAT TCTTTTTTT AAATTTTCTT CTTTAGTTGG TGTGTTTTTG GATGTCTTA     5110
TTTTTAGATG GTTACACTGT TAGAACACTA TTTTCAGAAT CTGAATGTAA TTTGTGTAAT   5170
AAAGTGTTTT CAGAGCATTA AAAAAAAAAA AAAAAAAAA AAAAAAAAA AAAAAAAAA      5230
AAACAGCCCA GGTCTGGTTC CCGGGTGTGG ACCTACATCA CTCGTCAGTG GCCATGCTGT   5290
GGTGGCAGCT CACATACAAA AGAGGAAGA TTGACAACAG ATGTTATCTC AGGGCCAATC    5350
TTCCTCAGCA AATGAAAAAA AAAAGAGTGG AGCATCGATC AGTTAAAAAG GCTGGCATTG   5410
AGGTCCAGGA AATCAAAGCA GAGTCTGAAC ACAAAGTCGA GGCAAGTTCA GGAAGAGTAC   5470
```

-continued

| | | | | | |
|---|---|---|---|---|---|
| TGGGAAGACT | TAGAGGAAAA | GGAAGTGGAG | GCTTAAACCT | CGGAAATTTC | TTTGCGAGCC | 5530 |
| GTAAAGGCTA | CAGTCGGAAA | GGGTTTGACC | GGCTCAGCAC | CGAGGGGAGT | GACCAGGAGA | 5590 |
| AAGATGAGGA | TGACGGAAGT | GAATCAGAAG | AACAATATTC | AGCACCTCTG | CCCGCACCTG | 5650 |
| TACCTTCCTC | CTCCTGAAAA | CTGGGCTTTG | ATTTAGTTGA | TGAGATTTAC | CAAGAATGCC | 5710 |
| AGGTTCCTTT | CCCTTTAGCA | CGATTAGAGT | TTTGTGTATT | TAATTGTAAA | CTGTACTAGT | 5770 |
| CTGTGTGGGA | CTGTACACAT | TTTATTTACT | TCGTTTTGGT | TTAGTTGGCT | TCTGTTTCTG | 5830 |
| GTTGAGGAGT | TTCCTAAAAG | TTCATAACAG | TGCCATTGTC | TTTATCTGAA | CATAGAATAG | 5890 |
| AGAAACAGTC | CTCTTCTTCC | ATCACGTTAC | TAATTTAATG | ATGGAAGCTT | TGCTCATTTA | 5950 |
| CATTTTGAGA | CTTTTCTGTA | GGTGTAAATA | GCCCCATTCT | CTGCTTGGAC | ACAGTCTTTT | 6010 |
| CCCAATAGCA | CTTCCATTGC | CAGTGTCTTT | CTTTGGTGCC | TTTCCTGTTC | AGCATTCTCA | 6070 |
| GCCTGTGGCA | GTAAAGAGAA | ACTTTGTGCT | ACACGACGAC | GAAGCTGCTA | AATCTTCTTC | 6130 |
| TATTTTTTTA | AAATCACTAA | CATTATATTG | CAACAAGGGA | AGAAAAAAG | TCTCTATTTA | 6190 |
| AATTCTTTTT | TTTAAATTTT | CTTCTTTAGT | TGGTGTGTTT | TTGGGATGTC | TTATTTTTAG | 6250 |
| ATGGTTACAC | TGTTAGAACA | CTATTTTCAG | AATCTGAATG | TAATTTGTGT | AATAAAGTGT | 6310 |
| TTTCAGAGCA | TTAGCTGTCA | GAGTGTATTT | TGCCAATTTT | TGCATATGTC | CAGGGTTTTG | 6370 |
| TATACTTTTG | TAATAATTAC | ATAAACCACA | GATTGAGTGA | AACCTACTCA | ATGTCTTCAA | 6430 |
| CCAAAAGAAA | TGTGTTGTAT | TGTATTAAAA | TCAAGAAGAT | ATTTGTTAT | GTAGCTGATA | 6490 |
| CAAATTAAAA | ACCAGCCTAA | GAGCTTACAT | ACATGTGTAA | AATCAGGCTC | TCTGATGATT | 6550 |
| CAACGAGAGT | GTTTGCCTGT | ATATCAATCA | GAAGGTAAAT | ACTTGAATAA | AAGGTGATCA | 6610 |
| TAGCTGAGAG | GAAAAAAAA | AAAAAAA | | | | 6638 |

( 2 ) INFORMATION FOR SEQ ID NO:3:

( i ) SEQUENCE CHARACTERISTICS:
        ( A ) LENGTH: 1020 amino acids
        ( B ) TYPE: amino acid
        ( D ) TOPOLOGY: linear ( i i ) MOLECULE TYPE: protein ( x i ) SEQUENCE DESCRIPTION: SEQ ID NO:3:

```
Met Ala Gly Leu Arg Ser Leu Leu Val Leu Leu Val Phe Gln Ser
 1               5                  10                  15

Ser Cys Leu Gly Phe Arg Ser Pro Leu Ser Val Phe Lys Arg Phe Lys
             20                  25                  30

Glu Thr Thr Arg Pro Phe Ser Asn Glu Cys Leu Gly Thr Thr Arg Pro
         35                  40                  45

Val Ile Pro Ile Asp Ser Ser Asp Phe Ala Leu Asp Ile Arg Met Pro
     50                  55                  60

Gly Val Thr Pro Lys Gln Ser Asp Thr Tyr Phe Cys Met Ser Met Arg
 65                  70                  75                  80

Leu Pro Met Asp Glu Glu Thr Phe Val Ile Asp Phe Lys Pro Arg Ala
                 85                  90                  95

Ser Met Asp Thr Val His His Met Leu Leu Phe Gly Cys Asn Met Pro
                100                 105                 110

Ser Ser Thr Gly Ser Tyr Trp Phe Cys Asp Glu Gly Val Cys Thr Asp
             115                 120                 125

Lys Ala Asn Ile Leu Tyr Ala Trp Ala Arg Asn Ala Pro Pro Thr Arg
         130                 135                 140
```

-continued

```
Leu  Pro  Lys  Gly  Val  Gly  Phe  Arg  Val  Gly  Gly  Glu  Thr  Gly  Ser  Lys
145                      150                      155                      160

Tyr  Phe  Val  Leu  Gln  Val  His  Tyr  Gly  Asp  Ile  Ser  Ala  Phe  Arg  Asp
                         165                      170                      175

Asn  His  Lys  Asp  Cys  Ser  Gly  Val  Ser  Leu  His  Leu  Thr  Arg  Leu  Pro
                    180                      185                      190

Gln  Pro  Leu  Ile  Ala  Gly  Met  Tyr  Leu  Met  Met  Ala  Leu  Asp  Thr  Val
               195                      200                      205

Ile  Pro  Ala  Gly  Glu  Lys  Val  Val  Asn  Ser  Asp  Leu  Ser  Cys  His  Tyr
          210                      215                      220

Lys  Lys  Tyr  Pro  Met  His  Val  Phe  Ala  Tyr  Arg  Val  His  Thr  His  His
225                      230                      235                      240

Leu  Gly  Lys  Val  Val  Ser  Gly  Tyr  Arg  Val  Arg  Asn  Gly  Gln  Trp  Thr
                    245                      250                      255

Leu  Ile  Gly  Arg  Gln  Ser  Pro  Gln  Leu  Pro  Gln  Ala  Phe  Tyr  Pro  Val
               260                      265                      270

Glu  His  Pro  Val  Asp  Val  Ser  Phe  Gly  Asp  Ile  Leu  Ala  Ala  Arg  Cys
          275                      280                      285

Val  Phe  Thr  Gly  Glu  Gly  Arg  Thr  Glu  Ala  Thr  His  Ile  Gly  Gly  Thr
   290                      295                      300

Ser  Ser  Asp  Glu  Met  Cys  Asn  Leu  Tyr  Ile  Met  Tyr  Tyr  Met  Glu  Ala
305                      310                      315                      320

Lys  His  Ala  Val  Ser  Phe  Met  Thr  Cys  Thr  Gln  Asn  Val  Ala  Pro  Glu
                    325                      330                      335

Met  Phe  Arg  Thr  Ile  Pro  Pro  Glu  Ala  Asn  Ile  Pro  Ile  Pro  Val  Lys
               340                      345                      350

Ser  Asp  Met  Val  Met  Met  His  Gly  His  His  Lys  Glu  Thr  Glu  Asn  Lys
          355                      360                      365

Asp  Lys  Thr  Ser  Leu  Gln  Gln  Pro  Lys  Gln  Glu  Glu  Val  Leu  Glu
370                      375                      380

Gln  Gly  Asp  Phe  Tyr  Ser  Leu  Leu  Ser  Lys  Leu  Leu  Gly  Glu  Arg  Glu
385                      390                      395                      400

Asp  Val  Val  His  Val  His  Lys  Tyr  Asn  Pro  Thr  Glu  Lys  Ala  Glu  Ser
                    405                      410                      415

Glu  Ser  Asp  Leu  Val  Ala  Glu  Ile  Ala  Asn  Val  Val  Gln  Lys  Lys  Asp
               420                      425                      430

Leu  Gly  Arg  Ser  Asp  Ala  Arg  Glu  Ser  Ala  Glu  His  Glu  Asp  Arg  Gly
          435                      440                      445

Asn  Ala  Ile  Leu  Val  Arg  Asp  Arg  Ile  His  Lys  Phe  His  Arg  Leu  Glu
     450                      455                      460

Ser  Thr  Leu  Arg  Pro  Thr  Glu  Ser  Arg  Val  Ile  Ser  Val  Pro  Gln  Pro
465                      470                      475                      480

Leu  Pro  Gly  Glu  Gly  Thr  Trp  Glu  Pro  Glu  His  Thr  Gly  Asp  Phe  His
                    485                      490                      495

Val  Glu  Glu  Ala  Leu  Asp  Trp  Pro  Gly  Val  Tyr  Leu  Leu  Pro  Gly  Gln
               500                      505                      510

Val  Ser  Gly  Val  Ala  Leu  Asp  Leu  Gln  Asn  Asn  Leu  Val  Ile  Phe  His
          515                      520                      525

Arg  Gly  Asp  His  Val  Trp  Asp  Gly  Asn  Ser  Phe  Asp  Ser  Lys  Phe  Val
     530                      535                      540

Tyr  Gln  Gln  Arg  Gly  Leu  Gly  Pro  Ile  Glu  Glu  Asp  Thr  Ile  Leu  Val
545                      550                      555                      560

Ile  Asp  Pro  Asn  Asn  Ala  Ala  Val  Leu  Gln  Ser  Ser  Gly  Lys  Asn  Leu
                    565                      570                      575
```

| | | | | | | | | | | | | | | |
|---|---|---|---|---|---|---|---|---|---|---|---|---|---|---|
| Phe | Tyr | Leu | Pro<br>580 | His | Gly | Leu | Ser | Ile<br>585 | Asp | Lys | Asp | Gly<br>590 | Asn | Tyr | Trp |
| Val | Thr | Asp<br>595 | Val | Ala | Leu | His | Gln<br>600 | Val | Phe | Lys | Leu<br>605 | Asp | Pro | Asn | Ser |
| Lys | Glu<br>610 | Gly | Pro | Leu | Leu | Ile<br>615 | Leu | Gly | Arg | Ser | Met<br>620 | Gln | Pro | Gly | Ser |
| Asp<br>625 | Gln | Asn | His | Phe | Cys<br>630 | Gln | Pro | Thr | Asp | Val<br>635 | Ala | Val | Asp | Pro | Asn<br>640 |
| Thr | Gly | Thr | Ile | Phe<br>645 | Val | Ser | Asp | Gly | Tyr<br>650 | Cys | Asn | Ser | Arg | Ile<br>655 | Val |
| Gln | Phe | Ser | Pro<br>660 | Thr | Gly | Arg | Phe | Ile<br>665 | Thr | Gln | Trp | Gly<br>670 | Glu | Glu | Ser |
| Ser | Glu | Ser<br>675 | Asn | Pro | Lys | Pro | Gly<br>680 | Gln | Phe | Arg | Val<br>685 | Pro | His | Ser | Leu |
| Ala | Leu<br>690 | Val | Pro | His | Leu | Gly<br>695 | Gln | Leu | Cys | Val | Ala<br>700 | Asp | Arg | Glu | Asn |
| Gly<br>705 | Arg | Ile | Gln | Cys | Phe<br>710 | Lys | Thr | Asp | Thr | Lys<br>715 | Glu | Phe | Val | Arg | Glu<br>720 |
| Ile | Lys | His | Ala | Ser<br>725 | Phe | Gly | Arg | Asn | Val<br>730 | Phe | Ala | Ile | Ser | Tyr<br>735 | Ile |
| Pro | Gly | Leu | Leu<br>740 | Phe | Ala | Val | Asn | Gly<br>745 | Lys | Pro | Tyr | Phe | Gly<br>750 | Asp | Gln |
| Lys | Pro | Val<br>755 | Gln | Gly | Phe | Val | Met<br>760 | Asn | Phe | Ser | Ser<br>765 | Gly | Glu | Ile | Ile |
| Asp | Val<br>770 | Phe | Lys | Pro | Val | Arg<br>775 | Lys | His | Phe | Asp | Met<br>780 | Pro | His | Asp | Ile |
| Thr<br>785 | Ala | Ser | Glu | Asp | Gly<br>790 | Thr | Val | Tyr | Val | Gly<br>795 | Asp | Ala | His | Thr | Asn<br>800 |
| Thr | Val | Trp | Lys | Phe<br>805 | Thr | Ser | Thr | Glu | Thr<br>810 | Ala | Gln | Val | Trp | Phe<br>815 | Pro |
| Gly | Val | Asp | Leu<br>820 | His | His | Ser | Ser | Val<br>825 | Ala | Met | Leu | Trp<br>830 | Trp | Gln | Leu |
| | Thr | Tyr | Lys | Lys | Arg<br>835 | Lys | Ile | Asp | Asn | Arg<br>840 | Cys | Tyr | Leu | Arg<br>845 | Ala | Asn |
| Leu | Pro<br>850 | Gln | Gln | Met | Lys | Lys<br>855 | Arg | Val | Glu | His | Arg<br>860 | Ser | Val | Lys |
| Lys<br>865 | Ala | Gly | Ile | Glu | Val<br>870 | Gln | Glu | Ile | Lys | Glu<br>875 | Ser | Glu | Ala | Val | Val<br>880 |
| Glu | Thr | Lys | Met | Glu<br>885 | Asn | Lys | Pro | Ala | Ser<br>890 | Ser | Glu | Leu | Gln | Lys<br>895 | Met |
| Gln | Glu | Lys | Gln<br>900 | Lys | Leu | Ile | Lys | Glu<br>905 | Pro | Gly | Ser | Gly | Val<br>910 | Pro | Val |
| Val | Leu | Ile<br>915 | Thr | Thr | Leu | Leu | Val<br>920 | Ile | Pro | Val | Val<br>925 | Leu | Leu | Ala |
| Ile | Ala<br>930 | Ile | Phe | Ile | Arg | Trp<br>935 | Lys | Lys | Ser | Arg | Ala<br>940 | Phe | Gly | Glu | Ser |
| Glu<br>945 | His | Lys | Val | Glu | Ala<br>950 | Ser | Ser | Gly | Arg | Val<br>955 | Leu | Gly | Arg | Leu | Arg<br>960 |
| Gly | Lys | Gly | Ser | Gly<br>965 | Gly | Leu | Asn | Leu | Gly<br>970 | Asn | Phe | Phe | Ala | Ser<br>975 | Arg |
| Lys | Gly | Tyr | Ser<br>980 | Arg | Lys | Gly | Phe | Asp<br>985 | Arg | Leu | Ser | Thr | Glu<br>990 | Gly | Ser |
| Asp | Gln | Glu | Lys | Asp | Glu | Asp | Asp | Gly | Ser | Glu | Ser | Glu | Glu | Glu | Tyr |

-continued

```
                    995                      1000                      1005
Ser  Ala  Pro  Leu  Pro  Ala  Pro  Val  Pro  Ser  Ser  Ser
               1010                      1015                      1020
```

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

```
Phe  Gly  Phe  Gly
 1
```

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note= ""D-tyr""

( x i ) SEQUENCE DESCRIPTION: SEQ ID NO:5:

```
Tyr  Leu  Asn  Gly  Arg
 1                    5
```

( 2 ) INFORMATION FOR SEQ ID NO:6:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Phe  Gly  Leu  Met  Gly
 1                    5
```

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Lys  Ala  Phe  Gly
 1
```

( 2 ) INFORMATION FOR SEQ ID NO:8:

( i ) SEQUENCE CHARACTERISTICS:
        ( A ) LENGTH: 4 amino acids
        ( B ) TYPE: amino acid (C) STRANDEDNESS: single
(D) TOPOLOGY: linear (ii) MOLECULE TYPE: peptide (xi) SEQUENCE DESCRIPTION: SEQ ID NO:8:

Gly Leu Met Gly
1

(2) INFORMATION FOR SEQ ID NO:9:

(i) SEQUENCE CHARACTERISTICS:
(A) LENGTH: 4 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:9:

Asp Arg Phe Gly
1

(2) INFORMATION FOR SEQ ID NO:10:

(i) SEQUENCE CHARACTERISTICS:
(A) LENGTH: 3226 base pairs
(B) TYPE: nucleic acid
(C) STRANDEDNESS: single
(D) TOPOLOGY: linear (ii) MOLECULE TYPE: cDNA (vi) ORIGINAL SOURCE:
(A) ORGANISM: Rat (ix) FEATURE:
(A) NAME/KEY: CDS
(B) LOCATION: 2..831

(xi) SEQUENCE DESCRIPTION: SEQ ID NO:10:

```
C ATG GCC GGA CGC GCC CGC AGC GGT CTG CTA CTG CTG CTG CTG GGG                46
  Met Ala Gly Arg Ala Arg Ser Gly Leu Leu Leu Leu Leu Leu Gly
  1               5                   10                  15

CTG CTC GCC CTG CAG AGC AGC TGC CTG GCC TTC AGA AGC CCA CTT TCT            94
Leu Leu Ala Leu Gln Ser Ser Cys Leu Ala Phe Arg Ser Pro Leu Ser
                20                  25                  30

GTC TTT AAG AGG TTT AAA GAA ACT ACC AGA TCA TTT TCC AAT GAA TGC           142
Val Phe Lys Arg Phe Lys Glu Thr Thr Arg Ser Phe Ser Asn Glu Cys
            35                  40                  45

CTT GGT ACC ATT GGA CCA GTC ACC CCT CTT GAT GCA TCA GAT TTT GCG           190
Leu Gly Thr Ile Gly Pro Val Thr Pro Leu Asp Ala Ser Asp Phe Ala
        50                  55                  60

CTG GAT ATT CGC ATG CCT GGG GTT ACA CCT AAA GAG TCT GAC ACA TAC           238
Leu Asp Ile Arg Met Pro Gly Val Thr Pro Lys Glu Ser Asp Thr Tyr
    65                  70                  75

TTC TGC ATG TCC ATG CGT CTG CCT GTG GAT GAG GAA GCC TTC GTG ATT           286
Phe Cys Met Ser Met Arg Leu Pro Val Asp Glu Glu Ala Phe Val Ile
80                  85                  90                  95

GAC TTC AAG CCT CGT GCC AGC ATG GAT ACT GTC CAC CAT ATG CTG CTG           334
Asp Phe Lys Pro Arg Ala Ser Met Asp Thr Val His His Met Leu Leu
                100                 105                 110

TTT GGA TGC AAT ATG CCC TCG TCC ACT GGA AGT TAC TGG TTT TGT GAT           382
Phe Gly Cys Asn Met Pro Ser Ser Thr Gly Ser Tyr Trp Phe Cys Asp
            115                 120                 125

GAA GGA ACC TGT ACA GAT AAA GCC AAT ATT CTA TAT GCC TGG GCA AGG           430
Glu Gly Thr Cys Thr Asp Lys Ala Asn Ile Leu Tyr Ala Trp Ala Arg
```

```
                    130                           135                              140
AAT  GCT  CCC  CCC  ACC  CGG  CTC  CCG  AAA  GGT  GTT  GGA  TTC  AGA  GTT  GGA              478
Asn  Ala  Pro  Pro  Thr  Arg  Leu  Pro  Lys  Gly  Val  Gly  Phe  Arg  Val  Gly
     145                      150                      155

GGA  GAA  ACT  GGA  AGC  AAA  TAC  TTC  GTC  CTT  CAA  GTT  CAC  TAT  GGC  GAT              526
Gly  Glu  Thr  Gly  Ser  Lys  Tyr  Phe  Val  Leu  Gln  Val  His  Tyr  Gly  Asp
160                      165                      170                           175

ATC  AGT  GCT  TTT  CGA  GAT  AAT  CAC  AAA  GAC  TGC  TCT  GGC  GTG  TCC  GTA             574
 Ile  Ser  Ala  Phe  Arg  Asp  Asn  His  Lys  Asp  Cys  Ser  Gly  Val  Ser  Val
                     180                      185                           190

CAT  CTC  ACA  CGT  GTG  CCC  CAG  CCT  TTA  ATT  GCG  GGC  ATG  TAC  CTT  ATG              622
His  Leu  Thr  Arg  Val  Pro  Gln  Pro  Leu  Ile  Ala  Gly  Met  Tyr  Leu  Met
               195                      200                      205

ATG  TCT  GTT  GAC  ACT  GTC  ATA  CCA  CCA  GGA  GAG  AAA  GTA  GTG  AAT  GCT              670
Met  Ser  Val  Asp  Thr  Val  Ile  Pro  Pro  Gly  Glu  Lys  Val  Val  Asn  Ala
          210                      215                      220

GAC  ATT  TCG  TGC  CAA  TAC  AAA  ATG  TAT  CCA  ATG  CAT  GTG  TTT  GCC  TAC              718
Asp  Ile  Ser  Cys  Gln  Tyr  Lys  Met  Tyr  Pro  Met  His  Val  Phe  Ala  Tyr
     225                      230                      235

AGA  GTC  CAC  ACT  CAC  CAT  TTA  GGT  AAG  GTG  GTG  AGC  GGA  TAC  AGA  GTA              766
Arg  Val  His  Thr  His  His  Leu  Gly  Lys  Val  Val  Ser  Gly  Tyr  Arg  Val
240                      245                      250                           255

AGA  AAC  GGA  CAG  TGG  ACA  CTG  ATT  GGA  CGC  CAG  AAC  CCC  CAG  CTG  CCA              814
Arg  Asn  Gly  Gln  Trp  Thr  Leu  Ile  Gly  Arg  Gln  Asn  Pro  Gln  Leu  Pro
                260                      265                      270

CAG  GCT  TTC  TAC  CCT  GT  GGAACACCCC  GTTGATGTTA  CTTTTGGTGA                             861
Gln  Ala  Phe  Tyr  Pro
               275

TATACTGGCA  GCCAGATGTG  TGTTCACTGG  TGAAGGGAGG  ACAGAGGCCA  CCCACATCGG                      921

CGGCACTTCT  AGTGACGAAA  TGTGTAACCT  GTACATCATG  TATTACATGG  AAGCCAAATA                      981

TGCACTTTCC  TTCATGACCT  GTACAAAGAA  CGTGGCTCCA  GATATGTTCA  GAACTATCCC                     1041

AGCAGAGGCC  AATATCCCAA  TTCCTGTCAA  ACCGGACATG  GTTATGATGC  ACGGGCATCA                     1101

CAAAGAAGCA  GAAAACAAAG  AAAAGAGTGC  TTTAATGCAG  CAGCCAAAAC  AGGGAGAGGA                     1161

AGAAGTATTA  GAGCAGGAAT  TCCATGTGG   AAGAAGAACT  GGACTGGCCT  GGAGTGTACT                     1221

TGTTACCAGG  CCAGGTTTCT  GGGGTGGCCC  TGGATTCTAA  GAATAACCTG  TGATTTTCCA                     1281

CAGAGGTGAC  CATGTTTGGG  ATGGAAACTC  TTTTGACAGC  AAGTTTGTTT  ACCAGCAAAG                     1341

AGGTCTTGGG  CCAATTGAAG  AAGACACCAT  CCTGGTCATT  GACCCAAATA  ATGCTGAAAT                     1401

CCTCCAGTCC  AGTGGCAAGA  ACCTGTTTTA  TTACCACAC   GGCTTGAGCA  TAGATACAGA                     1461

TGGAAATTAT  TGGGTCACAG  ATGTGGCTCT  CCACCAGGTG  TTCAAATTGG  ACCCGCATAG                     1521

CAAAGAAGGC  CCTCTCTTAA  TTCTGGGAAG  GAGCATGCAA  CCTGGGAGTG  ACCAAAATCA                     1581

TTTCTGCCAG  CCCACCGATG  TGGCTGTGGA  GCCCAGTACT  GGAGCTGTCT  TCGTGTCAGA                     1641

CGGTTACTGT  AACAGTCGGA  TTGTGCAGTT  TTCACCAAGC  GGAAAGTTCG  TCACCCAGTG                     1701

GGGAGAAGAG  TCCTCTGGAA  GCAGTCCTAG  GCCAGGCCAG  TTCAGTGTTC  CTCAGAGTTT                     1761

GGCCCTTGTG  CCTCATTTGG  ACCAGTTGTG  TGTGGCAGAC  AGGGAAAATG  GCCGAATCCA                     1821

ATGCTTCAAA  ACTGACACCA  AAGAATTTGT  GAGAGAGATT  AAGCACGCAT  CATTTGGAAG                     1881

GAATGTCTTT  GCCATTTCAT  ATATACCAGG  TTTCCTCTTT  GCCGTAAACG  GAAGCCTTA                      1941

CTTTGGAGAC  CAAGAGCCCG  TGCAAGGATT  TGTGATGAAC  TTTTCCAGTG  GGAAATTAT                      2001

AGACGTCTTC  AAGCCAGTAC  GCAAGCACTT  CGACATGCCT  CATGATATTG  TGGCTTCTGA                     2061

AGATGGGACT  GTGTACATTG  GAGACGCACA  CACAAACACC  GTGTGGAAGT  TCACCCTGAC                     2121
```

| | | | | | |
|---|---|---|---|---|---|
| TGAAAAAATG | GAGCATCGGT | CAGTTAAAAA | GGCTGGCATT | GAAGTCCAGG | AAATCAAAGA | 2181
| AGCCGAGGCA | GTTGTTGAAC | CCAAAGTGGA | GAACAAACCC | ACCTCCTCAG | AATTGCAGAA | 2241
| GATGCAAGAG | AAACAGAAAC | TGAGCACAGA | GCCCGGCTCG | GGAGTGTCCG | TGGTTCTCAT | 2301
| TACAACCCTT | CTGGTTATTC | CTGTGCTGGT | CCTGCTGGCC | ATTGTCATGT | TTATTCGGTG | 2361
| GAAAAAATCA | AGGGCCTTTG | GAGGAAAGGG | AAGCGGCGGC | TTAAATCTGG | GAAATTTCTT | 2421
| TGCAAGTCGA | AAAGGCTACA | GCAGAAAAGG | GTTTGACCGA | GTGAGCACAG | AGGGGAGTGA | 2481
| CCAAGAGAAA | GATGAGGACG | ACGGAAGTGA | GTCTGAAGAG | GAGTACTCGG | CCCCGCTGCC | 2541
| CAAGCCTGCA | CCTTCCTCCT | GAGCTCCAGC | CTTCGCCCGG | GTAGCTGGAC | TGAGGTTTAC | 2601
| CAGGATGCCC | AGACTCCTTC | CCCTTTAGCG | CGTGTAAAGT | TCTGTGCATT | TGATTGTAAA | 2661
| CTGTACTCGT | CAGTGTGGGA | CTGTACACAC | CTTATTTACT | TCATTTGGCT | CCGTTGGCTT | 2721
| CTGTTTTCTA | GGTGAGGAGT | TCCCCACCAG | TTCACTCCAG | TGCCATTGTC | TTTATATGAA | 2781
| CTTAGCGTAG | AGAAGCCGCC | CTCCTCTTCC | AAGGTAGCGC | TCCAACCCCC | GAGGGAAGTT | 2841
| TAGCTCATTC | ACATTTGGAG | ACGTTTTAGT | TGGTGGATGT | AAATAGCCCT | ATTCTCTGCT | 2901
| TGAACACAGT | ATTCTCCCAG | TCCACACCCA | TCGCCAGTGT | CTTTCTTTGG | TGCCTTTCCT | 2961
| GTTCAGCATT | CTCAGCCTGT | GGCAGTGAAG | AGAACCAACC | TGCCACACGA | CGAAAAGCTG | 3021
| CTAAATCTCC | TTCTATTTTT | TTAAAATCAC | TAACATTATA | TTGCAATGAG | AGAAATTTTA | 3081
| AAAAGTCTCT | ATTTAAATTC | TTTTTTTAAA | TTTCTCCTCA | GTTGGTGTGT | TTCCGGGATG | 3141
| TCTTATTTTT | AGATGGTTAC | ACTGTTAGAA | CACTATTTTT | CAGAATCTGA | ATGTAATTTG | 3201
| TGTAATAAAG | TGTTTTCAGA | GCATT | | | | 3226

(2) INFORMATION FOR SEQ ID NO:11:

(i) SEQUENCE CHARACTERISTICS:
        (A) LENGTH: 276 amino acids
        (B) TYPE: amino acid
        (D) TOPOLOGY: linear (ii) MOLECULE TYPE: protein (xi) SEQUENCE DESCRIPTION: SEQ ID NO:11:

```
Met Ala Gly Arg Ala Arg Ser Gly Leu Leu Leu Leu Leu Gly Leu
  1               5                  10                  15

Leu Ala Leu Gln Ser Ser Cys Leu Ala Phe Arg Ser Pro Leu Ser Val
             20                  25                  30

Phe Lys Arg Phe Lys Glu Thr Thr Arg Ser Phe Ser Asn Glu Cys Leu
         35                  40                  45

Gly Thr Ile Gly Pro Val Thr Pro Leu Asp Ala Ser Asp Phe Ala Leu
     50                  55                  60

Asp Ile Arg Met Pro Gly Val Thr Pro Lys Glu Ser Asp Thr Tyr Phe
 65                  70                  75                  80

Cys Met Ser Met Arg Leu Pro Val Asp Glu Glu Ala Phe Val Ile Asp
                 85                  90                  95

Phe Lys Pro Arg Ala Ser Met Asp Thr Val His His Met Leu Leu Phe
            100                 105                 110

Gly Cys Asn Met Pro Ser Ser Thr Gly Ser Tyr Trp Phe Cys Asp Glu
        115                 120                 125

Gly Thr Cys Thr Asp Lys Ala Asn Ile Leu Tyr Ala Trp Ala Arg Asn
    130                 135                 140

Ala Pro Pro Thr Arg Leu Pro Lys Gly Val Gly Phe Arg Val Gly Gly
145                 150                 155                 160
```

| Glu | Thr | Gly | Ser | Lys | Tyr | Phe | Val | Leu | Gln | Val | His | Tyr | Gly | Asp | Ile |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Ser | Ala | Phe | Arg | Asp | Asn | His | Lys | Asp | Cys | Ser | Gly | Val | Ser | Val | His |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Leu | Thr | Arg | Val | Pro | Gln | Pro | Leu | Ile | Ala | Gly | Met | Tyr | Leu | Met | Met |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Ser | Val | Asp | Thr | Val | Ile | Pro | Pro | Gly | Glu | Lys | Val | Val | Asn | Ala | Asp |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Ile | Ser | Cys | Gln | Tyr | Lys | Met | Tyr | Pro | Met | His | Val | Phe | Ala | Tyr | Arg |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Val | His | Thr | His | His | Leu | Gly | Lys | Val | Val | Ser | Gly | Tyr | Arg | Val | Arg |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Asn | Gly | Gln | Trp | Thr | Leu | Ile | Gly | Arg | Gln | Asn | Pro | Gln | Leu | Pro | Gln |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Ala | Phe | Tyr | Pro |
|-----|-----|-----|-----|
|     |     |     | 275 |

( 2 ) INFORMATION FOR SEQ ID NO:12:

( i ) SEQUENCE CHARACTERISTICS:
        ( A ) LENGTH: 315 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Rat ( x i ) SEQUENCE DESCRIPTION: SEQ ID NO:12:

| GTGATTTCTA | TTCACTGCTT | TCCAAGCTGC | TAGGAGAAAG | GGAAGATGTT | CATGTGCACA | 60 |
|---|---|---|---|---|---|---|
| AGTATAATCC | TACAGAAAAG | ACAGAATCTG | GGTCAGACCT | GGTAGCTGAG | ATTGCAAACG | 120 |
| TGGTCCAGAA | AAAGGACCTT | GGTCGGTCTG | ACGCCAGAGA | AGGTGCAGAG | CATGAGGAAT | 180 |
| GGGGTAATGC | TATCCTAGTC | AGAGACAGGA | TCCACAGATT | CCACCAGCTA | GAGTCAACTC | 240 |
| TGAGGCCAGC | TGAGAGCAGA | GCTTTCTCGT | TCCAGCAGCC | TGGCGAAGGC | CCTTGGGAAC | 300 |
| CAGAACCCTC | AGGAG |  |  |  |  | 315 |

( 2 ) INFORMATION FOR SEQ ID NO:13:

( i ) SEQUENCE CHARACTERISTICS:
        ( A ) LENGTH: 54 base pairs
        ( B ) TYPE: nucleic acid
        ( C ) STRANDEDNESS: single
        ( D ) TOPOLOGY: linear ( i i ) MOLECULE TYPE: cDNA ( v i ) ORIGINAL SOURCE:
        ( A ) ORGANISM: Rat ( x i ) SEQUENCE DESCRIPTION: SEQ ID NO:13:

| ATCATGACCG | CAAGCTCGAG | TCAAGTTCTG | GAAGAGTCCT | GGGAAGATTC | CGAC | 54 |
|---|---|---|---|---|---|---|

( 2 ) INFORMATION FOR SEQ ID NO:14:

( i ) SEQUENCE CHARACTERISTICS:
        ( A ) LENGTH: 989 amino acids
        ( B ) TYPE: amino acid
        ( C ) STRANDEDNESS: single
        ( D ) TOPOLOGY: linear ( i i ) MOLECULE TYPE: protein (vi) ORIGINAL SOURCE:
     (A) ORGANISM: Bovine (xi) SEQUENCE DESCRIPTION: SEQ ID NO:14:

```
Met Ala Gly Xaa Phe Arg Ser Xaa Xaa Leu Leu Val Leu Leu Xaa Leu
 1               5                  10                  15

Val Xaa Phe Pro Ser Gly Cys Val Gly Phe Arg Ser Pro Leu Ser Val
             20                  25                  30

Phe Lys Arg Phe Lys Glu Thr Thr Arg Ser Phe Ser Asn Glu Cys Leu
         35                  40                  45

Gly Thr Thr Arg Pro Val Ile Pro Ile Asp Ser Ser Asp Phe Ala Leu
     50                  55                  60

Asp Ile Arg Met Pro Gly Val Thr Pro Lys Gln Ser Asp Thr Tyr Phe
 65                  70                  75                  80

Cys Met Ser Val Arg Leu Pro Met Asp Glu Ala Phe Val Ile Asp
                 85                  90                  95

Phe Lys Pro Arg Ala Ser Met Asp Thr Val His His Met Leu Leu Phe
             100                 105                 110

Gly Cys Asn Met Pro Ala Ser Thr Gly Asn Tyr Trp Phe Cys Asp Glu
         115                 120                 125

Gly Thr Cys Thr Asp Lys Ala Asn Ile Leu Tyr Ala Trp Ala Arg Asn
     130                 135                 140

Ala Pro Pro Thr Arg Leu Pro Lys Gly Val Gly Phe Arg Val Gly Gly
145                 150                 155                 160

Glu Thr Gly Ser Lys Tyr Phe Val Leu Gln Val His Tyr Gly Asp Ile
                 165                 170                 175

Ser Ala Phe Arg Asp Asn His Lys Asp Cys Ser Gly Val Ser Leu His
             180                 185                 190

Leu Thr Arg Leu Pro Gln Pro Leu Ile Ala Gly Met Tyr Leu Met Met
         195                 200                 205

Ser Val Asp Thr Val Ile Pro Pro Gly Gly Lys Val Val Asn Ser Asp
     210                 215                 220

Ile Ser Cys His Tyr Lys Lys Tyr Pro Met His Val Phe Ala Tyr Arg
225                 230                 235                 240

Val His Thr His His Leu Gly Lys Val Val Ser Gly Tyr Arg Val Arg
                 245                 250                 255

Asn Gly Gln Trp Thr Leu Ile Gly Arg Gln Ser Pro Gln Leu Pro Gln
             260                 265                 270

Ala Phe Tyr Pro Val Glu His Pro Val Asp Val Ser Phe Gly Asp Ile
         275                 280                 285

Leu Ala Ala Arg Cys Val Phe Thr Gly Glu Gly Arg Thr Glu Val Thr
     290                 295                 300

His Ile Gly Gly Thr Ser Ser Asp Glu Met Cys Asn Leu Tyr Ile Met
305                 310                 315                 320

Tyr Tyr Met Glu Ala Lys His Ala Val Ser Phe Met Thr Cys Thr Gln
                 325                 330                 335

Asn Val Ala Pro Asp Ile Phe Arg Thr Ile Pro Pro Glu Ala Asn Ile
             340                 345                 350

Pro Ile Pro Val Lys Ser Asp Met Val Met Met Xaa Xaa Xaa Xaa His
         355                 360                 365

Gly His His Lys Glu Thr Glu Asn Lys Asp Lys Thr Ser Leu Leu Gln
             370                 375                 380

Gln Pro Lys Arg Glu Glu Glu Gly Val Leu Glu Gln Gly Asp Phe Tyr
385                 390                 395                 400
```

```
Ser  Leu  Leu  Ser  Lys  Leu  Leu  Gly  Glu  Arg  Glu  Asp  Val  Val  His  Val
               405                      410                     415

His  Lys  Tyr  Asn  Pro  Thr  Glu  Lys  Ala  Glu  Ser  Glu  Ser  Asp  Leu  Val
               420                 425                     430

Ala  Glu  Ile  Ala  Asn  Val  Val  Gln  Lys  Lys  Asp  Leu  Gly  Arg  Ser  Asp
          435                      440                     445

Thr  Arg  Glu  Ser  Ala  Glu  Xaa  Gln  Glu  Xaa  Arg  Gly  Asn  Ala  Ile  Leu
     450                      455                     460

Val  Arg  Asp  Arg  Ile  His  Lys  Phe  His  Arg  Leu  Val  Ser  Thr  Leu  Arg
465                      470                     475                      480

Pro  Ala  Glu  Ser  Arg  Val  Leu  Ser  Leu  Gln  Gln  Pro  Leu  Pro  Gly  Glu
               485                      490                          495

Gly  Thr  Trp  Glu  Pro  Glu  His  Thr  Gly  Asp  Phe  His  Val  Glu  Glu  Ala
               500                      505                     510

Leu  Asp  Trp  Pro  Gly  Val  Tyr  Leu  Leu  Pro  Gly  Gln  Val  Ser  Gly  Val
               515                      520                     525

Ala  Leu  Asp  Pro  Gln  Asn  Asn  Leu  Val  Ile  Phe  His  Arg  Gly  Asp  His
     530                      535                     540

Val  Trp  Asp  Gly  Asn  Ser  Phe  Asp  Ser  Lys  Phe  Val  Tyr  Gln  Gln  Arg
545                      550                     555                      560

Gly  Leu  Gly  Pro  Ile  Glu  Glu  Asp  Thr  Ile  Leu  Val  Ile  Asp  Pro  Asn
               565                      570                     575

Asn  Ala  Ala  Val  Leu  Gln  Ser  Ser  Gly  Lys  Asn  Leu  Phe  Tyr  Leu  Pro
               580                      585                     590

His  Gly  Leu  Ser  Ile  Asp  Lys  Asp  Gly  Asn  Tyr  Trp  Val  Thr  Asp  Val
               595                      600                     605

Ala  Leu  His  Gln  Val  Phe  Lys  Leu  Asp  Pro  Lys  Ser  Lys  Glu  Gly  Pro
     610                      615                     620

Leu  Leu  Thr  Leu  Gly  Arg  Ser  Met  Gln  Pro  Gly  Ser  Asp  Gln  Asn  His
625                      630                     635                      640

Phe  Cys  Gln  Pro  Thr  Asp  Val  Ala  Val  Asp  Pro  Asp  Thr  Gly  Thr  Ile
               645                      650                     655

Tyr  Val  Ser  Asp  Gly  Tyr  Cys  Asn  Ser  Arg  Leu  Val  Gln  Phe  Ser  Pro
               660                      665                     670

Ser  Gly  Lys  Phe  Ile  Thr  His  Trp  Gly  Glu  Ala  Ser  Leu  Glu  Ser  Ser
               675                      680                     685

Pro  Lys  Pro  Gly  Gln  Phe  Arg  Val  Pro  His  Ser  Leu  Ala  Leu  Val  Pro
     690                      695                     700

Pro  Leu  Gly  Gln  Leu  Cys  Val  Ala  Asp  Arg  Glu  Asn  Gly  Arg  Ile  Gln
705                      710                     715                      720

Cys  Phe  Lys  Thr  Asp  Thr  Lys  Glu  Phe  Val  Arg  Glu  Ile  Lys  His  Pro
               725                      730                     735

Ser  Phe  Gly  Arg  Asn  Val  Phe  Ala  Ile  Ser  Tyr  Ile  Pro  Xaa  Gly  Leu
               740                      745                     750

Leu  Phe  Ala  Val  Asn  Gly  Lys  Pro  Tyr  Phe  Glu  Asp  Gln  Glu  Pro  Val
               755                      760                     765

Gln  Gly  Phe  Val  Met  Asn  Phe  Ser  Ser  Gly  Glu  Ile  Ile  Asp  Val  Phe
     770                      775                     780

Lys  Pro  Val  Arg  Lys  His  Phe  Asp  Met  Pro  His  Asp  Ile  Ala  Ala  Ser
785                      790                     795                      800

Glu  Asp  Gly  Thr  Val  Tyr  Val  Gly  Asp  Ala  His  Thr  Asn  Thr  Val  Trp
               805                      810                     815

Lys  Phe  Thr  Ser  Thr  Glu  Lys  Met  Glu  His  Arg  Ser  Val  Lys  Lys  Ala
```

|   |   |   | 820 |   |   |   | 825 |   |   |   | 830 |   |   |
|---|---|---|---|---|---|---|---|---|---|---|---|---|---|
| Gly | Ile | Glu | Val | Gln | Glu | Ile | Lys | Glu | Ser | Glu | Ala | Val | Glu | Thr |
|   |   | 835 |   |   |   |   | 840 |   |   |   | 845 |   |   |   |
| Lys | Met | Xaa | Xaa | Glu | Asn | Lys | Pro | Ala | Ser | Ser | Glu | Leu | Gln | Lys | Ile |
|   |   | 850 |   |   |   | 855 |   |   |   | 860 |   |   |   |
| Gln | Glu | Lys | Gln | Lys | Leu | Val | Lys | Glu | Pro | Gly | Ser | Gly | Val | Pro | Ala |
| 865 |   |   |   |   | 870 |   |   |   |   | 875 |   |   |   |   | 880 |
| Val | Leu | Ile | Thr | Thr | Leu | Leu | Val | Ile | Pro | Val | Val | Val | Leu | Leu | Ala |
|   |   |   |   | 885 |   |   |   |   | 890 |   |   |   |   | 895 |
| Ile | Ala | Leu | Phe | Ile | Arg | Trp | Lys | Lys | Ser | Arg | Xaa | Ala | Phe | Gly | Asp |
|   |   |   | 900 |   |   |   | 905 |   |   |   | 910 |   |   |   |
|   | Ser | Glu | Arg | Lys | Leu | Glu | Ala | Ser | Ser | Gly | Arg | Val | Leu | Gly | Arg | Leu |
|   |   | 915 |   |   |   |   | 920 |   |   |   | 925 |   |   |   |
| Arg | Gly | Lys | Gly | Gly | Gly | Gly | Leu | Asn | Leu | Gly | Asn | Phe | Phe | Ala | Ser |
|   |   | 930 |   |   |   | 935 |   |   |   | 940 |   |   |   |
| Arg | Lys | Gly | Tyr | Ser | Arg | Lys | Gly | Phe | Asp | Arg | Leu | Ser | Thr | Glu | Gly |
| 945 |   |   |   |   | 950 |   |   |   |   | 955 |   |   |   |   | 960 |
| Ser | Asp | Gln | Glu | Lys | Xaa | Asp | Glu | Xaa | Asp | Ala | Ser | Glu | Ser | Glu | Glu |
|   |   |   |   | 965 |   |   |   |   | 970 |   |   |   |   | 975 |
| Glu | Tyr | Ser | Ala | Pro | Pro | Pro | Ala | Pro | Ala | Pro | Ser | Ser |
|   |   |   | 980 |   |   |   |   | 985 |

( 2 ) INFORMATION FOR SEQ ID NO:15:

( i ) SEQUENCE CHARACTERISTICS:
        ( A ) LENGTH: 404 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Frog ( x i ) SEQUENCE DESCRIPTION: SEQ ID NO:15:

| Met | Ala | Ser | Xaa | Leu | Ser | Ser | Ser | Xaa | Phe | Leu | Val | Leu | Xaa | Xaa | Phe |
|---|---|---|---|---|---|---|---|---|---|---|---|---|---|---|---|
| 1 |   |   |   | 5 |   |   |   |   | 10 |   |   |   |   | 15 |
| Leu | Leu | Phe | Gln | Asn | Ser | Cys | Tyr | Cys | Phe | Arg | Ser | Pro | Leu | Ser | Val |
|   |   |   | 20 |   |   |   | 25 |   |   |   |   | 30 |
| Phe | Lys | Arg | Tyr | Glu | Glu | Ser | Thr | Arg | Ser | Leu | Ser | Asn | Asp | Cys | Leu |
|   |   | 35 |   |   |   |   | 40 |   |   |   | 45 |   |   |   |
| Gly | Thr | Thr | Arg | Pro | Val | Met | Ser | Pro | Gly | Ser | Ser | Asp | Tyr | Thr | Leu |
|   | 50 |   |   |   |   | 55 |   |   |   |   | 60 |   |   |   |
| Asp | Ile | Arg | Met | Pro | Gly | Val | Thr | Pro | Thr | Glu | Ser | Asp | Thr | Tyr | Leu |
| 65 |   |   |   |   | 70 |   |   |   |   | 75 |   |   |   |   | 80 |
| Cys | Lys | Ser | Tyr | Arg | Leu | Pro | Val | Asp | Asp | Glu | Ala | Tyr | Val | Val | Asp |
|   |   |   |   | 85 |   |   |   |   | 90 |   |   |   |   | 95 |
| Phe | Arg | Pro | His | Ala | Asn | Met | Asp | Thr | Ala | His | His | Met | Leu | Leu | Phe |
|   |   |   | 100 |   |   |   | 105 |   |   |   | 110 |   |   |   |
| Gly | Cys | Asn | Ile | Pro | Ser | Ser | Thr | Gly | Asp | Tyr | Trp | Asp | Cys | Ser | Ala |
|   |   | 115 |   |   |   |   | 120 |   |   |   | 125 |   |   |   |
| Gly | Thr | Met | Asp | Lys | Ser | Ser | Ile | Met | Tyr | Ala | Trp | Ala | Lys | Asn | Ala |
|   | 130 |   |   |   |   | 135 |   |   |   |   | 140 |   |   |   |
| Pro | Pro | Thr | Lys | Leu | Pro | Glu | Gly | Val | Gly | Phe | Arg | Val | Gly | Gly | Lys |
| 145 |   |   |   |   | 150 |   |   |   |   | 155 |   |   |   |   | 160 |
| Ser | Gly | Ser | Arg | Tyr | Phe | Val | Leu | Gln | Val | His | Tyr | Gly | Asn | Val | Lys |
|   |   |   |   | 165 |   |   |   |   | 170 |   |   |   |   | 175 |

```
Ala  Phe  Gln  Asp  Lys  His  Lys  Asp  Thr  Gly  Val  Thr  Val  Arg  Val  Thr
               180                      185                     190

Pro  Glu  Lys  Gln  Pro  Gln  Ile  Ala  Gly  Ile  Tyr  Leu  Ser  Met  Ser  Val
          195                      200                     205

Asp  Thr  Val  Ile  Pro  Pro  Gly  Glu  Glu  Ala  Val  Asn  Ser  Asp  Ile  Ala
     210                      215                     220

Cys  Leu  Tyr  Asn  Arg  Pro  Thr  Ile  His  Pro  Phe  Ala  Tyr  Arg  Val  His
225                      230                     235                          240

Thr  His  Gln  Leu  Gly  Gln  Val  Val  Ser  Gly  Phe  Arg  Val  Arg  His  Gly
                    245                     250                     255

Lys  Trp  Ser  Leu  Ile  Gly  Arg  Gln  Ser  Pro  Gln  Leu  Pro  Gln  Ala  Phe
                    260                     265                     270

Val  Pro  Val  Glu  His  Pro  Val  Glu  Ile  Ser  Pro  Gly  Asp  Ile  Ile  Ala
               275                      280                     285

Thr  Arg  Cys  Leu  Phe  Thr  Gly  Lys  Gly  Arg  Thr  Ser  Ala  Thr  Tyr  Ile
          290                      295                     300

Gly  Gly  Thr  Ser  Asn  Asp  Glu  Met  Cys  Asn  Leu  Tyr  Ile  Met  Tyr  Tyr
305                      310                     315                          320

Met  Asp  Ala  Ala  His  Ala  Thr  Ser  Tyr  Met  Thr  Cys  Val  Gln  Thr  Gly
                    325                     330                     335

Glu  Pro  Lys  Leu  Phe  Gln  Asn  Ile  Pro  Glu  Ile  Ala  Asn  Val  Pro  Ile
                    340                     345                     350

Pro  Val  Ser  Pro  Asp  Met  Met  Met  Xaa  Xaa  Met  Gly  His  Gly  His
               355                      360                     365

His  His  Thr  Glu  Ala  Glu  Pro  Glu  Lys  Asn  Thr  Gly  Leu  Gln  Gln  Pro
     370                      375                     380

Lys  Arg  Glu  Glu  Glu  Glu  Val  Leu  Asp  Gln  Gly  Leu  Ile  Thr  Leu  Gly
385                      390                     395                          400

Asp  Ser  Ala  Val
```

( 2 ) INFORMATION FOR SEQ ID NO:16:

( i ) SEQUENCE CHARACTERISTICS:
        ( A ) LENGTH: 989 amino acids
        ( B ) TYPE: amino acid
        ( C ) STRANDEDNESS: single
        ( D ) TOPOLOGY: linear ( i i ) MOLECULE TYPE: protein ( v i ) ORIGINAL SOURCE:
        ( A ) ORGANISM: Frog ( x i ) SEQUENCE DESCRIPTION: SEQ ID NO:16:

```
Met  Asp  Met  Ala  Ser  Xaa  Leu  Ile  Ser  Ser  Xaa  Leu  Leu  Val  Leu  Xaa
1                   5                    10                      15

Xaa  Phe  Leu  Ile  Phe  Gln  Asn  Ser  Cys  Tyr  Cys  Phe  Arg  Ser  Pro  Leu
               20                      25                      30

Ser  Val  Phe  Lys  Arg  Tyr  Glu  Glu  Ser  Thr  Arg  Ser  Leu  Ser  Asn  Asp
          35                      40                      45

Cys  Leu  Gly  Thr  Thr  Arg  Pro  Val  Met  Ser  Pro  Gly  Ser  Ser  Asp  Tyr
     50                      55                      60

Thr  Leu  Asp  Ile  Arg  Met  Pro  Gly  Val  Thr  Pro  Thr  Glu  Ser  Asp  Thr
65                       70                      75                          80

Tyr  Leu  Cys  Lys  Ser  Tyr  Arg  Leu  Pro  Val  Asp  Asp  Glu  Ala  Tyr  Val
               85                      90                      95

Val  Asp  Tyr  Arg  Pro  His  Ala  Asn  Met  Asp  Thr  Ala  His  His  Met  Leu
```

-continued

|       |       |       |       |       | 100   |       |       |       | 105   |       |       |       | 110   |       |
|-------|-------|-------|-------|-------|-------|-------|-------|-------|-------|-------|-------|-------|-------|-------|
| Leu   | Phe   | Gly   | Cys   | Asn   | Val   | Pro   | Ser   | Ser   | Thr   | Gly   | Asp   | Tyr   | Trp   | Asp   | Cys   |
|       |       | 115   |       |       |       |       | 120   |       |       |       |       | 125   |       |       |
| Ser   | Ala   | Gly   | Thr   | Cys   | Asn   | Asp   | Lys   | Ser   | Ser   | Ile   | Met   | Tyr   | Ala   | Trp   | Ala   |
|       | 130   |       |       |       |       | 135   |       |       |       |       | 140   |       |       |       |
| Lys   | Asn   | Ala   | Pro   | Pro   | Thr   | Lys   | Leu   | Pro   | Glu   | Gly   | Val   | Gly   | Phe   | Gln   | Val   |
| 145   |       |       |       |       | 150   |       |       |       |       | 155   |       |       |       |       | 160   |
| Gly   | Gly   | Lys   | Ser   | Gly   | Ser   | Arg   | Tyr   | Phe   | Val   | Leu   | Gln   | Val   | His   | Tyr   | Gly   |
|       |       |       |       | 165   |       |       |       |       | 170   |       |       |       |       | 175   |       |
| Asp   | Val   | Lys   | Ala   | Phe   | Gln   | Asp   | Lys   | His   | Lys   | Asp   | Thr   | Gly   | Val   | Thr   | Val   |
|       |       |       | 180   |       |       |       |       | 185   |       |       |       |       | 190   |       |       |
| Arg   | Ile   | Thr   | Pro   | Glu   | Lys   | Gln   | Pro   | Leu   | Ile   | Ala   | Gly   | Ile   | Tyr   | Leu   | Ser   |
|       |       | 195   |       |       |       |       | 200   |       |       |       |       | 205   |       |       |       |
| Met   | Ser   | Leu   | Asn   | Thr   | Val   | Val   | Pro   | Pro   | Gly   | Gln   | Glu   | Val   | Val   | Asn   | Ser   |
|       |       | 210   |       |       |       | 215   |       |       |       |       | 220   |       |       |       |       |
| Asp   | Ile   | Ala   | Cys   | Leu   | Tyr   | Asn   | Arg   | Pro   | Thr   | Ile   | His   | Pro   | Phe   | Ala   | Tyr   |
| 225   |       |       |       |       | 230   |       |       |       |       | 235   |       |       |       |       | 240   |
| Arg   | Val   | His   | Thr   | His   | Gln   | Leu   | Gly   | Gln   | Val   | Val   | Ser   | Gly   | Phe   | Arg   | Val   |
|       |       |       |       | 245   |       |       |       |       | 250   |       |       |       |       | 255   |       |
| Arg   | His   | Gly   | Lys   | Trp   | Thr   | Leu   | Ile   | Gly   | Arg   | Gln   | Ser   | Pro   | Gln   | Leu   | Pro   |
|       |       |       | 260   |       |       |       |       | 265   |       |       |       |       | 270   |       |       |
| Gln   | Ala   | Phe   | Tyr   | Pro   | Val   | Glu   | His   | Pro   | Leu   | Glu   | Ile   | Ser   | Pro   | Gly   | Asp   |
|       |       | 275   |       |       |       |       | 280   |       |       |       |       | 285   |       |       |       |
| Ile   | Ile   | Ala   | Thr   | Arg   | Leu   | Phe   | Thr   | Gly   | Lys   | Gly   | Arg   | Met   | Ser   | Ala   | Thr   |
|       |       | 290   |       |       |       |       | 295   |       |       |       |       | 300   |       |       |       |
| Tyr   | Ile   | Gly   | Gly   | Thr   | Ala   | Lys   | Asp   | Glu   | Met   | Cys   | Asn   | Leu   | Tyr   | Ile   | Met   |
| 305   |       |       |       |       | 310   |       |       |       |       | 315   |       |       |       |       | 320   |
| Tyr   | Tyr   | Met   | Asp   | Ala   | Ala   | His   | Ala   | Thr   | Ser   | Tyr   | Met   | Thr   | Cys   | Val   | Gln   |
|       |       |       |       | 325   |       |       |       |       | 330   |       |       |       |       | 335   |       |
| Thr   | Gly   | Asn   | Pro   | Lys   | Leu   | Phe   | Glu   | Asn   | Ile   | Pro   | Glu   | Ile   | Ala   | Asn   | Val   |
|       |       |       | 340   |       |       |       |       | 345   |       |       |       |       | 350   |       |       |
| Pro   | Ile   | Pro   | Val   | Ser   | Pro   | Asp   | Met   | Met   | Met   | Met   | Met   | Met   | Met   | Gly   | His   |
|       |       | 355   |       |       |       |       | 360   |       |       |       |       | 365   |       |       |       |
| Gly   | His   | His   | His   | Thr   | Glu   | Ala   | Glu   | Ala   | Glu   | Thr   | Asn   | Thr   | Ala   | Leu   | Gln   |
|       |       | 370   |       |       |       |       | 375   |       |       |       |       | 380   |       |       |       |
| Gln   | Pro   | Lys   | Arg   | Glu   | Glu   | Glu   | Glu   | Val   | Leu   | Asn   | Gln   | Xaa   | Xaa   | Xaa   | Xaa   |
| 385   |       |       |       |       | 390   |       |       |       |       | 395   |       |       |       |       | 400   |
| Xaa   | Xaa   | Xaa   | Xaa   | Xaa   | Xaa   | Xaa   | Xaa   | Xaa   | Xaa   | Xaa   | Xaa   | Xaa   | Xaa   | Xaa   | Xaa   |
|       |       |       |       | 405   |       |       |       |       | 410   |       |       |       |       | 415   |       |
| Xaa   | Xaa   | Xaa   | Xaa   | Xaa   | Xaa   | Xaa   | Xaa   | Xaa   | Xaa   | Xaa   | Xaa   | Xaa   | Xaa   | Xaa   | Xaa   |
|       |       |       | 420   |       |       |       |       | 425   |       |       |       |       | 430   |       |       |
| Xaa   | Xaa   | Xaa   | Xaa   | Xaa   | Xaa   | Xaa   | Xaa   | Xaa   | Xaa   | Xaa   | Xaa   | Xaa   | Xaa   | Xaa   | Xaa   |
|       |       |       |       | 435   |       |       |       |       | 440   |       |       |       |       | 445   |       |
| Xaa   | Xaa   | Xaa   | Xaa   | Xaa   | Xaa   | Xaa   | Xaa   | Xaa   | Xaa   | Xaa   | Xaa   | Xaa   | Xaa   | Xaa   | Xaa   |
|       | 450   |       |       |       |       | 455   |       |       |       |       | 460   |       |       |       |       |
| Xaa   | Xaa   | Xaa   | Xaa   | Xaa   | Xaa   | Xaa   | Xaa   | Xaa   | Xaa   | Xaa   | Xaa   | Xaa   | Xaa   | Xaa   | Xaa   |
| 465   |       |       |       |       | 470   |       |       |       |       | 475   |       |       |       |       | 480   |
| Xaa   | Xaa   | Xaa   | Xaa   | Xaa   | Xaa   | Xaa   | Xaa   | Xaa   | Xaa   | Xaa   | Xaa   | Xaa   | Xaa   | Xaa   | Xaa   |
|       |       |       |       | 485   |       |       |       |       | 490   |       |       |       |       | 495   |       |
| Xaa   | Xaa   | Xaa   | Xaa   | Xaa   | Xaa   | Xaa   | Xaa   | Xaa   | Asp   | Val   | His   | Leu   | Glu   | Glu   | Asp   |
|       |       |       | 500   |       |       |       |       | 505   |       |       |       |       | 510   |       |       |
| Thr   | Asp   | Trp   | Pro   | Gly   | Val   | Asn   | Leu   | Lys   | Val   | Gly   | Gln   | Val   | Ser   | Gly   | Leu   |
|       |       | 515   |       |       |       |       | 520   |       |       |       |       | 525   |       |       |       |

```
Ala  Leu  Asp  Pro  Lys  Asn  Asn  Leu  Val  Ile  Phe  His  Arg  Gly  Asp  His
     530                 535                 540

Val  Trp  Asp  Glu  Asn  Ser  Phe  Asp  Arg  Asn  Phe  Val  Tyr  Gln  Gln  Arg
545                      550                 555                           560

Gly  Ile  Gly  Pro  Ile  Gln  Glu  Ser  Thr  Ile  Leu  Val  Val  Asp  Pro  Asn
                    565                 570                           575

Thr  Ser  Lys  Val  Leu  Lys  Ser  Thr  Gln  Asn  Leu  Phe  Phe  Leu  Pro
               580                 585                      590

His  Gly  Leu  Thr  Ile  Asp  Arg  Asp  Gly  Asn  Tyr  Trp  Val  Thr  Asp  Val
               595                 600                 605

Ala  Leu  His  Gln  Val  Phe  Lys  Xaa  Val  Gly  Ala  Glu  Lys  Glu  Thr  Pro
     610                 615                      620

Leu  Leu  Val  Leu  Gly  Arg  Ala  Phe  Gln  Pro  Gly  Ser  Asp  Arg  Lys  His
625                      630                 635                           640

Phe  Cys  Gln  Pro  Thr  Asp  Val  Ala  Val  Asp  Pro  Ile  Thr  Gly  Asn  Phe
                    645                 650                           655

Phe  Val  Ala  Asp  Gly  Tyr  Cys  Asn  Ser  Arg  Ile  Met  Gln  Phe  Ser  Pro
               660                 665                      670

Asn  Gly  Met  Phe  Ile  Met  Gln  Trp  Gly  Glu  Glu  Thr  Ser  Ser  Asn  Leu
          675                 680                      685

Pro  Arg  Pro  Gly  Gln  Phe  Arg  Ile  Pro  His  Ser  Leu  Thr  Met  Ile  Ser
     690                 695                      700

Asp  Gln  Gly  Gln  Leu  Cys  Val  Ala  Asp  Arg  Glu  Asn  Gly  Arg  Ile  Gln
705                      710                 715                           720

Cys  Phe  His  Ala  Lys  Thr  Gly  Glu  Phe  Val  Lys  Gln  Ile  Lys  His  Gln
                    725                 730                           735

Glu  Phe  Gly  Arg  Glu  Val  Phe  Ala  Val  Ser  Tyr  Ala  Pro  Gly  Gly  Val
               740                 745                      750

Leu  Tyr  Ala  Val  Asn  Gly  Lys  Pro  Tyr  Tyr  Gly  Asp  Ser  Thr  Pro  Val
          755                 760                      765

Gln  Gly  Phe  Met  Ile  Asn  Phe  Ser  Asn  Gly  Asp  Ile  Leu  Asp  Thr  Phe
770                      775                 780

Ile  Pro  Ala  Arg  Lys  Asn  Phe  Glu  Met  Pro  His  Asp  Ile  Ala  Ala  Gly
785                      790                 795                           800

Asp  Asp  Gly  Thr  Val  Tyr  Val  Gly  Asp  Ala  His  Ala  Asn  Ala  Val  Trp
                    805                 810                           815

Lys  Phe  Xaa  Ser  Pro  Ser  Lys  Ala  Glu  His  Arg  Ser  Val  Lys  Lys  Ala
               820                 825                      830

Gly  Ile  Glu  Val  Glu  Glu  Ile  Thr  Glu  Thr  Glu  Xaa  Ile  Phe  Glu  Thr
          835                 840                 845

His  Met  Arg  Ser  Arg  Pro  Lys  Thr  Asn  Glu  Ser  Val  Gly  Gln  Gln  Thr
850                      855                 860

Gln  Glu  Lys  Pro  Ser  Val  Val  Gln  Glu  Ser  Ser  Ala  Gly  Val  Ser  Phe
865                      870                 875                           880

Val  Leu  Ile  Ile  Thr  Leu  Leu  Ile  Ile  Pro  Val  Val  Leu  Ile  Ala
                    885                 890                           895

Ile  Ala  Ile  Phe  Ile  Arg  Trp  Arg  Lys  Val  Arg  Met  Tyr  Gly  Gly  Asp
               900                 905                      910

Ile  Gly  His  Lys  Ser  Glu  Ser  Ser  Gly  Gly  Ile  Leu  Gly  Lys  Leu
          915                 920                      925

Arg  Gly  Lys  Gly  Ser  Gly  Gly  Leu  Asn  Leu  Gly  Thr  Phe  Phe  Ala  Thr
     930                 935                      940

His  Lys  Gly  Tyr  Ser  Arg  Lys  Gly  Phe  Asp  Arg  Leu  Ser  Thr  Glu  Gly
945                      950                 955                           960
```

| Ser | Asp | Gln | Gln | Lys | Asp | Asp | Asp | Asp | Gly | Ser | Asp | Ser | Glu | Glu | Glu |
|||||965||||970||||||975||

| Tyr | Ser | Ala | Pro | Pro | Ile | Pro | Pro | Val | Xaa | Ser | Ser | Ser |
||||980|||||985||||

(2) INFORMATION FOR SEQ ID NO:17:

(i) SEQUENCE CHARACTERISTICS:
        (A) LENGTH: 989 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Rat (xi) SEQUENCE DESCRIPTION: SEQ ID NO:17:

| Met | Ala | Gly | Arg | Ala | Arg | Ser | Gly | Leu | Leu | Leu | Leu | Leu | Leu | Gly | Leu |
|1||||5||||10|||||15||

| Leu | Ala | Leu | Gln | Ser | Ser | Cys | Leu | Ala | Phe | Arg | Ser | Pro | Leu | Ser | Val |
||||20|||||25||||30|||

| Phe | Lys | Arg | Phe | Lys | Glu | Thr | Thr | Arg | Ser | Phe | Ser | Asn | Glu | Cys | Leu |
|||35|||||40||||||45|||

| Gly | Thr | Ile | Gly | Pro | Val | Thr | Pro | Leu | Asp | Ala | Ser | Asp | Phe | Ala | Leu |
||50||||||55||||60||||

| Asp | Ile | Arg | Met | Pro | Gly | Val | Thr | Pro | Lys | Glu | Ser | Asp | Thr | Tyr | Phe |
|65||||||70||||75||||||80|

| Cys | Met | Ser | Met | Arg | Leu | Pro | Val | Asp | Glu | Ala | Phe | Val | Ile | Asp |
|||||85||||90||||95||

| Phe | Lys | Pro | Arg | Ala | Ser | Met | Asp | Thr | Val | His | His | Met | Leu | Leu | Phe |
||||100||||105||||||110||

| Gly | Cys | Asn | Met | Pro | Ser | Ser | Thr | Gly | Ser | Tyr | Trp | Phe | Cys | Asp | Glu |
|||115||||||120||||125|||

| Gly | Thr | Cys | Thr | Asp | Lys | Ala | Asn | Ile | Leu | Tyr | Ala | Trp | Ala | Arg | Asn |
||130|||||135|||||140||||

| Ala | Pro | Pro | Thr | Arg | Leu | Pro | Lys | Gly | Val | Gly | Phe | Arg | Val | Gly | Gly |
|145||||150||||||155|||||160|

| Glu | Thr | Gly | Ser | Lys | Tyr | Phe | Leu | Val | Leu | Gln | Val | His | Tyr | Gly | Asp |
|||||165||||170|||||175||

| Ile | Ser | Ala | Phe | Arg | Asp | Asn | His | Lys | Asp | Cys | Ser | Gly | Val | Ser | Val |
||||180|||||185||||190|||

| His | Leu | Thr | Arg | Val | Pro | Gln | Pro | Leu | Ile | Ala | Gly | Met | Tyr | Leu | Met |
|||195||||200|||||205||||

| Met | Ser | Val | Asp | Thr | Val | Ile | Pro | Pro | Gly | Glu | Lys | Val | Val | Asn | Ala |
||210||||215|||||220|||||

| Asp | Ile | Ser | Cys | Gln | Tyr | Lys | Met | Tyr | Pro | Met | His | Val | Phe | Ala | Tyr |
|225|||||230||||235|||||240|

| Arg | Val | His | Thr | His | His | Leu | Gly | Lys | Val | Val | Ser | Gly | Tyr | Arg | Val |
|||||245|||||250||||255||

| Arg | Asn | Gly | Gln | Trp | Thr | Leu | Ile | Gly | Arg | Gln | Asn | Pro | Gln | Leu | Pro |
||||260|||||265||||270|||

| Gln | Ala | Phe | Tyr | Pro | Val | Glu | His | Pro | Val | Asp | Val | Thr | Phe | Gly | Asp |
|||275||||280|||||285||||

| Ile | Leu | Ala | Ala | Arg | Cys | Val | Phe | Thr | Gly | Glu | Gly | Arg | Thr | Glu | Ala |
||290||||295|||||300|||||

```
Thr His Ile Gly Gly Thr Ser Ser Asp Glu Met Cys Asn Leu Tyr Ile
305                 310                 315                 320

Met Tyr Tyr Met Glu Ala Lys Tyr Ala Leu Ser Phe Met Thr Cys Thr
            325                 330                 335

Lys Asn Val Ala Pro Asp Met Phe Arg Thr Ile Pro Ala Glu Ala Asn
            340                 345                 350

Ile Pro Ile Pro Val Lys Pro Asp Met Val Met Met Xaa Xaa Xaa Xaa
            355                 360                 365

His Gly His His Lys Glu Ala Glu Asn Lys Glu Lys Ser Ala Leu Met
    370                 375                 380

Gln Gln Pro Lys Gln Gly Glu Glu Glu Val Leu Glu Gln Gly Asp Phe
385                 390                 395                 400

Tyr Ser Leu Leu Ser Lys Leu Leu Gly Glu Arg Glu Asp Xaa Val His
                405                 410                 415

Val His Lys Tyr Asn Pro Thr Glu Lys Thr Glu Ser Gly Ser Asp Leu
            420                 425                 430

Val Ala Glu Ile Ala Asn Val Val Gln Lys Lys Asp Leu Gly Arg Ser
            435                 440                 445

Asp Ala Arg Glu Gly Ala Glu His Glu Glu Xaa Trp Gly Asn Ala Ile
    450                 455                 460

Leu Val Arg Asp Arg Ile His Arg Phe His Gln Leu Glu Ser Thr Leu
465                 470                 475                 480

Arg Pro Ala Glu Ser Arg Ala Phe Ser Phe Gln Gln Xaa Xaa Pro Gly
                485                 490                 495

Glu Gly Pro Trp Glu Pro Glu Pro Ser Gly Asp Phe His Val Glu Glu
            500                 505                 510

Glu Leu Asp Trp Pro Gly Val Tyr Leu Leu Pro Gly Gln Val Ser Gly
            515                 520                 525

Val Ala Leu Asp Ser Lys Asn Asn Leu Val Ile Phe His Arg Gly Asp
            530                 535                 540

His Val Trp Asp Gly Asn Ser Phe Asp Ser Lys Phe Val Tyr Gln Gln
545                 550                 555                 560

Arg Gly Leu Gly Pro Ile Glu Glu Asp Thr Ile Leu Val Ile Asp Pro
                565                 570                 575

Asn Asn Ala Glu Ile Leu Gln Ser Ser Gly Lys Asn Leu Phe Tyr Leu
            580                 585                 590

Pro His Gly Leu Ser Ile Asp Thr Asp Gly Asn Tyr Trp Val Thr Asp
        595                 600                 605

Val Ala Leu His Gln Val Phe Lys Leu Asp Pro His Ser Lys Glu Gly
610                 615                 620

Pro Leu Leu Ile Leu Gly Arg Ser Met Gln Pro Gly Ser Asp Gln Asn
625                 630                 635                 640

His Phe Cys Gln Pro Thr Asp Val Ala Val Glu Pro Ser Thr Gly Ala
            645                 650                 655

Val Phe Val Ser Asp Gly Tyr Cys Asn Ser Arg Ile Val Gln Phe Ser
            660                 665                 670

Pro Ser Gly Lys Phe Val Thr Gln Trp Gly Glu Glu Ser Ser Gly Ser
        675                 680                 685

Ser Pro Arg Pro Gly Gln Phe Ser Val Pro His Ser Leu Ala Leu Val
        690                 695                 700

Pro His Leu Asp Gln Leu Cys Val Ala Asp Arg Glu Asn Gly Arg Ile
705                 710                 715                 720

Gln Cys Phe Lys Thr Asp Lys Glu Phe Val Arg Glu Ile Lys His Ala
                725                 730                 735
```

| | | | | | | | | | | | | | |
|---|---|---|---|---|---|---|---|---|---|---|---|---|---|
|Ser|Phe|Gly|Arg<br>740|Asn|Val|Phe|Ala|Ile<br>745|Ser|Tyr|Ile|Pro|Xaa<br>750|Gly|Phe|
|Leu|Phe|Ala<br>755|Val|Asn|Gly|Lys|Pro<br>760|Tyr|Phe|Gly|Asp|Gln<br>765|Glu|Pro|Val|
|Gln|Gly<br>770|Phe|Val|Met|Asn|Phe<br>775|Ser|Ser|Gly|Glu|Ile<br>780|Ile|Asp|Val|Phe|
|Lys<br>785|Pro|Val|Arg|Lys|His<br>790|Phe|Asp|Met|Pro|His<br>795|Asp|Ile|Val|Ala|Ser<br>800|
|Glu|Asp|Gly|Thr|Val<br>805|Tyr|Ile|Gly|Asp|Ala<br>810|His|Thr|Asn|Thr|Val<br>815|Trp|
|Lys|Phe|Thr|Leu<br>820|Thr|Glu|Lys|Met|Glu<br>825|His|Arg|Ser|Val|Lys<br>830|Lys|Ala|
|Gly|Ile|Glu<br>835|Val|Gln|Glu|Ile|Lys<br>840|Glu|Ala|Glu|Ala|Val<br>845|Val|Glu|Pro|
|Lys|Val<br>850|Xaa|Xaa|Glu|Asn|Lys<br>855|Pro|Thr|Ser|Ser|Glu<br>860|Leu|Gln|Lys|Met|
|Gln<br>865|Glu|Lys|Gln|Lys|Leu<br>870|Ser|Thr|Glu|Pro|Gly<br>875|Ser|Gly|Val|Ser|Val<br>880|
|Val|Leu|Ile|Thr|Thr<br>885|Leu|Leu|Val|Ile|Pro<br>890|Val|Leu|Val|Leu|Leu<br>895|Ala|
|Ile|Val|Met|Phe<br>900|Ile|Arg|Trp|Lys|Lys<br>905|Ser|Arg|Xaa|Ala|Phe<br>910|Gly|Asp|
|His|Asp|Arg<br>915|Lys|Leu|Glu|Ser|Ser<br>920|Ser|Gly|Arg|Val|Leu<br>925|Gly|Arg|Phe|
|Arg|Gly<br>930|Lys|Gly|Ser|Gly|Gly<br>935|Leu|Asn|Leu|Gly|Asn<br>940|Phe|Phe|Ala|Ser|
|Arg<br>945|Lys|Gly|Tyr|Ser|Arg<br>950|Lys|Gly|Phe|Asp|Arg<br>955|Val|Ser|Thr|Glu|Gly<br>960|
|Ser|Asp|Gln|Glu|Lys<br>965|Xaa|Asp|Glu|Asp|Asp<br>970|Gly|Thr|Glu|Ser|Glu<br>975|Glu|
|Glu|Tyr|Ser|Ala|Pro<br>980|Leu|Pro|Lys|Pro|Ala<br>985|Pro|Ser|Ser| | | |

( 2 ) INFORMATION FOR SEQ ID NO:18:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:18:

Ser  Leu  Ala  Phe  Gly
1                         5

( 2 ) INFORMATION FOR SEQ ID NO:19:

( i ) SEQUENCE CHARACTERISTICS:
        ( A ) LENGTH: 10 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

C A T C T G A A A C                            1 0

(2) INFORMATION FOR SEQ ID NO:20:

(i) SEQUENCE CHARACTERISTICS:
  (A) LENGTH: 10 base pairs
  (B) TYPE: nucleic acid
  (C) STRANDEDNESS: single
  (D) TOPOLOGY: linear (ii) MOLECULE TYPE: DNA (genomic)

(xi) SEQUENCE DESCRIPTION: SEQ ID NO:20:

```
ACTTTGGGCC                                                                    10
```

(2) INFORMATION FOR SEQ ID NO:21:

(i) SEQUENCE CHARACTERISTICS:
  (A) LENGTH: 1172 base pairs
  (B) TYPE: nucleic acid
  (C) STRANDEDNESS: single
  (D) TOPOLOGY: linear (ii) MOLECULE TYPE: DNA (genomic)

(vi) ORIGINAL SOURCE:
  (A) ORGANISM: Rat (xi) SEQUENCE DESCRIPTION: SEQ ID NO:21:

```
TGCATGTGTT  TGCCTACAGA  GTCCACACTC  ACCATTTAGG  TAAGGTGGTG  AGCGGATACA     60
GAGTAAGAAA  CGGACAGTGG  ACACTGATTG  GACGCCAGAA  CCCCCAGCTG  CCACAGGCTT    120
TCTACCCTGT  GGAACACCCC  GTTGATGTTA  CTTTTGGTGA  TATACTGGCA  GCCAGATGTG    180
TGTTCACTGG  TGAAGGGAGG  ACAGAGGCCA  CCCATATCGG  CGGCACTTCT  AGTGACGAAA    240
TGTGTAACCT  GTACATCATT  GTATTACATG  GAAGCCAAAT  ATGCACTTTC  CTTCATGACC    300
TGTACAAAGA  ACGTGGCTCC  AGATATGTTC  AGAACTATCC  CAGCAGAGGC  CAATATCCCA    360
ATTCCTGTCA  AACCGGACAT  GGTTATGATG  CACGGGCATC  ACAAAGAAGC  AGAAAACAAA    420
GAAAAGAGTG  CTTTAATGCA  GCAGCCAAAA  CAGGGAGAGG  AAGAAGTATT  AGAGCAGGGT    480
GATTTCTATT  CACTGCTTTC  CAAGCTGCTA  GGAGAAAGGG  AAGATGTTCA  TGTGCACAAG    540
TATAATCCTA  CAGAAAAGAC  AGAATCTGGG  TCAGACCTGG  TAGCTGAGAT  TGCAAACGTG    600
GTCCAGAAAA  GGACCTTGGT  CGGTCTGACG  CCAGAGAAGG  TGCAGAGCAT  GAGGAATGGG    660
GTAATGCTAT  CCTAGTCAGA  GACAGGATCC  ACAGATTCCA  CCAGCTAGAG  TCAACTCTGA    720
GGCCAGCTGA  GAGCAGAGCT  TTCTCGTTCC  AGCAGCCTGG  CGAAGGCCCT  TGGGAACCAG    780
AACCCTCAGG  AGATTTCCAT  GTGGAAGAAG  AACTGGACTG  GCCTGGAGTG  TACTTGTTAC    840
CAGGCCAGGT  TTCTGGGGTG  GCCCTGGATT  CTAAGAATAA  CCTAGTGATT  TTCCACAGAG    900
GTGACCATGT  TTGGGATGGA  AACTCTTTTG  ACAGCAAGTT  TGTTACCAG   CAAAGAGGTC    960
TTGGGCCAAT  TGAAGAAGAC  ACCATCCTGG  TCATTGACCC  AAATAATGCT  GAAATCCTCC   1020
AGTCCAGTGG  CAAGAACCTG  TTTTATTTAC  CACACGGCTT  GAGCATAGAT  ACAGATGGAA   1080
ATTATTGGGT  CACAGATGTG  GCTCTCCACC  AGGTGTTCAA  ATTGGACCCG  CATAGCAAAG   1140
AAGGCCCTCT  CTTAATTCTG  GGAAGGAGCA  TG                                   1172
```